United States Patent
Yamauchi

(10) Patent No.: US 11,959,916 B2
(45) Date of Patent: Apr. 16, 2024

(54) METHOD, SYSTEM, AND PROGRAM FOR SUPPLYING IMMUNODYNAMICS-RELATED INFORMATION

(71) Applicant: Tamio Yamauchi, Hiroshima (JP)

(72) Inventor: Tamio Yamauchi, Hiroshima (JP)

( * ) Notice: Subject to any disclaimer, the term of this patent is extended or adjusted under 35 U.S.C. 154(b) by 425 days.

(21) Appl. No.: 16/958,167

(22) PCT Filed: Dec. 25, 2018

(86) PCT No.: PCT/JP2018/047438
§ 371 (c)(1),
(2) Date: Jun. 26, 2020

(87) PCT Pub. No.: WO2019/131578
PCT Pub. Date: Jul. 4, 2019

(65) Prior Publication Data
US 2021/0231655 A1    Jul. 29, 2021

(30) Foreign Application Priority Data

Dec. 26, 2017  (JP) .............................. JP2017-249877

(51) Int. Cl.
*G01N 33/557*     (2006.01)
*G01N 33/569*     (2006.01)
(Continued)

(52) U.S. Cl.
CPC ..... *G01N 33/557* (2013.01); *G01N 33/56972* (2013.01); *G16B 5/00* (2019.02);
(Continued)

(58) Field of Classification Search
CPC .......... G16H 20/00; G16H 20/10; G16B 5/00; G16B 45/00; G16B 50/00; G16B 50/30
(Continued)

(56) References Cited

U.S. PATENT DOCUMENTS

| | | | |
|---|---|---|---|
| 5,639,623 A | 6/1997 | Yamauchi | 435/7.24 |
| 2010/0042329 A1* | 2/2010 | Hood | G01N 33/6803 |
| | | | 702/19 |
| 2012/0195854 A1* | 8/2012 | Krensky | A61K 45/06 |
| | | | 435/375 |

FOREIGN PATENT DOCUMENTS

| | | | |
|---|---|---|---|
| JP | WO9103736 A1 * | 3/1991 | |
| JP | 2568136 | 10/1996 | |

(Continued)

OTHER PUBLICATIONS

Supram Hosuru Subramanya; Primary invasive laryngeal mycosis in an immunocompetent patient: a case report and clinicoepidemiological update; BMC Infectious Diseases 18 BioMed Central. (2018) (Year: 2018).*

(Continued)

*Primary Examiner* — Hiep V Nguyen
(74) *Attorney, Agent, or Firm* — LICATA & TYRRELL P.C.

(57) ABSTRACT

The present invention addresses the problem of providing a method, a system, and a program for supplying immunodynamics-related information that is used in order to readily understand the immunodynamics of the cell-mediated immunity of a subject and to determine a method for treating or a method for preventing a disease and/or a symptom in a subject, This method, system and program supply immunodynamics-related information that is used in order to determine a method for treating or a method for preventing a disease and/or a symptom in a subject by analyzing the number of immunocompetent cells in blood.

12 Claims, 26 Drawing Sheets

(51) Int. Cl.
  *G16B 5/00*  (2019.01)
  *G16B 45/00* (2019.01)
  *G16B 50/30* (2019.01)
  *G16H 20/10* (2018.01)

(52) U.S. Cl.
  CPC .............. *G16B 45/00* (2019.02); *G16B 50/30* (2019.02); *G16H 20/10* (2018.01)

(58) Field of Classification Search
  USPC .......................................................... 705/3
  See application file for complete search history.

(56) References Cited

FOREIGN PATENT DOCUMENTS

| | | | |
|---|---|---|---|
| JP | 2568136 B2 * | 12/1996 | ......... G01N 33/5094 |
| WO | 9103736 | 3/1991 | |
| WO | 2005/004592 | 1/2005 | |
| WO | 2007/038758 | 4/2007 | |
| WO | 2015/060779 | 4/2015 | |
| WO | WO-2016027764 A1 * | 2/2016 | ........... A61K 31/155 |

OTHER PUBLICATIONS

International Search Report and Written Opinion in PCT/JP2018/047438 dated Apr. 2, 2019 with English language translation.

Yamauchi et al. "Discriminant Equations for Predictive Effectiveness of α-Interferon Treatment Against Metastatic Renal Cancer and Multiple Regression Equations for Predictive Survival Periods by Pre-treatment Counts of Peripheral Blood Lymphocyte Subsets and Monocytes" Biotherapy 1996 10(4):671-682.

Yamauchi et al. "Combined Treatment with Interferon-α and -$\gamma_1$ land UFT for Metastatic Renal Cancer Based on Th1 and Th2 Theory: Immunological Study of the Anti-Tumor Effect According to Changes of Peripheral Blood Lymphocyte Subset and Monocyte Counts" Biotherapy 1998 12 (5):731-735.

Yamauchi et al. "Review on Immunotherapy Mainly Based on α-interferon for metastatic renal cell carcinoma: Relationship Between Antitumor Effectors and Survival Period as seen from Peripheral Blood Lymphocyte Subsets before Treatment" The Japanese Journal of Urology 1995 86(3):636, P41.

Tsujino et al. "Review of Pre-treatment Peripheral Lymphocyte Subsets in Patients with Bladder Cancer" The Japanese Journal of Urology 1997 88 (2):199, O-179.

Shinbu So et al. "Simple Lymphocyte Analytical Formulas to Monitor Change in Immunity" Japanese Journal of Clinical Laboratory Automation 2017 42(4):470, 095.

Kobayashi et al. "Changes of Lymphocyte Subpopulation in Advanced Renal Cell Carcinoma Patients with Marked Response to α-Interferon Therapy" The Japanese journal of Urology 1994 85(9):1380-1387.

Extended European Search Report in EP 18897146.9 dated Dec. 15, 2021.

Bishara et al. "Pre-treatment white blood cell subtypes as prognostic indicators in ovarian cancer" European Journal of Obstetrics and Gynecology and Reproductive Biology 2008 138:71-75.

Nishimura et al. "A New Method to Determine Natural Killer Cell Activity Without Target Cells" http://dx.doi.org/10.5772/intechogen.71912 Chapter 9 2017 pp. 181-197.

* cited by examiner

Fig.3

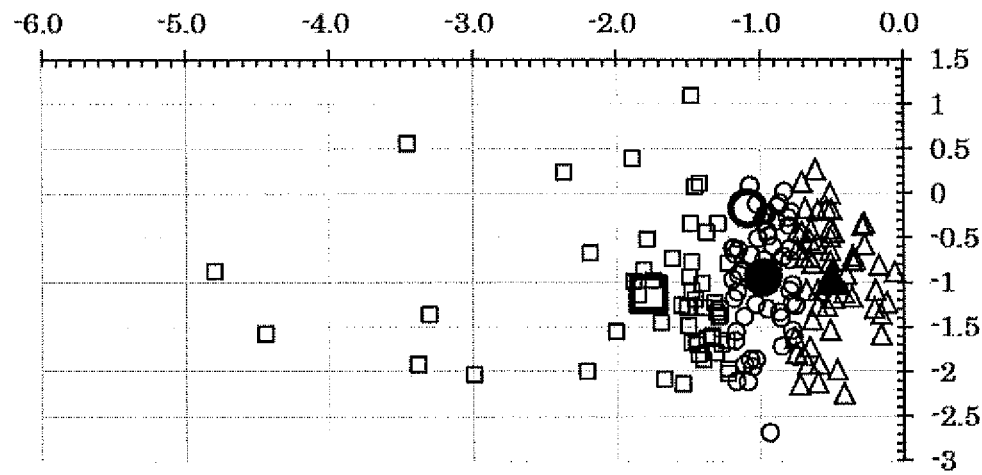

Large White○ : Basic Center of GOOD Group
Large White□ : Average Value of GOOD/Lower X-axis Group (n=54)
Large Black● : Average Value of GOOD/Middle X-axis Group (n=54)
Large Black▲ : Average Value of GOOD/Higher X-axis Group (n=54)
Small White□ : Plotting of GOOD/Lower X-axis Group (n=54)
Small White○ : Plotting of GOOD/Middle X-axis Group (n=54)
Small White△ : Plotting of GOOD/Higher X-axis Group (n=54)

Fig.4

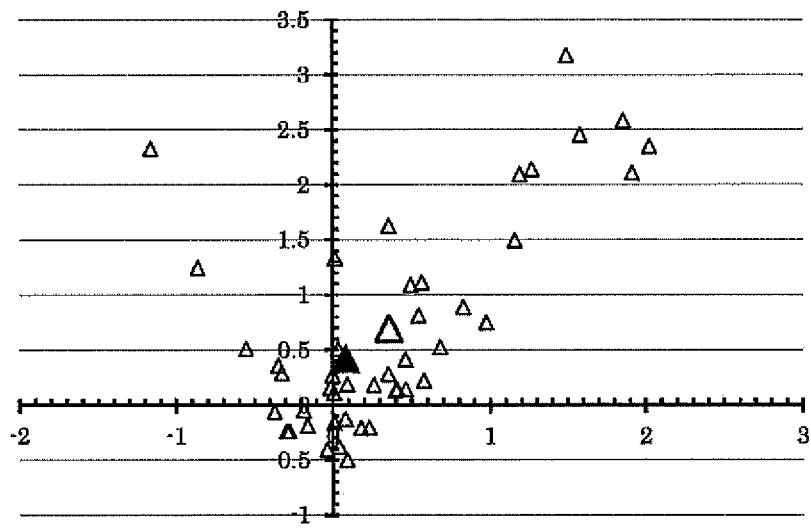

Large Black▲ : Basic Center of Discriminants
Large White△ : Averge Value of 45 Examples
Small White△ : Plotting of 45 Examples < GOOD/Middle X-axis Group n = 2 6 ∕ NK cell >

<GOOD Group n = 2 6 ∕ T-cell Immunity>

< GOOD Group  n = 2 6 / B-cell Immunity >

< GOOD Group  n = 2 6 / Basophil >

<GOOD Group n=26/Eosinophil>

<GOOD Group n=26/Neutrophil>

< MODERATE Group n = 4 5 / NK cell >

< MODERATE Group n = 3 5 / T-cell Immunity >

<BAD/Middle X-axis Group    n = 2 6 ／ T-cell Immunity>

<BAD/Lower X-axis Group    n = 4 5 ／ B-cell Immunity >

<BAD/Middle Y-axis Group n = 4 6 / NKT cell>

<BAD/Higher Y-axis Group n = 4 5 / B-cell Immunity>

< BAD/Lower Y-axis Group n = 4 5 / B-cell Immunity >

< n = 2 9 / T-cell Immunity >

< n = 2 7 / B-cell Immunity >

< n = 2 7 / NKT cell >

⟨ n = 2 7 / NKT cell ⟩

⟨ n = 2 8 / Basophil ⟩

Transition of NK-, Killer- and NKT-activity indices and respective ADCC activity indices, and relapses

METHOD, SYSTEM, AND PROGRAM FOR SUPPLYING IMMUNODYNAMICS-RELATED INFORMATION

TITLE OF THE INVENTION

This patent application is a U.S. National Stage Application of International Application No. PCT/JP2018/047438, filed Dec. 25, 2018, which claims the benefit of priority from Japanese Patent Application No. 2017-249877, filed Dec. 26, 2017, teachings of each of which are herein incorporated by reference in their entirety.

FIELD OF THE INVENTION

The present invention relates to a method of supplying immunodynamics-related information.

BACKGROUND ARTS

Today, due to advance in technology, a variety of therapeutic means have been developed based on anti-tumor immunotherapies. However, a large part of the mechanism of cellular immunity is yet to be clarified, and its relevance in immunotherapy is being groped.

The inventor has previously proposed a method of measuring immunodynamics in blood analysis characterized in measuring antigen recognition function, etc., though the immunocompetent cells that were focused on at that time were not enough to comprehend the entire structure of immunodynamics (Patent Reference 1).

PRIOR ART REFERENCES

Patent References

Patent Reference 1: JP B 2568136

SUMMARY OF THE INVENTION

Problems to be Solved by the Invention

An object of the present invention is to provide immunodynamics-related information that helps an easy comprehension of the immunodynamics of cellular immunity of a subject and can therefore be a guiding principle for therapy and prophylaxis for a disease and/or symptom of the subject.

Means to Solve the Problems

The inventor chose patients with prostate cancer as examples, carried out statistical analyses of cell-counts of immunocompetent cells in subjects' blood, and found out that the cell-counts of immunocompetent cells are associated with prognosis. The inventor further carried on the investigation and found that immunodynamics-related information which helps determination of therapy or prophylaxis for a disease and/or symptom can be obtained by analyzing the cell-counts of immunocompetent cells, and thus completed the invention.

Namely, the present invention relates to:

<1> A method for supplying immunodynamics-related information for use in determining therapy or prophylaxis for a disease and/or symptom of a subject, comprising:

(i) calculating a discriminant score by assigning the cell-count of each of multiple types of immunocompetent cells in blood collected from the subject into a discriminant function;
(ii) determining a group into which the subject is to be sorted by the calculated discriminant score; and
(iii) displaying immunodynamics-related information of the determined group;

wherein:

the discriminant function is obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and the group into which the subject is to be sorted is one of the multiple groups that are divided from the data cluster used for obtaining the discriminant function using discriminant scores as indicator.

<2> The method according to <1> above, wherein the condition of an individual is selected from a group consisting of health, a disease, a disorder, a symptom or prognosis.

<3> The method according to <1> or <2> above, wherein the immunodynamics-related information is obtained by:

(a) performing a multiple regression analysis for data of the cell-counts of n types of immunocompetent cells that constitute one group, wherein one type of immunocompetent cell among the n types of immunocompetent cells is set as an objective variable and n-1 types of immunocompetent cells excluding the one type of immunocompetent cell that is set as the objective variable are set as explanatory variables, and wherein n is an integer of 4 or more;

(b) ranking the n-1 types of immunocompetent cells in descending order according to the magnitude of the absolute value of the standard partial regression coefficient obtained from the multiple regression analysis;

(c) performing a regression analysis in which the one type of immunocompetent cell that is the objective variable in (a) above is set as an objective variable and the immunocompetent cell that is ranked as the first place in (b) above is set as explanatory variable, calculating the contribution ratio $\alpha_1$ which is considered as the influence degree of the first-place ranked immunocompetent cell $\beta_1$; and (d) performing a multiple regression analysis in which the one type of immunocompetent cell that is the objective variable in (a) above is set as an objective variable and m types of immunocompetent cells from the first to the m-th place ranked in (b) above are set as explanatory variables, calculating the contribution ratio $\alpha_m$, and calculating the influence degree $\beta_m$ of the immunocompetent cell ranked as m-th place by the following formula:

$$\beta_3 = \alpha_m - \alpha_{m-1}$$

for each of the immunocompetent cells ranked from the second to the m-th place; wherein m is more than 3 and up to n-1.

<4> The method according to any one of <1> to <3> above, wherein the immunocompetent cells are three or more selected from a group consisting of: Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil.

<5> The method according to <4> above, wherein the immunocompetent cells comprise Th17+ lymphocyte.

<6> The method according to any one of <3> to <5> above, wherein the one type of immunocompetent cell that is set as the objective variable in (a) above is selected from a group consisting of: Tc*DR lymphocyte, CD20*DR lymphocyte, NK cell, NKT cell, basophil, eosinophil and neutrophil.

<7> A method of evaluating NK-cell activity using the influence degree according to any one of <3> to <6> by the following formula:

NK-cell activity index

={[monocyte influence degree (%) calculated using NK cell as an objective variable]×[Act.Th1 lymphocyte influence degree (%) calculated using NK cell as an objective variable]×[Tc*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 μL blood of the data cluster);

provided that, in multiple regression analysis in which NK cell is set as the objective variable, the standard partial regression coefficients of monocyte, Act.Th1 lymphocyte and Tc*DR lymphocyte are all positive.

<8> A method of evaluating NK-cell ADCC (antibody-dependent cellular cytotoxicity) activity using the influence degree according to any one of <3> to <6> by the following formula:

NK-cell ADCC activity index

={[monocyte influence degree (%) calculated using NK cell as an objective variable]×[Act.Th2 lymphocyte influence degree (%) calculated using NK cell as an objective variable]×[CD20*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 μL blood of the data cluster);

provided that, in multiple regression analysis in which NK cell is set as the objective variable, the standard partial regression coefficients of monocyte, Act.Th2 lymphocyte and CD20*DR lymphocyte are all positive.

<9> A method of evaluating NKT-cell activity using the influence degree according to any one of <3> to <6> by the following formula:

NKT-cell activity index

={[monocyte influence degree (%) calculated using NKT cell as the objective variable]×[Act.Th1 lymphocyte influence degree (%) calculated using NKT cell as the objective variable]×[Tc*DR lymphocyte influence degree (%) calculated using NKT cell as the objective variable]÷[the sum of the respective influence degrees (%) of all immunocompetent cells in which the influence degrees are calculated using NKT cell as the objective variable]}×(the average number of NKT cells per 1 μL blood of the data cluster);

provided that, in multiple regression analysis in which NKT cell is set as the objective variable, the standard partial regression coefficients of monocyte, Act.Th1 lymphocyte and Tc*DR lymphocyte are all positive.

<10> A method of evaluating NKT-cell ADCC (antibody-dependent cellular cytotoxicity) activity using the influence degree according to any one of <3> to <6> by the following formula:

NKT-cell ADCC activity index

={[monocyte influence degree (%) calculated using NKT cell as the objective variable]×[Act.Th2 lymphocyte influence degree (%) calculated using NKT cell as the objective variable]×[CD20*DR lymphocyte influence degree (%) calculated using NKT cell as the objective variable]÷[the sum of the respective influence degrees (%) of all immunocompetent cells in which the Influence degrees are calculated using NKT cell as an objective variable]}×(the average number of NKT cells per 1 μL blood of the data cluster);

provided that, in multiple regression analysis in which NKT cell is set as the objective variable, the standard partial regression coefficients of monocyte, Act.Th2 lymphocyte and CD20*DR lymphocyte are all positive.

<11> A method of evaluating killer T-cell activity using the influence degree according to any one of <3> to <6> by the following formula:

killer T-cell activity index

={[monocyte influence degree (%) calculated using Tc*DR lymphocyte as the objective variable]×[Act.Th1 lymphocyte influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 μL. blood of data cluster);

provided that, in multiple regression analysis in which Tc*DR lymphocyte is set as the objective variable, the standard partial regression coefficients of monocyte and Act.Th1 lymphocyte are both positive.

<12> A method of evaluating killer T-cell ADCC (antibody-dependent cellular cytotoxicity) activity using the influence degree according to any one of <3> to <6> by the following formula:

killer T-cell ADCC activity index

={[monocyte influence degree (%) calculated using Tc*DR lymphocyte as the objective variable]×[Act.Th2 lymphocyte influence degree (%) calculated using Tc*DR lymphocyte as the objective variable]×[CD20*DR influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 μL blood of data cluster);

provided that, in multiple regression analysis in which Tc*DR lymphocyte is set as the objective variable, the standard partial regression coefficients of monocyte, Act.Th2 lymphocyte and CD20*DR lymphocyte are all positive.

<13> A system for supplying immunodynamics-related information for use in determining therapy or prophylaxis for a disease and/or symptom of a subject, comprising:

(i) a means to calculate a discriminant score by assigning the cell-count of each of multiple types of immunocompetent cells in blood collected from the subject into a discriminant function;

(ii) a means to determine a group into which the subject is to be sorted by the calculated discriminant score; and (iii) a means to display immunodynamics-related information of the determined group; wherein:

the discriminant function is obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and the group into which the subject is to be sorted is one of the multiple groups that are divided from the data cluster used for obtaining the discriminant function using discriminant scores as indicator.

<14> A program to be run by a computer for supplying immunodynamics-related information for use in determining therapy or prophylaxis for a disease and/or symptom of a subject, comprising:

(I) a step of calculating a discriminant score by assigning the cell-count of each of multiple types of immunocompetent cells in blood collected from the subject into a discriminant function;

(ii) a step of determining a group into which the subject is to be sorted by the calculated discriminant score; and (iii) a step of displaying immunodynamics-related information of the determined group; wherein:

the discriminant function is obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and the group into which the subject is to be sorted is one of the multiple groups that are divided from the data cluster used for obtaining the discriminant function using discriminant scores as indicator.

Effects of the Invention

According to the method of the present invention, immunodynamics-related information of a subject can be obtained from cell-counts of immunocompetent cells in blood of the subject. The immunodynamics-related information can be used as a guiding principle for determining therapy or prophylaxis for a disease and/or symptom depending on the immunodynamics of individual subject. For example, according to the present invention, immunodynamics of the subject's cellular immunity can easily be comprehended, and immunodynamics-related information can be provided which can be used as guiding principle for diagnosis of a disease and/or symptom of a subject, in particular pathology of diseases such as autoimmune diseases (asthma, atopic dermatoses, etc.), genetic diseases which cause immune disorder, diseases related to immunity against organ transplant, cancerous diseases, infectious diseases, diseases related to cellular immunity, and therapy or prophylaxis for these diseases. Moreover, it can be used for controlling the immunity when using an immunosuppressant, and for monitoring immunodynamics related to acute or chronic rejection caused upon an organ transplant.

In specific, by sorting and analyzing data from cases accumulated so far and data of different immunocompetent cells, immunodynamics-related information can be provided for each of the sorted groups. More appropriate information about immunodynamics can be obtained by sorting a subject into a specific group based on cell-count data of the immunocompetent cells obtained from the subject. This can further help determining an appropriate therapy or prophylaxis.

For example, when a multiple regression analysis is to be performed for the counts of 26 different immunocompetent cells in subject's blood, 26 times each of blood drawing and measurement are necessary in order to obtain data to be subjected to the analysis. By sorting the subject into the specific group based on data obtained in advance, an immunodynamics chart for helping determining an appropriate therapy or prophylaxis can be obtained in one blood drawing.

BRIEF DESCRIPTION OF DRAWINGS

FIG. 3 represents a scatter plotting of discriminant scores of 162 cases sorted in GOOD group.

FIG. 4 represents a scatter plotting of discriminant scores of 45 cases sorted in MODERATE group.

DESCRIPTION OF EMBODIMENTS

Figure 1:
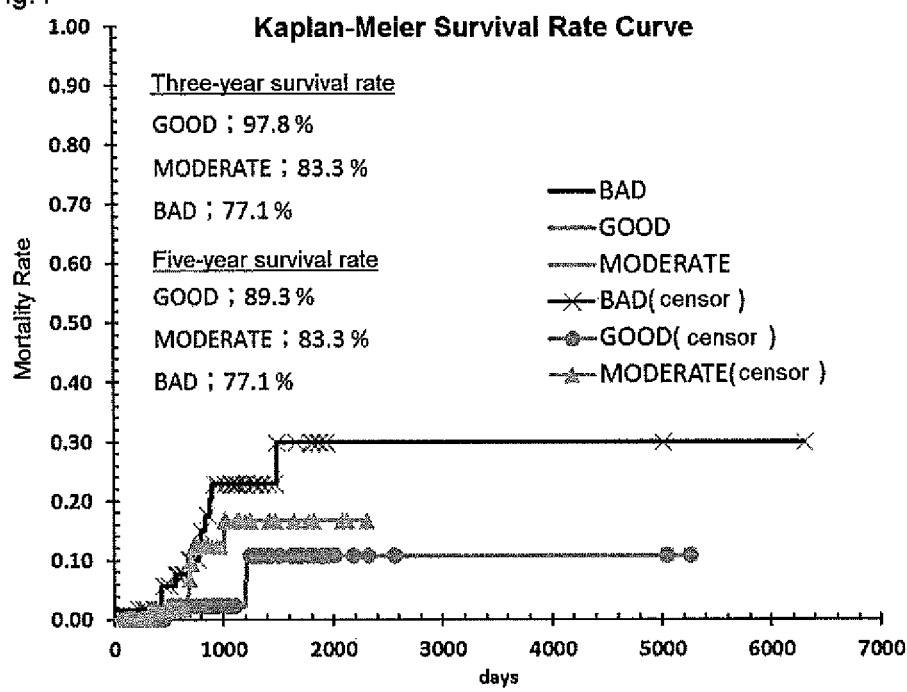
FIG. 1 represents survival rate curves of 59 cases each of GOOD, MODERATE and BAD groups (total 177 cases).

The present invention relates to a method for supplying immunodynamics-related information for use in determining therapy or prophylaxis for a disease and/or symptom of a subject.

In the present invention, a subject may be any living organism, and is preferably a mammal including, for example, a primate such as human and chimpanzee, a rodent such as mouse, rat, guinea pig and hamster, and cattle, camel, goat, sheep, horse, rabbit, dog and cat, and is more preferably, human.

In the present invention, a disease and/or symptom is not particularly limited, but, for example, a disease and/or symptom associated with immunity. More specifically, it includes autoimmune diseases (such as asthma, atopic dermatoses, chronic inflammatory demyelinating polyneuropathy/multifocal motor neuropathy), genetic diseases which cause immune disorder, diseases related to immunity against organ transplant, cancerous diseases, infectious diseases, viral diseases related to cellular immunity (such as serum hepatitis), and amyotrophic lateral sclerosis, etc.

An autoimmune disease includes, such as, e.g., asthma, pollinosis, atopic dermatitis, sarcoidosis, Wegener's granulomatous angiitis, collagen disease overlap syndrome, infertility, pernicious anemia, Guillain-Barre syndrome, myasthenia gravis, chronic gastritis, chronic atrophic gastritis, autoimmune hepatitis, primary biliary cholangitis, ulcerative colitis, Crohn's disease, autoimmune pancreatitis, Takayasu's arteritis, Goodpasture's syndrome, rapidly progressive glomerulonephritis, megaloblastic anemia, autoimmune hemolytic anemia, autoimmune neutropenia, idiopathic thrombocytopenic purpura, Graves' disease (Basedow's disease), Hashimoto's disease (chronic thyroiditis), primary hypothyroidism, idiopathic Addison's disease, type 1 diabetes, insulin-resistant diabetes, chronic discoid lupus erythematosus, localized scleroderma, pemphigus, pustular psoriasis, plaque psoriasis, pemphigoid, herpes gestationis, linear IgA bullous dermatosis, epidermolysis bullosa acquisita, alopecia areata, vitiligo, leukoderma acquisitum centrifugum Sutton/Sutton nevus, Harada disease, autoimmune optic neuropathy, autoimmune inner ear disorder, idiopathic azoospermia, rheumatoid arthritis, systemic lupus erythematosus, antiphospholipid antibody syndrome, polymyositis, dermatomyositis, scleroderma, Sjogren syndrome, IgG4-related disease, vasculitic syndrome, mixed connective tissue disease, familial Mediterranean fever, PAPA syndrome (pyogenic arthritis, pyoderma gangrenosum, and acne), ankylosing spondylitis, giant cell arteritis, cryopyrin-associated periodic syndrome, Crow-Fukase syndrome, polyarteritis nodosa, thrombotic thrombocytopenic purpura, primary immunodeficiency syndrome, microscopic polyangiitis, hyper-IgD syndrome, antiglomerular basement membrane nephritis, eosinophilic gastrointestinal disorder, eosinophilic granulomatosis with polyangiitis, eosinophilic sinusitis, relapsing polychondritis, autoimmune hemorrhaphilia XIII, purpura nephritis, adult-onset Still's disease, systemic juvenile idiopathic arthritis, systemic scleroderma, granulomatosis with polyangiitis, TNF receptor-associated periodic syndrome, Nakajo-Nishimura syndrome, inclusion body myositis, Blau syndrome, Behcet's disease, and chronic inflammatory demyelinating polyneuropathy/multifocal motor neuropathy.

Cancerous diseases are, for example, cancers and sarcomas including, such as, e.g., brain tumor (such as malignant glioma and glioblastoma), lung cancer (adenocarcinoma, squamous cell carcinoma, large cell carcinoma, small cell carcinoma), mediastinal tumor, head and neck cancer such as nasopharyngeal cancer, laryngeal cancer, lingual cancer, oral (mucosal) cancer and gingival cancer; esophageal cancer, gastric cancer, colorectal cancer, rectal cancer, anal cancer, liver cancer (including those originated from hepatic cirrhosis due to hepatitis B or C or other alcoholic or lipogenous hepatic cirrhosis), cancer of gastrointestinal system such as gallbladder/bile duct cancer, pancreatic cancer; gynecologic cancer such as breast cancer, cervical cancer, uterine body cancer, ovarian cancer and endometrial cancer; urogenital cancer such as renal cell carcinoma, ureteropelvic cancer, bladder cancer, prostate cancer, testicular tumor, urethral cancer and penile cancer; osteosarcoma, soft tissue leiomyosarcoma, rhabdomyosarcoma, malignant melanoma, skin cancer; leukemia such as adult T-cell leukemia, Epstein-Barr virus infection (infectious mononucleosis, Burkitt's lymphoma, some nasopharyngeal cancers), Hodgkin's lymphoma and hairy cell leukemia, and hematologic diseases such as malignant lymphoma.

Infectious diseases include, such as, e.g., viral infection, bacterial infection, fungal infection, protozoan parasite infection and helminthic parasite infection.

Viral infections include, such as, e.g., common cold, norovirus infection, rotavirus infection, influenza virus infection, viral hepatitis, viral meningitis, acquired immunodeficiency syndrome (AIDS), adult T-cell leukemia, Ebola hemorrhagic fever, yellow fever, common cold syndrome, rabies, cytomegalovirus infection, severe acute respiratory syndrome (SARS), progressive multifocal leukoencephalopathy, chickenpox/herpes zoster, herpes simplex, hand-foot-and-mouth disease, dengue fever, erythema infectiosum, infectious mononucleosis, smallpox, rubella, acute anterior poliomyelitis (polio), measles, pharyngoconjunctival fever (pool fever), Marburg hemorrhagic fever, hantavirus renal hemorrhagic fever, Lassa fever, South American hemorrhagic fever, Middle East respiratory syndrome (MERS), mumps, West Nile fever, herpangina, chikungunya fever.

Bacterial infection include a variety of infections by, such as, e.g., *Streptococcus* (e.g., Group Aβ hemolytic *streptococcus, Streptococcus pneumoniae*), *Staphylococcus aureus* (MSSA, MRSA), *Staphylococcus epidermidis, Enterococcus, Listeria, Neisseria meningitidis, Neisseria gonorrhoeae*, pathogenic *Escherichia coil* (e.g., O157:H7), *Klebsiella (Klebsiella pneumoniae), Proteus, Bordetella pertussis, Pseudomonas aeruginosa, Serratia, Citrobacter, Acinetobacter, Enterobacter, Mycoplasma, Clostridium,* and tuberculosis, cholera, plague, diphtheria, dysentery, scarlet fever, anthrax, syphilis, tetanus, Hansen's disease, Legionella pneumonia, leptospirosis, Lyme disease, tularemia and Q-fever.

In the present invention, therapy can be any therapy known for the disease or symptom, and may be, without being particularly limited, for example, a therapy that utilizes immune function such as immune checkpoint inhibitor therapy, cytokine therapy, cell adoptive immunity therapy (e.g., αβT cell, γδT cell, NK cell and NKT cell), regenerative immunotherapy with IPS cells and genetically modified T cell therapy (CAR-T: Chimeric Antigen Receptor T-cell Therapy).

In the present invention, prophylaxis can be any prophylaxis known for the disease or symptom, and may be, without being particularly limited, for example, a prophylaxis that enhances immune function by an intake or administration of an useful substance. The useful substances include, for example, fungus such as Agaricus, Reishi, Polyporaceae (Hoelen), Cordyceps, Shiitake mushroom, Shiitake mushroom extract, AHCC (Active Hexose Correlated Compound)® or a functional food, extract or supplement made of fungus; Chinese herbal medicines such as juzen-taiho-to, hochu-ekki-to and sairei-to; lipid-lowering drug; supplements such as vitamins such as vitamin D3.

In the present invention, immunodynamics-related information is information for determining whether different immunocompetent cells are coordinately functioning or whether their differentiation and proliferation is stagnated/ inhibited, and it means, for example, information about analyses of the degree or condition of the correlation between different immunocompetent cells.

More specifically, information is about analyses of the degree of coordination to, e.g., Tc*DR lymphocyte, CD20*DR lymphocyte, NK cell, NKT cell, basophil, eosinophils or neutrophils by other immunocompetent cells. Moreover, immunodynamics-related information can be expressed as an immunodynamics chart. By being expressed as an immunodynamics chart, the condition of immunodynamics will more easily be determined or understood. Such information is extremely useful in determining the immunocompetent cell to be targeted or the correlation between immunocompetent cells for therapy or prophylaxis of a disease or symptom.

In the present invention, the degree of coordination is expressed, for example, by a influence degree (the area of a circle in an immunodynamics chart) or by either positive or negative value of the partial regression coefficient (a type of arrow in the immunodynamics chart).

The method for supplying immunodynamics-related information of the present invention, in one embodiment, comprises:
(i) calculating a discriminant score by assigning the cell-count of each of multiple types of immunocompetent cells in blood collected from the subject into a discriminant function;
(ii) determining a group into which the subject is to be sorted by the calculated discriminant score; and
(iii) displaying immunodynamics-related information of the determined group.

Here, the discriminant function can be obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set as an objective variable, and the multiple types of immunocompetent cells are set as explanatory variables.

In the present invention, the condition of an individual is such as, e.g., health, a disease, a disorder, a symptom or prognosis of an individual. The condition of an individual can be typified according to the necessity. It is typified, for example, by degree of health, degree of symptoms, type or degree of the disease, type or degree of the disorder, and degree of the prognosis. Typification can also be, for example, classification by the values of biomarkers, by disease stages, by the rate of complete remission, by survival rate such as three-year or five-year survival rate.

In the present invention, the number of individuals is any number. For example, a plurality of data can be obtained from one individual.

Moreover, the group into which the subject is to be sorted is one of the multiple groups that are divided from the data cluster used for obtaining the discriminant function using discriminant scores as indicator.

In the present invention, a discriminant analysis encompasses a discriminant analysis which involves two groups of objective variables, as well as a multiple discriminant analysis or canonical discriminant analysis which involves three or more groups of objective variables.

In the present invention, a data cluster means a cluster of data which comprises at least data of the condition of an individual and data of the cell-counts of multiple immunocompetent cells in blood collected from the individual, and the data cluster comprises such data in a number that allows for the discriminant analysis. Here, the number that allows for the discriminant analysis is a number which exceeds the number of explanatory variables by at least one in the discriminant analysis. The data cluster can be divided into multiple groups using the discriminant score as an indicator.

In the present invention, an immunocompetent cell means any cell which is in charge of immune response, and includes, such as, without being particularly limited, e.g., a leukocyte, monocyte, basophil, eosinophil, neutrophil, CD3-positive lymphocyte (CD3), CD4-positive lymphocyte (CD4), CD8-positive lymphocyte (CD8), CD20*DR lymphocyte (CD20*DR), Ti lymphocyte (inducer T cell; Ti), Ti−2 lymphocyte (Ti−2), Ti± lymphocyte (Ti±), Ti+2 lymphocyte (Ti+2), Th lymphocyte (helper T cell; Th), Th1 lymphocyte (helper Th1 lymphocyte; helper Th1 cell; Th1), Th2 lymphocyte (helper Th2 lymphocyte; helper Th2 cell; Th2), Th−2 lymphocyte (Th−2), Th± lymphocyte (Th±), Th+2 lymphocyte (Th+2), Th17+ lymphocyte (Th17+), Ts lymphocyte (suppressor T cell; Ts), Ts− lymphocyte (Ts−), Ts+ lymphocyte (Ts+), Tc lymphocyte (cytotoxic T cell; Tc), Tc− lymphocyte (Tc−), Tc+ lymphocyte (Tc+), Act.s/cT lymphocyte (activated suppressor/cytotoxic T cell; Act.s/cT), Ts*DR lymphocyte (activated suppressor T cell; Ts*DR), Tc*DR lymphocyte (activated cytotoxic T cell; Tc*DR), Act.i/hT lymphocytes (activated inducer/helper T cell; activated inducer/helper T cell; Act.i/hT), Th*DR (activated helper T cell; activated helper T cell; Th *DR), Ti*DR lymphocyte (activated inducer T cell; Ti*DR), Act.Th1 lymphocyte (activated helper Th1 cell; Act.Th1), Act.Th2 lymphocyte (activated helper Th2 cell; Act.Th2), NK cell (natural killer cell; NK), NKT cell (natural killer T cell; NKT) and N3+ cell (N3+). For any one of the immunocompetent cells described above, the abbreviation described in parentheses may be used.

In the present invention, the cell-count of an immunocompetent cell can be counted or calculated according to a conventional method.

For instance, the number of leukocytes, lymphocytes, monocyte, basophil, eosinophils or neutrophils can be counted to I digit of real number by subjecting the blood drawn from the subject to a general automatic hemocyte counting apparatus. The unit is, for example, in cells/cubic millimeter ($mm^3=\mu L$).

Lymphocytes are single- or multi-stained for the abundance ratio of various cell-surface markers such as, e.g., CD3, CD4, CD8, CD11b, CD16, CD20, CD25, CD45RA, CD56, CD122, CD161, FoxP3, HLA-DR, IFNγ and IL-4 using antibodies, and measured by flow-cytometry.

The lymphocytes are defined as described below by the combination of various cell-surface markers such as, e.g., CD3, CD4, CD8, CD11b, CD16, CD20, CD25, CD45RA, CD56, CD122, CD161, FoxP3, HLA-DR, IFNγ and IL-4.

A CD3-positive lymphocyte means a lymphocyte which is CD3-positive. This is similar for representation such as a CD4-positive or CD8-positive lymphocyte.

The number of CD3-positive lymphocytes can be calculated, for example, by multiplying either the percentage of CD3-positives in the result of a double-staining flow-cytometry analysis for CD3 and CD161 (i.e., the sum of the percentage of [CD3-positive and CD161-negative] plus the percentage of [CD3-positive and CD161-positive]) or the percentage of CD3-positives in the result of a quadruple-staining flow-cytometry analysis for CD11b, CD122, CD3 and CD8 by the number of lymphocytes. For instance, the values of these may be compared to adopt smaller value.

The number of CD4-positive lymphocytes can be calculated, for example, by using either of the percentage of CD4-positives in the result of a double-staining flow-cytometry analysis for HLA-DR and CD4 (i.e., the sum of the percentage of [CD4-positive and KA-DR-negative] and the percentage of [CD4-positive and HLA-DR-positive]) or the percentage of CD4-positives in the result of a quadruple-staining flow-cytometry analysis for CD45RA, FoxP3, CD4 and CD25, and multiplying this by the number of lymphocytes. For instance, the values of these may be compared to adopt smaller value.

The number of CD8-positive lymphocytes can be calculated, for example, by multiplying the percentage of CD8-positives in the result of a double-staining flow-cytometry analysis for HLA-DR and CD8 (i.e., the sum of the percentage of [CD8-positive and HLA-DR-negative] and the percentage of [CD8-positive and HLA-DR-positive]) by the number of lymphocytes.

CD20*DR lymphocyte means a lymphocyte that is CD20-positive and HLA-DR-positive.

The number of CD20*DR lymphocytes can be calculated, for example, by multiplying the percentage of [CD20-positive and HLA-DR-positive] in the result of a double-staining flow-cytometry analysis for HLA-DR and CD20 by the number of lymphocytes.

Ti lymphocyte (inducer T cell) means a lymphocyte that is CD4-positive and CD45RA-positive.

The number of Ti lymphocytes can be calculated, for example, by multiplying the percentage of [CD4-positive and CD45RA-positive] in the result of a quadruple-staining flow-cytometry analysis for CD45RA, FoxP3, CD4 and CD25 by the number of lymphocytes.

Ti−2 lymphocyte means a lymphocyte that is CD4-positive, CD45RA-positive, CD25-negative, and FoxP3-negative.

The number of Ti−2 lymphocytes can be calculated, for example, by multiplying the percentage of [CD4-positive and CD45RA-positive] and the percentage of [CD4-positive, CD45RA-positive, CD25-negative and FoxP3-negative] in the result of a quadruple-staining flow-cytometry analysis for CD45RA, FoxP3, CD4 and CD25, and multiplying this by the number of lymphocytes.

Ti± lymphocyte means a lymphocyte that is CD4-positive, CD45RA-positive, CD25-positive, and FoxP3-negative.

The number of Ti± lymphocytes can be calculated, for example, by multiplying the percentage of [CD4-positive and CD45RA-positive] and the percentage of [CD4-positive, CD45RA-positive, CD25-positive and FoxP3-negative] in the result of a quadruple-staining flow-cytometry analysis for CD45RA, FoxP3, CD4 and CD25, and multiplying this by the number of lymphocytes.

Ti+2 lymphocyte means a lymphocyte that is CD4-positive, CD45RA-positive, CD25-positive, and FoxP3-positive.

The number of Ti+2 lymphocytes can be calculated, for example, by multiplying the percentage of [CD4-positive and CD45RA-positive] and the percentage of [CD4-positive, CD45RA-positive, CD25-positive and FoxP3-positive] in the result of a quadruple-staining flow-cytometry analysis for CD45RA, FoxP3, CD4 and CD25, and multiplying this by the number of lymphocytes.

Th lymphocyte (helper T cell) means a lymphocyte that is CD4-positive, and CD45RA-negative.

The number of Th lymphocytes can be calculated, for example, by multiplying the percentage of [CD4-positive and CD45RA-negative] in the result of a quadruple-staining flow-cytometry analysis for CD45RA, FoxP3, CD4 and CD25 by the number of lymphocytes.

Th1 lymphocyte (helper Th1 lymphocyte; helper Th1 cell) means a lymphocyte that is CD4-positive, CD45RA-negative, IFNγ-positive, and IL-4-negative.

The number of Th1 lymphocytes can be calculated by multiplying the number of Th lymphocytes by, e.g., the percentage of [CD4-positive, IFNγ-positive and IL-4-negative] in the results of triple staining analysis by flow-cytometry for CD4, IFNγ and IL-4.

Th2 lymphocyte (helper Th2 lymphocyte; helper Th2 cell) means a lymphocyte that is CD4-positive, CD45RA-negative, IFNγ-negative, and IL-4-positive.

The number of Th2 lymphocytes can be calculated, for example, by multiplying the number of Th lymphocytes by the percentage of [CD4-positive, IFNγ-negative and IL-4-positive] in the results of triple staining analysis by flow-cytometry for CD4, IFNγ and IL-4.

Th−2 lymphocyte means a lymphocyte that is CD4-positive, CD45RA-negative, CD25-negative, and FoxP3-negative.

The number of Th−2 lymphocytes can be calculated, for example, by multiplying the percentage of [CD4-positive and CD45RA-negative] and the percentage of [CD4-positive, CD45RA-negative, CD25-negative and FoxP3-negative] in the result of a quadruple-staining flow-cytometry analysis for CD45RA, FoxP3, CD4 and CD25, and multiplying this by the number of lymphocytes.

Th± lymphocyte means a lymphocyte that is CD4-positive, CD45RA-negative, CD25-positive, and FoxP3-negative.

The number of Th± lymphocytes can be calculated, for example, by multiplying the percentage of [CD4-positive and CD45RA-negative] and the percentage of [CD4-positive, CD45RA-negative, CD25-positive and FoxP3-negative] in the result of a quadruple staining flow-cytometry analysis for CD45RA, FoxP3, CD4 and CD25, and multiplying this by the number of lymphocytes.

Th+2 lymphocyte means a lymphocyte that is CD4-positive, CD45RA-negative, CD25-positive, and FoxP3-positive.

The number of Th+2 lymphocytes can be calculated, for example, by multiplying the percentage of [CD4-positive and CD45RA-negative] and the percentage of [CD4-positive, CD45RA-negative, CD25-positive and FoxP3-positive] in the result of a quadruple-staining flow-cytometry analysis for CD45RA, FoxP3, CD4 and CD25, and multiplying this by the number of lymphocytes.

Th17+ lymphocyte means a lymphocyte that is CD4-positive, IFNγ-positive and IL-17-positive.

The number of Th17+ lymphocytes can be calculated, for example, by multiplying the percentage of [IFNγ-positive and IL-17-positive] in the results of triple staining analysis by flow-cytometry for IFNγ, CD4 and IL-17 by the number of CD4 lymphocytes.

Act.i/h T lymphocytes (Activated inducer/helper T Cell) means a lymphocyte that is CD4-positive and HLA-DR-positive.

The number of Act.i/h T lymphocytes can be calculated, for example, by multiplying the percentage of [CD4-positive and HLA-DR-positive] in the result of a double-staining flow-cytometry analysis for HLA-DR and CD4 by the number of lymphocytes.

The number of Ti*DR lymphocytes (Activated inducer T cell) can be calculated, for example, by multiplying Act.i/h T lymphocytes and the number of Ti lymphocytes/(the number of Th lymphocytes+the number of Ti lymphocytes).

The number of Th*DR lymphocytes (Activated helper T cells) can be calculated, for example, by multiplying the number of Act.i/h T lymphocytes by [the number of Th lymphocytes÷(the number of Th lymphocytes+the number of Ti lymphocytes)].

The number of Act.Th1 lymphocytes can be calculated, for example, by multiplying the number of Th*DR lymphocytes by [the number of TH1 lymphocytes÷(the number of Th1 lymphocytes+the number of Th2 lymphocytes)].

The number of Act.Th2 lymphocytes can be calculated, for example, by multiplying the number of Th*DR lymphocytes by [the number of Th2 lymphocytes÷(the number of Th1 lymphocytes+the number of Th2 lymphocytes)].

Ts lymphocyte (Suppressor T cell) means a lymphocyte that is CD8-positive and CD11b-positive.

The number of Ts lymphocytes can be calculated, for example, by multiplying the percentage of [CD8-positive and CD11 b-positive] in the result of a quadruple-staining flow-cytometry analysis for CD11b, CD122, CD3 and CD8 by the number of lymphocytes.

Ts− lymphocyte means a lymphocyte that is CD8-positive, CD11b-positive and CD122-negative. The number of Ts− lymphocytes can be calculated, for example, by multiplying the percentage of [CD8-positive and CD11b-positive] and the percentage of [CD11b-positive and CD122-negative] in the result of a quadruple-staining flow-cytometry analysis for CD11b, CD122, CD3 and CD8, and multiplying this by the number of lymphocytes.

Ts+ lymphocyte means a lymphocyte that is CD8-positive, CD11b-positive and CD122-positive.

The number of Ts+ lymphocytes can be calculated, for example, by multiplying the percentage of [CD8-positive and CD11b-positive] and the percentage of [CD11b-positive and CD122-positive] in the result of a quadruple-staining flow-cytometry analysis for CD11b, CD122, CD3 and CD8, and multiplying this by the number of lymphocytes.

Tc lymphocyte (Cytotoxic T cell) means a lymphocyte that is CD8-positive and CD11b-negative.

The number of Tc lymphocytes can be calculated, for example, by multiplying the percentage of [CD8-positive and CD11b-negative] in the result of a quadruple-staining flow-cytometry analysis for CD11b, CD122, CD3 and CD8 by the number of lymphocytes.

Tc− lymphocyte means a lymphocyte that is CD8-positive, CD11b-negative, and CD122-negative.

The number of Tc− lymphocytes can be calculated, for example, by multiplying the percentage of [CD8-positive and CD11b-negative] and the percentage of [CD11b-negative and CD122-negative] in the result of a quadruple-staining flow-cytometry analysis for CD11b, CD122, CD3 and CD8, and multiplying this by the number of lymphocytes.

Tc+ lymphocyte means a lymphocyte that is CD8-positive, CD11b-negative, and CD122-positive. The number of Tc+ lymphocytes can be calculated, for example, by multiplying the percentage of [CD8-positive and CD11b-negative] and the percentage of [CD11b-negative and CD122-positive] in the result of a quadruple-staining flow-cytometry analysis for CD11b, CD122, CD3 and CD8, and multiplying this and the number of lymphocytes.

The number of Act.s/cT lymphocytes (Activated suppressor/cytotoxic T cells) can be calculated, for example, by multiplying the percentage of [CD8-positive and HLA-DR-positive] in the result of a double-staining flow-cytometry analysis for HLA-DR and CD8 by the number of lymphocytes.

The number of Ts*DR lymphocytes (Activated suppressor T Cells) can be calculated, for example, by multiplying the number of Act.s/cT lymphocytes by [the number of Ts lymphocytes÷(the number of Tc lymphocytes+the number of Ts lymphocytes)].

The number of Tc*DR lymphocytes (Activated cytotoxic T cells) can be calculated, for example, by multiplying the number of Act.s/cT lymphocytes by [the number of To lymphocytes÷(the number of Tc lymphocytes+the number of Ts lymphocytes)].

NK cell (Natural killer Cell) means a lymphocyte that is CD16-positive and CD56-positive.

The number of NK cells can be calculated, for example, by multiplying the percentage of [CD16-positive and CD56-positive] in the results of triple staining analysis by flow-cytometry for CD16, CD161 and CD56 by the number of lymphocytes.

NKT cells (Natural killer T cell) means a lymphocyte that is CD3-positive and CD161-positive.

The number of NKT cells can be calculated, for example, by multiplying the percentage of [CD3-positive and CD161-positive] in the result of a double-staining flow-cytometry analysis for CD3 and CD161 by the number of lymphocytes.

N3+ cell means a lymphocyte that is CD16-positive, CD161-positive and CD56-positive. The number of N3+ cell can be calculated, for example, by multiplying the percentage of [CD16-positive, CD161-positive and CD56-positive] in the results of triple staining analysis by flow-cytometry for CD16, CD161 and CD56 by the number of lymphocytes.

In one embodiment of the present invention, the multiple types of immunocompetent cells are three or more selected from a group consisting of, e.g., Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophils, neutrophil, Th1 lymphocyte, Th2 lymphocyte, Ti lymphocyte, Tc lymphocyte, Ts lymphocyte, Act.i/h T lymphocytes and Act.s/cT lymphocyte.

In one embodiment of the present invention, the multiple types of immunocompetent cells are three or more selected from a group consisting of, e.g., Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti±−lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+cell, monocyte, basophil, eosinophil and neutrophil.

In one embodiment of the present invention, the multiple types of immunocompetent cells comprise, e.g., Th17+ lymphocyte.

In one embodiment of the present invention, the multiple types of immunocompetent cells are 17 types consisting of: CD3-positive lymphocyte, CD4-positive lymphocyte, CD8-positive lymphocyte, CD20*DR lymphocyte, Th1 lymphocyte, Th2 lymphocyte, Ti lymphocyte, Tc lymphocyte, Ts lymphocyte, Act.i/h T lymphocyte, Act.s/c T lymphocyte, NK cell, N3+cell, monocyte, basophil, eosinophil and neutrophil.

In one embodiment of the present invention, preferably the multiple types of immunocompetent cells are 26 types consisting of: CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil.

In one embodiment of the present invention, more preferably the multiple types of immunocompetent cells are 27 types consisting of: Th17+ lymphocyte, CD3-positive lymphocyte, CD4-positive lymphocyte, CD8-positive lymphocyte, CD20*DR lymphocyte, Th−± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil.

In the present invention, immunodynamics-related information is obtained, for example, by the following (a) to (d), without being particularly limited:

(a) performing a multiple regression analysis for data of the cell-counts of n types of immunocompetent cells that constitute one group, wherein one type of immunocompetent cell among the n types of immunocompetent cells is set as an objective variable, and n-1 types of immunocompetent cells excluding the one type of immunocompetent cell that is set as the objective variable as explanatory variables, and wherein n is an integer of 4 or more;

(b) ranking the n-1 types of immunocompetent cells in descending order according to the magnitude of the absolute value of the standard partial regression coefficient obtained from the multiple regression analysis;

(c) performing a regression analysis in which the one type of immunocompetent cell that is the objective variable in (a) above is set as an objective variable and the immunocompetent cell that is ranked as the first place in (b) above is set as explanatory variable, calculating the contribution ratio $\alpha_1$ which is considered as the influence degree of the first-place ranked immunocompetent cell $\beta_1$; and (d) performing a multiple regression analysis in which the one type of immunocompetent cell that is the objective variable in (a) above is set as an objective variable and m types of immunocompetent cells from the first to the m-th place ranked in (b) above are set as explanatory variables, calculating the contribution ratio $\alpha_m$, and calculating the influence degree $\beta_m$ of the immunocompetent cell ranked as m-th place by the following formula:

$$\beta_m = \alpha_m \alpha_{m-1}$$

for each of the immunocompetent cells ranked from the second to the m-th place; wherein m is more than 3 and up to n-1.

In the present invention, regression analysis not only encompasses a single regression analysis which involves one explanatory variable, but also encompasses a multiple regression analysis which involves two or more explanatory variables. Moreover, in the present invention, the description "performing multiple regression analyses repeatedly" may include embodiments in which the repeated regression analyses include a single regression analysis which involves one explanatory variable.

In the present invention, when performing a multiple regression analysis, a constant term may or may not be provided. Preferably, in the present invention, when performing a multiple regression analysis, no constant term is provided.

In the present invention, without performing a discriminant analysis, immunodynamics-related information can be obtained by performing regression analysis as described above on data of cell-counts of n types of immunocompetent cells which constitute the desired group.

In one embodiment of the present invention, the one type of immunocompetent cell that is set as the objective variable in (a) above can be selected from a group consisting of, e.g., Tc*DR lymphocyte, CD20*DR lymphocyte, NK cell, NKT cell, basophil, eosinophil and neutrophil.

The present invention, in one aspect, relates to a system for supplying immunodynamics-related information for use in determining therapy or prophylaxis for a disease and/or symptom of a subject.

The system comprises, for example:
(i) a means to calculate a discriminant score by assigning the cell-count of each of multiple types of immunocompetent cells in blood collected from the subject into a discriminant function;
(ii) a means to determine a group into which the subject is to be sorted by the calculated discriminant score; and
(iii) a means to display immunodynamics-related information of the determined group;
wherein:
the discriminant function is obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and
the group into which the subject is to be sorted is one of the multiple groups that are divided from the data cluster used for obtaining the discriminant function using discriminant scores as indicator.

The present invention, in one aspect, relates to a program to be run by a computer for supplying immunodynamics-related information for use in determining therapy or prophylaxis for a disease and/or symptom of a subject.

The program comprises, for example:
(i) a step of calculating a discriminant score by assigning the cell-count of each of multiple types of immunocompetent cells in blood collected from the subject into a discriminant function;
(ii) a step of determining a group into which the subject is to be sorted by the calculated discriminant score; and
(iii) a step of displaying immunodynamics-related information of the determined group; wherein:
the discriminant function is obtained by performing a discriminant analysis for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and
the group into which the subject is to be sorted is one of the multiple groups that are divided from the data cluster used for obtaining the discriminant function using discriminant scores as indicator.

The present invention, in one aspect, immunodynamics-related information can be provided as an immunodynamics chart. By representing in an immunodynamics chart, the immunodynamics can generally be understood and evaluated. In the present invention, an immunodynamics chart can be generated based on immunodynamics-related information, for example, influence degrees of different immunocompetent cells.

In specific, examples include the immunodynamics charts shown in FIGS. 6-40. The arrangement of various immunocompetent cells and arrows has been determined based on the process of differentiation and maturation of the immunocompetent cells and their interrelationships.

In order to draw a clear immunodynamics chart, for example, the area of a circle indicating an immunocompetent cell can be made proportional to the percentage (%) of the influence degree of the immunocompetent cell. Moreover, when the percentage of the influence degree (%) of immunocompetent cell is less than 0.00785%, the immunocompetent cell can be represented by X and when the percentage of the influence degree (%) of immunocompetent cell is or more 0.00785% and less than 0.0314%, the immunocompetent cell can be represented by ●. Moreover, the line weight of the enclosing line can be made 1.0 pt when the percentage of the influence degree (%) of a immunocompetent cell is less than 0.5%; 1.5 pt when the percentage of the influence degree (%) of a immunocompetent cell is 0.5% or more and less than 1%; 2.5 pt when the percentage of the influence degree (%) of a immunocompetent cell is 1% or more and less than 5%; and 3.0 pt when the percentage of the influence degree (%) of a immunocompetent cell is 5% or more.

Types of arrows and their meanings are as described in Table 1. The type of an arrow is determined by the interrelationship of immunocompetent cells (a relationship on the differentiation pathway, or a suppressing, facilitating or interacting relationship) and by whether the partial regression coefficient value of the immunocompetent cell obtained by the multiple regression analysis is either positive or negative. For example, when the partial regression coefficient of an immunocompetent cell that is to be explanatory variable is positive against that of an immunocompetent cell used as objective variable (i.e., Tc*DR lymphocyte, CD20*DR lymphocyte, NK cell, NKT cell, basophil, eosinophil or neutrophil), the relationship is active and an open white arrow will be applied. When the partial regression coefficient is negative, the relationship is inactive and a closed black arrow will be applied.

In an immunodynamics chart directed to Tc*DR, CD20*DR lymphocyte is in active or inactive interrelationship with Tc*DR; in an immunodynamics chart directed to NK cell, Tc*DR lymphocyte, CD20*DR lymphocyte and Ti*DR lymphocyte are in active or inactive interrelationships with NK cell; in an immunodynamics chart directed to NKT cell, Tc*DR lymphocyte, CD20*DR lymphocyte and N3+ cell are in active or inactive interrelationships with NKT cell; in an immunodynamics chart directed to CD20*DR lymphocyte, Tc*DR lymphocyte is in active or inactive interrelationship with CD20*DR lymphocyte; in an immunodynamics chart directed to basophil, Tc*DR lymphocyte and Act.Th2 lymphocyte are in active or inactive interrelationships with basophil; in an immunodynamics chart directed to eosinophil, Tc*DR lymphocyte and CD20*DR lymphocyte are active or inactive interrelationships with eosinophils; in an immunodynamics chart directed to neutrophil, Th17+ lymphocyte, Tc*DR lymphocyte and CD20*DR lymphocyte are in active or inactive interrelationship with neutrophil.

In order to draw a clear immunodynamics chart, the line width of an arrow can be 6 pt when the percentage of the influence degree (%) of a immunocompetent cell is less than 0.1%; 8 pt when the percentage of the influence degree (%) of a immunocompetent cell is or more 0.1% and less than 0.5%; 10 pt when the percentage of the influence degree (%) of a immunocompetent cell is 0.5% or more and less than 1.0%; 12 pt when the percentage of the influence degree (%) of a immunocompetent cell is 1.0% or more and less than 5.0%; and 14 pt when the percentage of the influence degree (%) of a immunocompetent cell is 5.0% or more.

TABLE 1

| Type of Arrow | Meaning |
| --- | --- |
| ⇒ | Active differentiation pathway |
| ➡ | Inactive differentiation pathway |
| ⇛ | Active suppressing effect |
| ➡● | Inactive suppressing effect |
| ⇒ | Active facilitating effect |
| ➡ | Inactive facilitating effect |
| ⇔ | Active interaction |
| ⬌ | Inactive interaction |

In an immunodynamics chart directed to Tc*DR, Monocyte->Act.Th1->Tc*DR pathway is termed "T-cellular Antigen Recognition Mechanism" (TARM), which is also termed "killer cell activity". Monocyte->Act.Th2->CD20*DR pathway is termed "B-cellular Antigen Recognition Mechanism" (BARM). If Monocyte->Act.Th2->CD20*DR<=>Tc*DR pathway has been established, antibody-dependent cellular cytotoxicity (ADCC) of killer T-cell will be in effect.

In an immunodynamics chart directed to NK cell, Monocyte->Act.Th1->Tc*DR<=>NK pathway is termed NK activity, whereas Monocyte->Act.Th2->CD20*DR<=>NK pathway is termed NK-cell ADCC activity.

In an immunodynamics chart directed to NKT cell, Monocyte->Act.Th1->Tc*DR<=>NKT pathway is termed NKT activity, whereas Monocyte->Act.Th2->CD20*DR<=>NKT pathway is termed NKT-cell ADCC activity.

In one aspect of the present invention, immunodynamics-related information can be used to calculate, e.g., NK activity index (NK Cell Activity Index: NK-AI), ADCC activity index of NK (NK Cell Antibody Dependent Cellular Cytotoxicity Activity Index: NK-ADCC-AI), NKT activity index (NKT Cell Activity Index: NKT-AI), ADCC activity index of NKT (NKT Cell Antibody Dependent Cellular Cytotoxicity Activity Index: NKT-ADCC-AI), killer T-cell activity index (Activated Cytotoxic T Cell Activity index) (Killer T Cell Activity Index: Killer-AI), killer T-cell ADCC activity index (Killer T Cell Antibody Dependent Cellular Cytotoxicity Activity Index: Killer-ADCC-AI). These indices can be used as indicator of immunodynamics, and are, in general, preferred at higher values. Moreover, using these indices, it is possible to predict the degree of tumor mass which can be destructed by an immunocytic therapy.

The indices described above are calculated by following formulae:

NK-cell activity index

= {[monocyte influence degree (%) calculated using NK cell as an objective variable]×[Act.Th1 lymphocyte influence degree (%) calculated using NK cell as an objective variable]×[Tc*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 μL blood of the data cluster)

NK-cell ADCC activity index

= {[monocyte influence degree (%) calculated using NK cell as an objective variable]×[Act.Th2 lymphocyte influence degree (%) calculated using NK cell as an objective variable]×[CD20*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 μL blood of the data cluster)

NKT-cell activity index

= {[monocyte influence degree (%) calculated using NKT cell as the objective variable]×[Act.Th1 lymphocyte influence degree (%) calculated using NKT cell as the objective variable]×[Tc*DR lymphocyte influence degree (%) calculated using NKT cell as the objective variable]÷[the sum of the respective influence degrees (%) of all immunocompetent cells in which the influence degrees are calculated using NKT cell as the objective variable]}×(the average number of NKT cells per 1 μL blood of the data cluster)

NKT-cell ADCC activity index

= {[monocyte influence degree (%) calculated using NKT cell as the objective variable]×[Act.Th2 lymphocyte influence degree (%) calculated using NKT cell as the objective variable]×[CD20*DR lymphocyte influence degree (%) calculated using NKT cell as the objective variable]÷[the sum of the respective influence degrees (%) of all immunocompetent cells in which the influence degrees are calculated using NKT cell as an objective variable]}×(the average number of NKT cells per 1 μL blood of the data cluster)

Killer T-cell activity index

= {[monocyte influence degree (%) calculated using Tc*DR lymphocyte as the objective variable]×[Act.Th1 lymphocyte influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 μL blood of data cluster)

Killer T-cell ADCC activity index
={[monocyte influence degree (%) calculated using Tc*DR lymphocyte as the objective variable]×[Act.Th2 lymphocyte influence degree (%) calculated using Tc*DR lymphocyte as the objective variable]×[CD20*DR influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 μL blood of data cluster)

Here, contribution ratio in the regression analysis in which NK cell is set as objective variable and all other immunocompetent cells are set as explanatory variables is equal to the sum of respective influence degrees of all immunocompetent cells when the influence degrees are calculated using NK cell as the objective variable.

Also, contribution ratio in the regression analysis in which NKT cells is set as objective variable and all other immunocompetent cells are set as explanatory variables is equal to the sum of respective influence degrees of all immunocompetent cells when the influence degrees are calculated using NKT cells as the objective variable.

Also, contribution ratio in the regression analysis in which Tc*DR lymphocyte is set as objective variable and all other immunocompetent cells are set as explanatory variables is equal to the sum of respective influence degrees of all immunocompetent cells when the influence degrees are calculated using Tc*DR lymphocyte as the objective variable.

Note that, in multiple regression analysis in which NK cell is set as the objective variable, if the standard partial regression coefficient of monocyte, Act.Th1 lymphocyte or Tc*DR lymphocyte is negative, T-cellular antigen recognition mechanism (TARM) is yet to be established and therefore an NK-cell activity index cannot be calculated. Moreover, in multiple regression analysis in which NK cell is set as the objective variable, if standard partial regression coefficient of monocyte, Act.Th2 lymphocyte or CD20*DR lymphocyte is negative, B-cellular Antigen Recognition Mechanism (BARM) is yet to be established and therefore an NK-cell ADCC activity cannot be calculated.

Similarly, in a multiple regression analysis in which NKT cell is set as the objective variable, if the standard partial regression coefficient of monocyte, Act.Th1 lymphocyte or Tc*DR lymphocyte is negative, T-cellular antigen recognition mechanism (TARM) is yet to be established and therefore an NKT-cell activity index cannot be calculated. Moreover, in multiple regression analysis in which NKT cell is set as the objective variable, if the standard partial regression coefficient of monocyte, Act.Th2 lymphocyte or CD20*DR lymphocyte is negative, B-cellular Antigen Recognition Mechanism (B-cellular Antigen Recognition Mechanism: BARM) is yet to be established and therefore an NKT-cell ADCC activity cannot be calculated.

Similarly, in multiple regression analysis in which Tc*DR cell is set as the objective variable, if the standard partial regression coefficient of monocyte, Act.Th1 lymphocyte or Tc*DR lymphocyte is negative, T-cellular antigen recognition mechanism (TARM) is yet to be established and therefore a killer T-cell activity index cannot be calculated. Moreover, in multiple regression analysis in which Tc*DR cell is set as the objective variable, if the standard partial regression coefficient of monocyte, Act.Th2 lymphocyte or CD20*DR lymphocyte is negative, B-cellular Antigen Recognition Mechanism (B-cellular Antigen Recognition Mechanism: BARM) is yet to be established and therefore a killer T-cell ADCC activity cannot be calculated.

Hereinbelow, the present invention will be further explained in detail in reference to working examples, though the present invention is not to be limited by these working examples.

Working Examples

Example 1

Subject Sorting

Subjects consist of 177 cases undergoing hospital treatment for prostate cancer at various stages and levels of malignancy before treatment. Various treatments were given including hormonal therapy, radical operation and transurethral resection of prostate, etc.

Before starting treatment of prostate cancer, the numbers of monocytes, basophils, eosinophils and neutrophils, and the abundance ratio of different markers in different lymphocytes as well as PSA values were measured. The measurement was carried out by SRL, Inc. by request.

A multiple regression analysis was performed using PSA value as objective variable, and 17 types: CD3-positive lymphocyte, CD4-positive lymphocyte, CD8-positive lymphocyte, CD20*DR lymphocyte, Th1 lymphocyte, Th2 lymphocyte, Ti lymphocyte, Tc lymphocyte, Ts lymphocyte, Act.i/h T lymphocyte, Act.s/c T lymphocyte, NK cell, N3+ cell, monocyte, basophil, eosinophil and neutrophil as explanatory variables. Then, each expected value was subtracted from respective observed value to give a residual value, which was sorted in ascending order and divided into 3 groups containing 59 cases each, which were sorted into: GOOD group with low residual values; MODERATE group with middle residual values; and BAD group with high residual values.

GOOD group: Age between 54 and 89, median 73 years old. PSA value (ng/ml) between 0.006 and 218.1, median 11. Stages of advance by ABCD categorization: A1: 1 case, A2: 2 cases, B1: 12 cases, B2: 15 cases, C: 21 cases, D1: 4 cases, D2: 4 cases. Malignancy in Gleason score total: between 3 and 10, median 6. Follow-up between 84 and 5,260 days, median 885 days.

MODERATE group: Age between 53 and 90, median 72 years old. PSA value (ng/ml) between 0.1 and 426.92, median 11.54. Stages of advance: A2: 2 cases, B1: 11 cases, B2: 8 cases, C: 24 cases, D1: 5 cases, D2: 9 cases. Malignancy between 3 and 9, median 6. Follow-up between 118 and 2,305 days, median 745 days.

BAD group: Age between 51 and 89, median 71 years old. PSA value (ng/ml) between 0.983 and 6745, median 44.32. Stages of advance: A1: 4 cases, B1: 8 cases, B2: 4 cases, C: 16 cases, D1: 5 cases, D2: 23 cases. Malignancy between 3 and 10, median 7. Follow-up between 1 and 6308 days, median 901 days.

The survival rate curves of GOOD, MODERATE and BAD groups (59 cases each, total 177 cases) are shown in FIG. 1. Sorting into groups by the residual values was correlated with the survival rate.

Example 2

Discriminant Analysis

Figure 2:
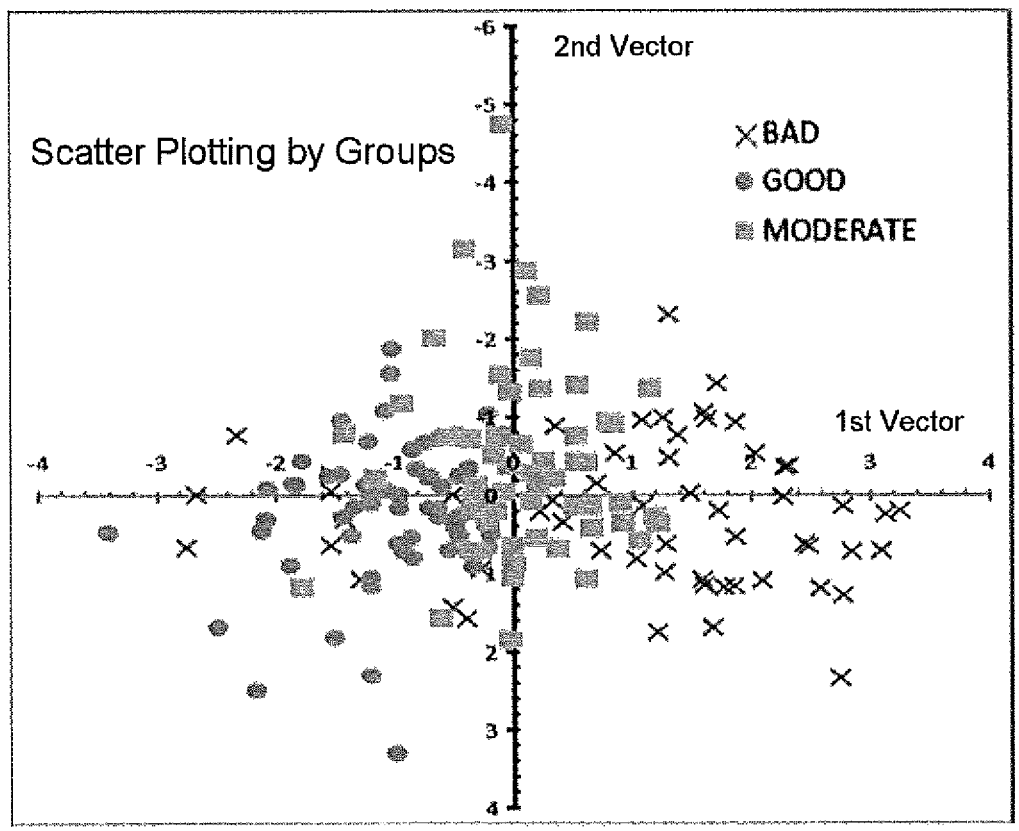
FIG. 2 represents a scatter plotting of discriminant scores of 177 cases.

A discriminant analysis was performed, in which three groups of GOOD, MODERATE and BAD groups were set as objective variables and 17 types of immunocompetent cells: CD3-positive lymphocyte, CD4-positive lymphocyte, CD8-positive lymphocyte, CD20*DR lymphocyte, Th1 lymphocyte, Th2 lymphocyte, Ti lymphocyte, Tc lymphocyte, Ts lymphocyte, Act.i/h Tlymphocyte, Act.s/c T lymphocyte, NK cell, N3+ cell, monocyte, basophil, eosinophil and neutrophil were set as explanatory variables, to give discriminant functions. The scatter plotting of discriminant scores plotted with first discriminant function values on X-axis and second discriminant function values on Y-axis is shown in FIG. 2. The discrimination accuracy rate was 71.8%.

Example 3

Categorization by Discriminant Scores

Three hundred and forty-four blood samples in total were collected from 66 subjects including 23 healthy individuals and 43 patients, and analyzed. Male/female ratio was 43:23, and the age was between 35 and 81 years old, median 65, mean±S.D. 65.39±7.70 years old. The number of measurements was between once and 47 times, the median was twice, and the mean±S.D. was 5.2±7.2 times. Healthy individuals are at the age between 44 and 73 years old, the median 60, the mean±S.D. 59.21±4.98 years old. The male/female ratio was 15/8, the number of measurements was between once and 12 times, the median was twice, and the mean±S.D. was 3.13±3.21 times. Cases for patients were as described in Table 2. A patient who had complication of gastric cancer and bladder cancer was recorded in duplicate.

was sorted into a group the center of which was the closest. 162 cases were sorted into GOOD group, 45 cases into MODERATE group and 137 cases into BAD group.

Figure 5:
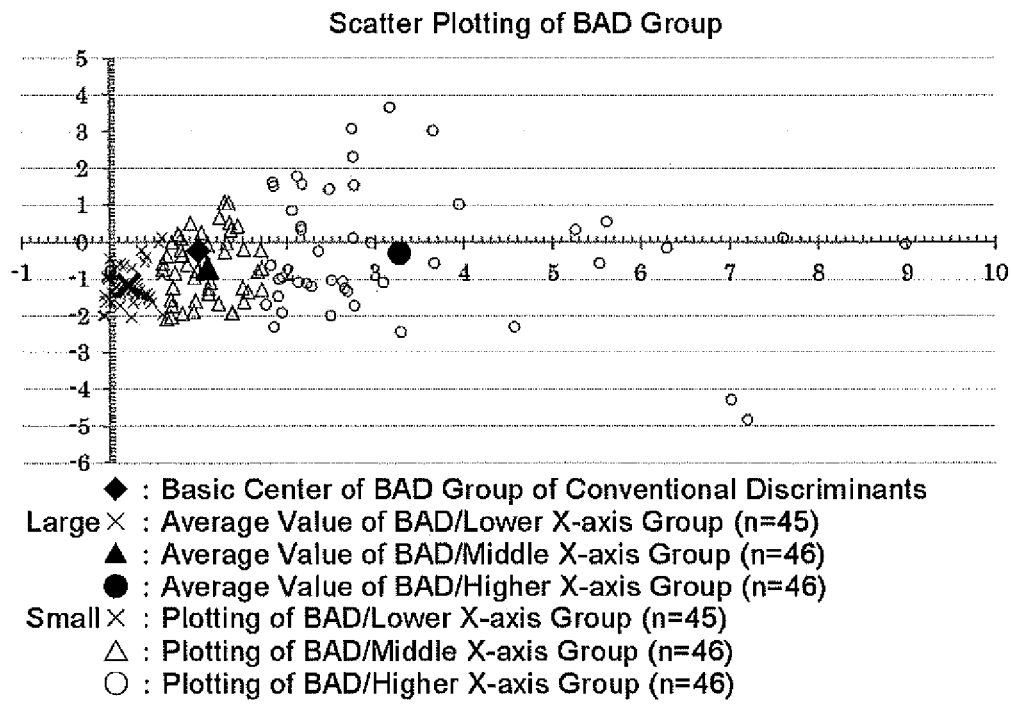
FIG. 5 represents scatter plotting of discriminant scores of 137 cases sorted into BAD group.

FIGS. 3, 4 and 5 show scatter plots of discriminant scores of 162 cases sorted into GOOD group, 45 cases sorted into MODERATE group, and 137 cases sorted into BAD group, respectively.

Example 4

Regression Analysis and Immunodynamics Chart Generation

GOOD/Lower X-Axis Group; n=54/T-cell Immunity 162 cases sorted in GOOD group are divided into three groups based on X-axis value, and an analysis directed toward T-cell immunity was performed for cell-count data of 54 cases with low X-axis values.

A multiple regression analysis was performed using Tc*DR lymphocyte as objective variable, and CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil as explanatory variables. The contribution ratio was 96.473%. The standard partial regres-

TABLE 2

| Identity of cancer | Number of cases | Notes | Female | Male |
|---|---|---|---|---|
| Lung cancer | 5 | 4 recurrence/metastasis cases being treated; 1 case indicating good postoperative course. | 2 | 3 |
| Lingual cancer | 1 | Receiving follow-up. | | 1 |
| Gastric cancer | 4 | 1 case of complication of bladder cancer; only 1 case indicating good course. | 2 | 2 |
| Liver cancer | 1 | Passed away due to disease progression. | | 1 |
| Gallbladder cancer | 1 | Passed away due to disease progression. | | 1 |
| Bile duct cancer | 1 | Receiving postoperative follow-up. | 1 | |
| Pancreatic cancer | 1 | Treatment for liver metastasis; passed away due to disease progression. | | 1 |
| Colon cancer | 3 | Only 1 case being treated for peritoneal metastasis. | | 3 |
| Rectal cancer | 1 | Lymph node metastasis; radical cure after treatment with anticancer agent; post-operational peritoneal metastasis. | 1 | |
| Breast cancer | 4 | Only 1 case indicating good postoperative course; others being treated with anticancer agent. | 4 | |
| Ovary cancer | 3 | Treatment for intraperitoneal metastasis; only 1 case indicating good course. | 3 | |
| Uterine body cancer | 1 | Being treated with anticancer agent. | 1 | |
| Renal cancer | 2 | Molecular targeted therapy for metastasis; exacerbated. | | 2 |
| Bladder cancer | 3 | Only 2 cases with pre-/post-treatment observation; 1 case in treatment. | 1 | 2 |
| Prostate cancer | 12 | 11 cases of hormonal therapy for recurrence/relapse after treatment; only 1 receiving follow-up after treatment. | | 12 |
| Testicular cancer | 1 | Indicating good postoperative course, no recurrence for 6 yrs. | | 1 |
| Total | 44 | | 15 | 29 |

The numbers of monocytes, basophils, eosinophils and neutrophils, as well as the abundance ratios of different markers in different lymphocytes were measured by SRL, Inc. by request.

For each case, the discriminant scores were calculated by assigning cell-counts of immunocompetent cells into the discriminant functions obtained in Example 2, and each case sion coefficients of 25 types of immunocompetent cells obtained by multiple regression analysis are shown in Table 3.

The standard partial regression coefficients of the immunocompetent cells obtained in this analysis were sorted in descending order according to their absolute values. Namely, in descending order from the highest absolute value: CD4-positive lymphocyte, Th± lymphocyte, Ti+2 lymphocyte, Ts*DR lymphocyte, Th−2 lymphocyte, CD3-positive lymphocyte, Ti−2 lymphocyte, Th+2 lymphocyte, Tc+ lymphocyte, N3+ cell, basophil, Ti± lymphocyte, monocyte, CD8-positive lymphocyte, CD20*DR lymphocyte, Tc− lymphocyte, NKT cell, NK cell, Act.Th2 lymphocyte, Act.Th1 lymphocyte, eosinophil, Ts− lymphocyte, Ts+ lymphocyte, neutrophil and Ti*DR lymphocyte.

TABLE 3

| Immunocompetent Cell | Standard Partial Regression Coefficient |
| --- | --- |
| CD4-positive lymphocyte | 2.9130 |
| Th ± lymphocyte | −0.8605 |
| Ti + 2 lymphocyte | −0.7539 |
| Ts*DR lymphocyte | 0.6438 |
| Th − 2 lymphocyte | −0.6067 |
| CD3-positive lymphocyte | −0.5657 |
| Ti − lymphocyte | −0.3586 |
| Th + 2 lymphocyte | −0.3487 |
| Tc + lymphocyte | 0.3439 |
| N3 + cell | −0.3185 |
| Basophil | −0.2636 |
| Ti ± lymphocyte | −0.2249 |
| Monocyte | 0.2238 |
| CD8-positive lymphocyte | 0.2191 |
| CD20*DR lymphocyte | 0.2149 |
| Tc − lymphocyte | 0.2020 |
| NKT cell | 0.1689 |
| NK cell | 0.1418 |
| Act. Th2 lymphocyte | 0.1185 |
| Act. Th1 lymphocyte | −0.1028 |
| Eosinophil | 0.0938 |
| Ts − lymphocyte | 0.0850 |
| Ts + lymphocyte | −0.0421 |
| Neutrophil | −0.0387 |
| Ti*DR lymphocyte | 0.0132 |

Next, a regression analysis was performed using Tc*DR lymphocyte as objective variable, and CD4-positive lymphocyte that was ranked as the first place for the magnitude of the absolute value of the standard partial regression coefficient as explanatory variable, and the contribution ratio was calculated. The contribution ratio thus obtained was 63.411%, which was considered as the influence degree of the CD4-positive lymphocyte.

Then, a multiple regression analysis was performed using Tc*DR lymphocyte as objective variable, and two types of immunocompetent cells: CD4-positive lymphocyte that was ranked as the first place for the magnitude of the absolute value of the standard partial regression coefficient and Th± lymphocyte that was ranked as the second place as explanatory variables, and the contribution ratio was calculated as 65.381%. Subtracting from this value the contribution ratio 63.411% in the case when only CD4-positive lymphocyte was used as explanatory variable gave a value 1.970%, which was considered as the influence degree of Th± lymphocyte.

Next, a multiple regression analysis was performed using three types of immunocompetent cells that were ranked as the first to the third places, i.e., CD4-positive lymphocyte, Th± lymphocyte and Ti+2 lymphocyte as explanatory variable, and the contribution ratio was calculated to be 70.130%. Subtracting from this value the contribution ratio 65.381% in the case when two types of immunocompetent cells: CD4-positive lymphocyte and Th± lymphocyte were used as explanatory variables gave a value 4.749%, which was considered as the influence degree of Ti+2 lymphocyte.

A series of multiple regression analyses was performed with increasing number of explanatory variables, starting from CD4-positive lymphocyte that was ranked as the first place to the last (25th) immunocompetent cell-type. The calculated influence degrees of 25 types of immunocompetent cells are shown in Table 4.

TABLE 4

| Immunocompetent Cell | Influence Degree (%) |
| --- | --- |
| CD4-positive lymphocyte | 63.411 |
| Th ± lymphocyte | 1.970 |
| Ti + 2 lymphocyte | 4.749 |
| Ts*DR lymphocyte | 13.385 |
| Th − 2 lymphocyte | 0.290 |
| CD3-positive lymphocyte | 2.158 |
| Ti − 2 lymphocyte | 2.101 |
| Th +2 lymphocyte | 0.962 |
| Tc + lymphocyte | 2.777 |
| N3 + cell | 1.420 |
| Basophil | 0.010 |
| Ti ± lymphocyte | 0.480 |
| Monocyte | 0.117 |
| CD8-positive lymphocyte | 0.167 |
| CD20*DR lymphocyte | 0.670 |
| Tc − lymphocyte | 0.893 |
| NKT cell | 0.170 |
| NK cell | 0.429 |
| Act. Th2 lymphocyte | 0.038 |
| Act. Th1 lymphocyte | 0.041 |
| Eosinophil | 0.138 |
| Ts − lymphocyte | 0.065 |
| Ts + lymphocyte | 0.015 |
| Neutrophil | 0.017 |
| Ti*DR lymphocyte | 0.000 |

Figure 6:
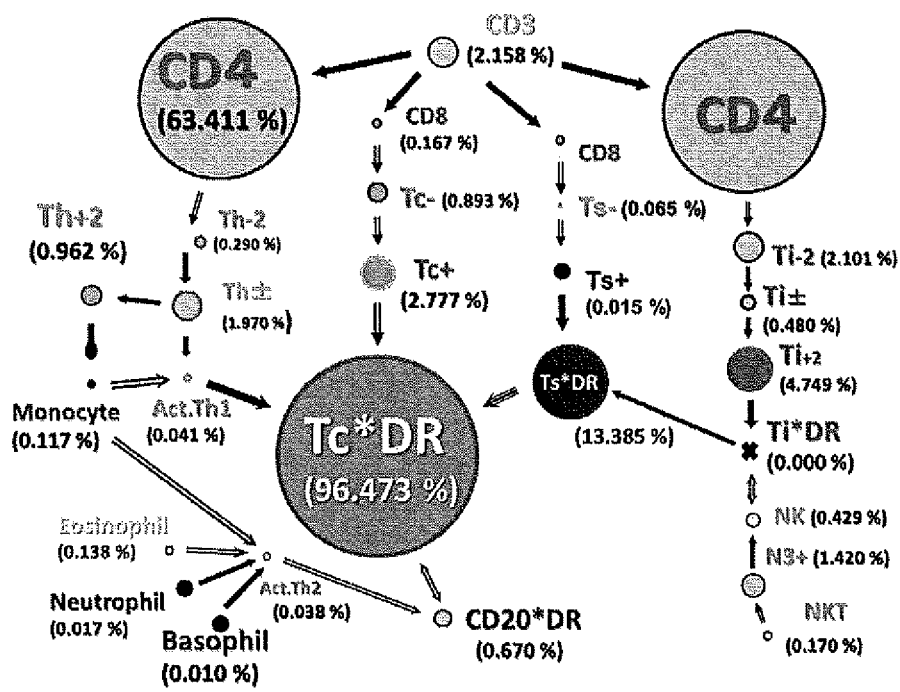
FIG. 6 represents an immunodynamics chart for T-cell immunity in GOOD/lower X-axis group (n=54).

The percentage of the influence degree was reflected to the area of a circle to generate an immunodynamics chart. X denotes an influence degree below 0.00785%, whereas ● denotes the influence degree at or above 0.00785% and less than 0.0314%. The generated immunodynamics chart is shown in FIG. 6.

Anti-tumor effect is generally exerted as follows. An antigen is loaded by an antigen-presenting cell (such as monocytes/macrophages) onto an MHC (Major Histocompatibility Complex) Class II molecule, presented to MHC Class II molecules on Act.Th1 lymphocyte. Act.Th1 lymphocyte produces cytokines, etc. based on information of the antigen, promoting activation of activated cytotoxic T cells (Tc*DR), and at the same time presents the cancer- (tumor-) specific antigen on MHC Class I, thereby exerting anti-tumor effect. Therefore, in order to obtain a persistent anti-tumor effect, it is necessary that Monocyte->Act.Th1->Tc*DR pathway (T-cellular antigen recognition mechanism (TARM)) has been established.

In the immunodynamics chart, Act.Th1 is in negative relationship to Tc*DR and the pathway from Act.Th1 to Tc*DR has been disrupted. Thus, no anti-tumor effect can be expected.

Activation of TARM can be achieved by therapies for stimulating the pathway from monocyte to Act.Th1 by dendritic cell vaccine therapy, or alternatively by administrating interleukin-1β (IL-1β) inhibitor (e.g., canakinumab, etc.) or functional foods or supplements such as fungal glycoproteins. In addition, therapies of enhancing Tc*DR by activating Act.Th1 using interferon a, etc. can also be employed.

Moreover, since Ts*DR is at a level as high as 13.385%, the suppressing of Ts*DR using monoclonal antibodies, etc. would relieve Tc*DR from the suppression by Ts*DR and successfully activate/enhance CD3->CD8->Tc-->Tc+->Tc*DR pathway, which might in turn open the TARM pathway.

Moreover, since differentiation and proliferation are stagnated at CD4, stimulating it with interleukin-2 (IL-2), a T-cell growth factor, would activate helper system, which might in turn open the TARM pathway.

Moreover, since Active Regulatory T-helper Cells (Th+2) which serve in immunosuppression is at a slightly high level as 0.962%, suppressing them with an antibody medicine such as ipilimumab (Trade name: Yervoy®) and mogamulizumab would relieve the antigen-presenting cells of the monocyte/macrophage system, which might bring TARM to function.

CD20*DR lymphocyte goes through Monocyte->Act.Th2->CD20*DR pathway (B-cellular Antigen Recognition Mechanism (BARM)) to produce antigens in cancer (tumor) antigen-dependent manner, whereas NK cell and NKT cell exert an antibody-dependent cellular cytotoxicity (ADCC).

In the immunodynamics chart, the BARM pathway has been opened, and thus antibody-dependent cellular cytotoxicity might be weak but still be expected.

Figure 7:
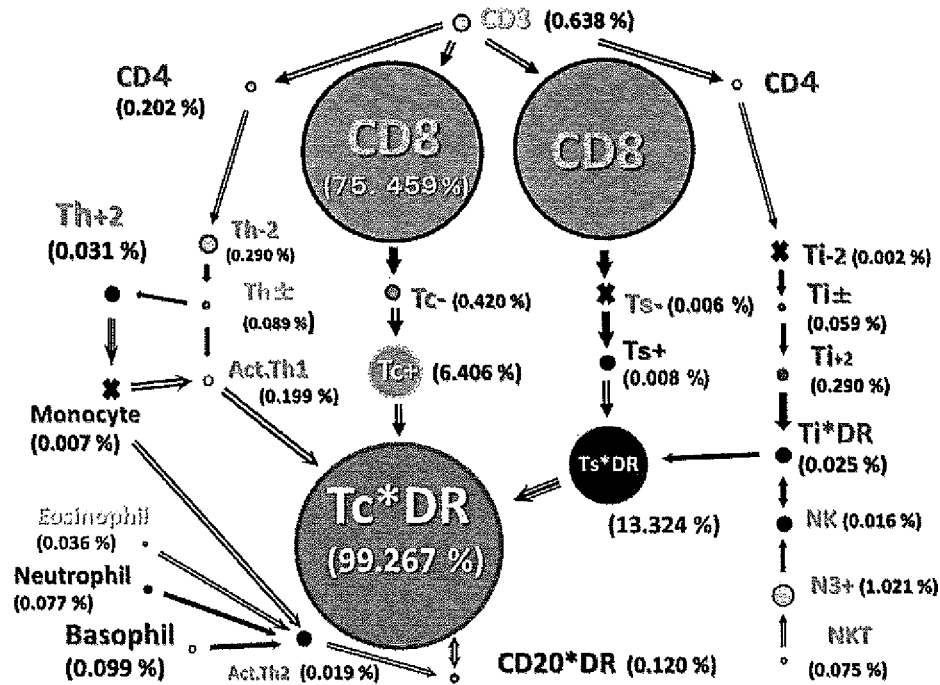
FIG. 7 represents an immunodynamics chart for T-cell immunity in GOOD/middle X-axis group (n=54).

GOOD/Middle X-Axis Group; n=54/T-Cell Immunity 162 cases sorted into GOOD group are divided into three groups based on X-axis value, and an analysis directed toward T-cell immunity was performed for cell-count data of 54 cases that had middle X-axis values in a similar way as in GOOD/lower X-axis group/T-cell immunity. The influence degrees were calculated and an immunodynamics chart was generated. The generated immunodynamics chart is shown in FIG. 7.

In the immunodynamics chart, both TARM and BARM have been established. Note that, unlike FIG. 6, differentiation and proliferation are stagnated at CD8, and the pathway from CD8 to Tc*DR has been disrupted. Possible treatments include activation/enhancement of CD3->CD8->Tc-->Tc+->Tc*DR pathway by 1L-2 administration, etc. Moreover, monocyte/macrophage system is at an extremely low level as 0.007%, which also needs to be activated. Th+2 is at a low level and it therefore does not need to be suppressed. Ts*DR is at a level as high as 13.324, and therefore, in case if there is no improvement from the aforementioned treatment, a therapy for suppressing Ts*DR with antibody medicine may be employed.

GOOD/Higher X-Axis Group; n=54/NK Cell 162 cases sorted in GOOD group are divided into three groups based on X-axis value, and an analysis directed toward NK cell was performed for cell-count data of 54 cases that had high X-axis values.

Figure 8:
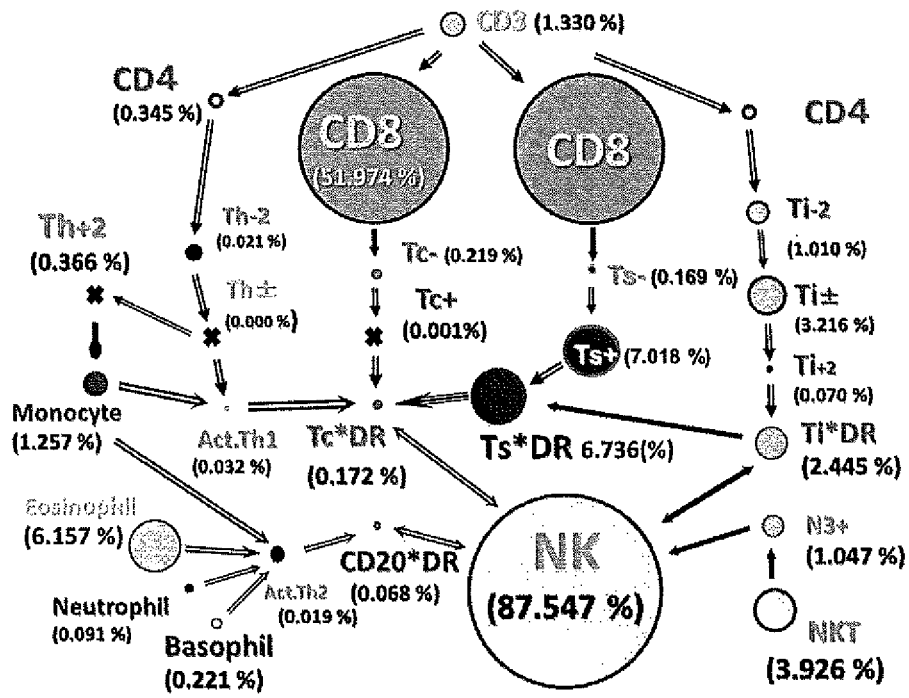
FIG. 8 represents an immunodynamics chart for NK cell in GOOD/higher X-axis group (n=54).

A multiple regression analysis was performed using NK cell as objective variable, and CD3-positive lymphocyte, CD4-positive lymphocyte, CD8-positive lymphocyte, CD20*DR lymphocyte, Th± lymphocyte, Th-2 lymphocyte, Th+2 lymphocyte, Act.Th1 lymphocyte, Act.Th2 lymphocyte, Ti*DR lymphocyte, Ti± lymphocyte, Ti-2 lymphocyte, Ti+2 lymphocyte, Tc- lymphocyte, Tc+ lymphocyte, Tc*DR lymphocyte, Ts*DR lymphocyte, Ts- lymphocyte, Ts+ lymphocyte, NKT cell, N3+ cell, monocyte, basophil, eosinophil and neutrophil as explanatory variables. The standard partial regression coefficients of the immunocompetent cells obtained in this analysis were ranked in descending order according to their absolute values, and a multiple regression analysis using NK cell as objective variable was repeatedly performed in similar way as in GOOD/lower X-axis group/T-cell immunity, the influence degrees were calculated for all immunocompetent cells and an immunodynamics chart was generated. The generated immunodynamics chart is shown in FIG. 8.

Differentiation and proliferation are stagnated at CD8, and the pathway has been disrupted. Although TARM has been established, Tc*DR is at a level as low as 0.172%, and it is necessary to activate/enhance the pathway from CD8 to Tc*DR with IL-2 administration, etc. Namely, it can be said that this immune condition is just appropriate for applying NK-cell adoptive immunotherapy. Because BARM has also been established and ADCC is expected, anti-tumor immunity can be maintained and continued by activating TARM and BARM and enhancing NK cells.

GOOD/Middle X-Axis Group; n=26/NK Cell

Figure 9:
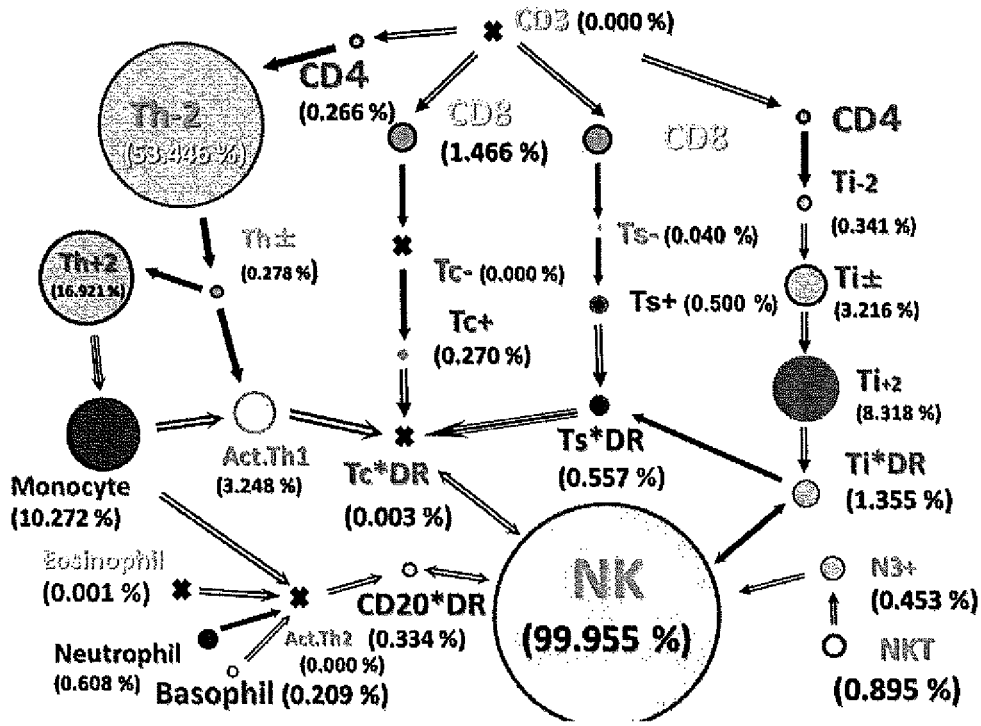
FIG. 9 represents an immunodynamics chart for NK cell in GOOD/middle X-axis group (n=26).

An analysis directed to NK cell was performed for cell-count data of 26 cases out of 54 cases sorted in GOOD/middle X-axis group in a similar way as in <GOOD/higher X-axis group; n=54/NK cell>. The influence degrees were calculated and an immunodynamics chart was generated. The generated immunodynamics chart is shown in FIG. 9.

Monocyte->Act.Th1->Tc*DR<=>NK pathway has been established and monocyte is at 10.272%, Act.Th1 is at 3.248%, though Tc*DR is at extremely low value as 0.003%. Moreover, since Th-2 pathway has been disrupted and Th+2 is at a level as high as 16.921%, anti-tumor effect cannot be expected. Therapies of activating Th-2 pathway with IL-2 administration, etc. and of suppressing Th+2 are required.

Besides, since Act.Th2 is at extremely low value as 0.000%, ADCC cannot be expected. NK-cell adoptive immunotherapy is considered to be promising.

GOOD Group; n=26/T-Cell Immunity

Figure 10:
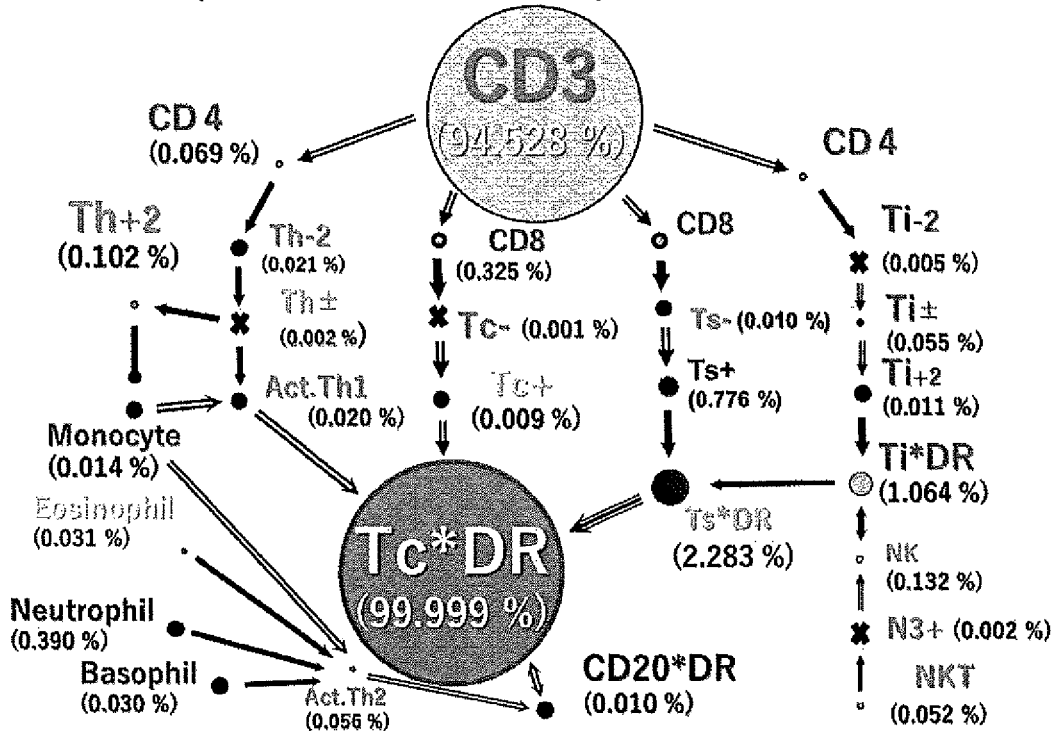
FIG. 10 represents an immunodynamics chart for T-cell immunity in GOOD group (n=26).

For cell-count data of 26 cases out of 162 cases sorted in GOOD group, an analysis directed toward 1-cell immunity was performed in a similar way as in <GOOD/lower X-axis group; n=54/T-cell immunity>. The influence degrees were calculated and an immunodynamics chart was generated. The generated immunodynamics chart is shown in FIG. 10.

TARM has been established though being weak. However, the differentiation/activation/enhancement pathway has been disrupted at CD3, and in this case, no effect can be expected by carrying out dendritic cell vaccine therapy.

The influence degree of CD3 is 94.528%, and thus the influence degree of pathways for other immunocompetent cells including granulocyte system are 5.471%, which is only approx. 5%. Treatment may include dissolving of the stagnation at CD3 by IL-2 administration, etc.

BARM has also been established, though CD20*DR is at a level as low as 0.010%, and neither antigen production effect nor ADCC can be expected.

In the immunodynamics chart, Act.Th2 (0.056%) >Act.Th1 (0.020%) and B-cell immunity are dominant. Therefore, it should be noted that a sudden start of therapy with an immune checkpoint inhibitor would cause autoimmune disease-like side effects.

GOOD Group; n=26/B-Cell Immunity

For cell-count data of 26 cases out of 162 cases sorted in GOOD group, an analysis directed to B-cell immunity was performed.

Figure 11:
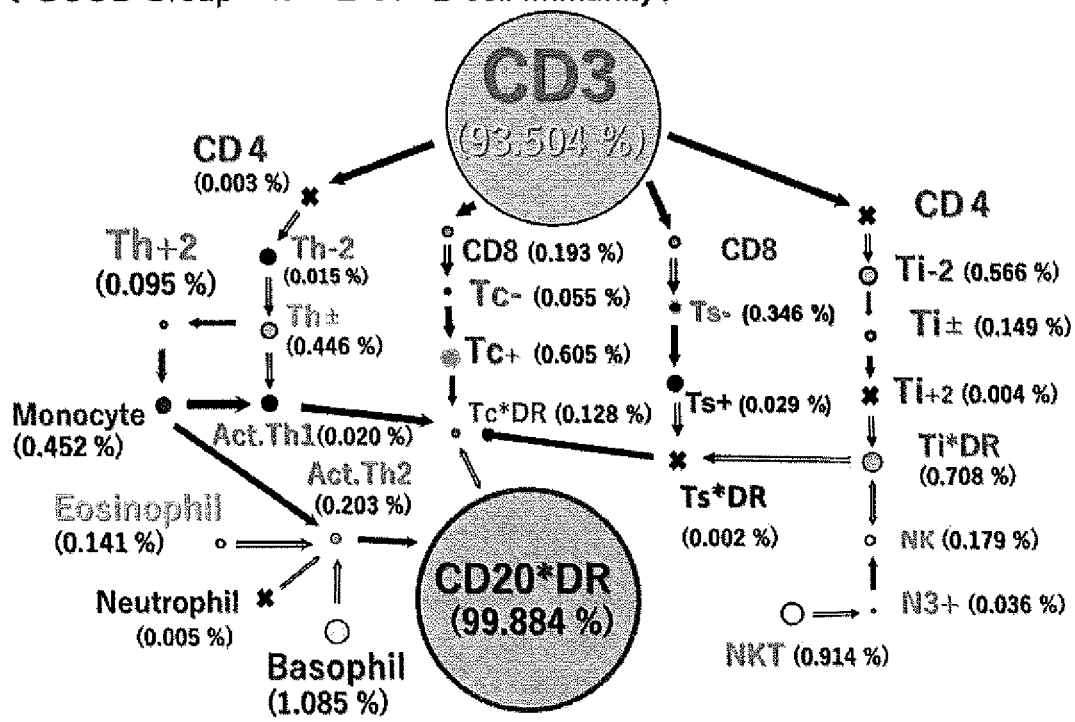
FIG. 11 represents an immunodynamics chart for B-cell immunity in GOOD group (n=26).

A multiple regression analysis was performed using CD20*DR lymphocyte as objective variable, and CD3-positive lymphocyte, CD4-positive lymphocyte, CD8-positive lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil, eosinophil and neutrophil as explanatory variables. The standard partial regression coefficients of the immunocompetent cells obtained in this analysis were ranked in descending order according to their absolute values, and a multiple regression analysis using CD20*DR lymphocyte as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 11.

Similar to FIG. 10, differentiation and proliferation are stagnated at CD3, and neither TARM nor BARM have been established. In order to drive the immunodynamics, it is necessary to dissolve the stagnation at CD3 by IL-2 administration, etc.

GOOD Group; n=26/Basophil

For cell-count data of 26 cases out of 162 cases sorted in GOOD group, an analysis directed to basophil was performed.

Figure 12:
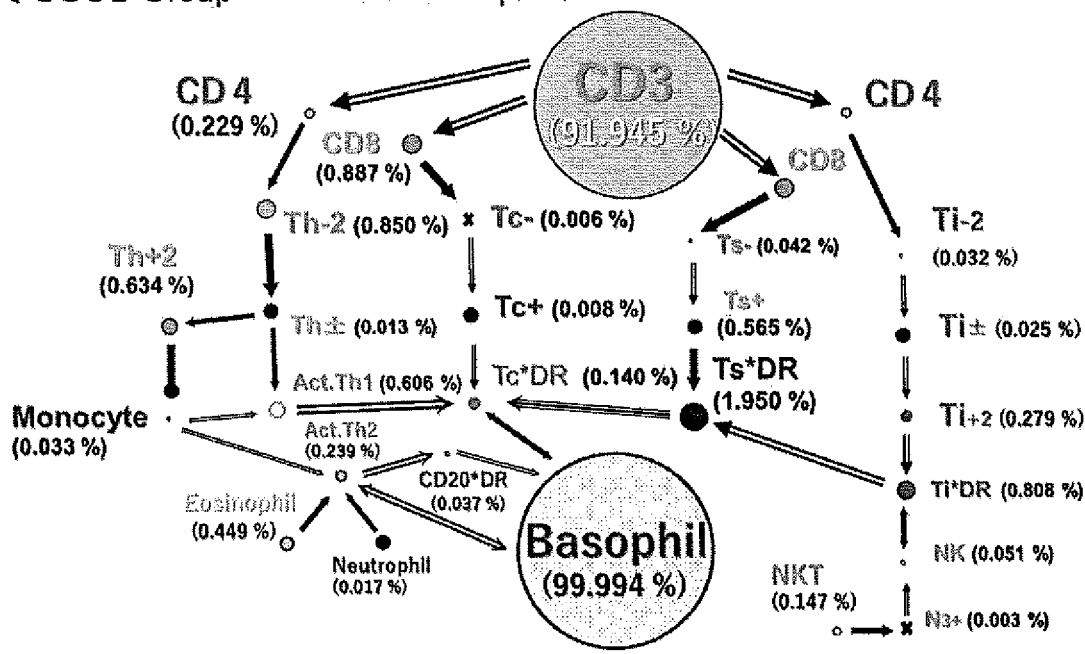
FIG. 12 represents an immunodynamics chart for basophil in GOOD group (n=26).

A multiple regression analysis was performed using basophil as objective variable, and CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, eosinophil and neutrophil as explanatory variables. The standard partial regression coefficients of the immunocompetent cells obtained in this analysis were ranked in descending order according to their absolute values, and a multiple regression analysis using basophil as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 12.

An immunodynamics chart directed to basophil shows an immunity related to immediate allergy, etc. When TH1-immunity (Monocyte->Act.Th1->Tc*DR<=>Basophil) or Th2-immunity (Monocyte->Act.Th2->CD20*DR<=>Basophil) has been established and activated, it is a severe case with immediate allergic reaction that would be an indication of an adrenaline intramuscular injection.

Although TARM has been weakly established, Tc*DR is in a negative relationship to basophil and the pathway has been disrupted.

BARM has been established, and furthermore, in Monocyte->Act.Th2->CD20*DR->Basophil<=>Act.Th2 pathway, the loop circuit from Act.Th2 to Act.Th2 has been established. Therefore, it should be noted that carrying out a therapy such as an immune checkpoint inhibitor such as nivolumab (Trade name: Opdivo®) from the first would induce immediate allergic symptoms, etc., and require emergency treatment such as adrenaline intramuscular injection.

GOOD Group; n=26/Eosinophil

For cell-count data of 26 cases out of 162 cases sorted in GOOD group, an analysis directed to eosinophil was performed.

Figure 13:
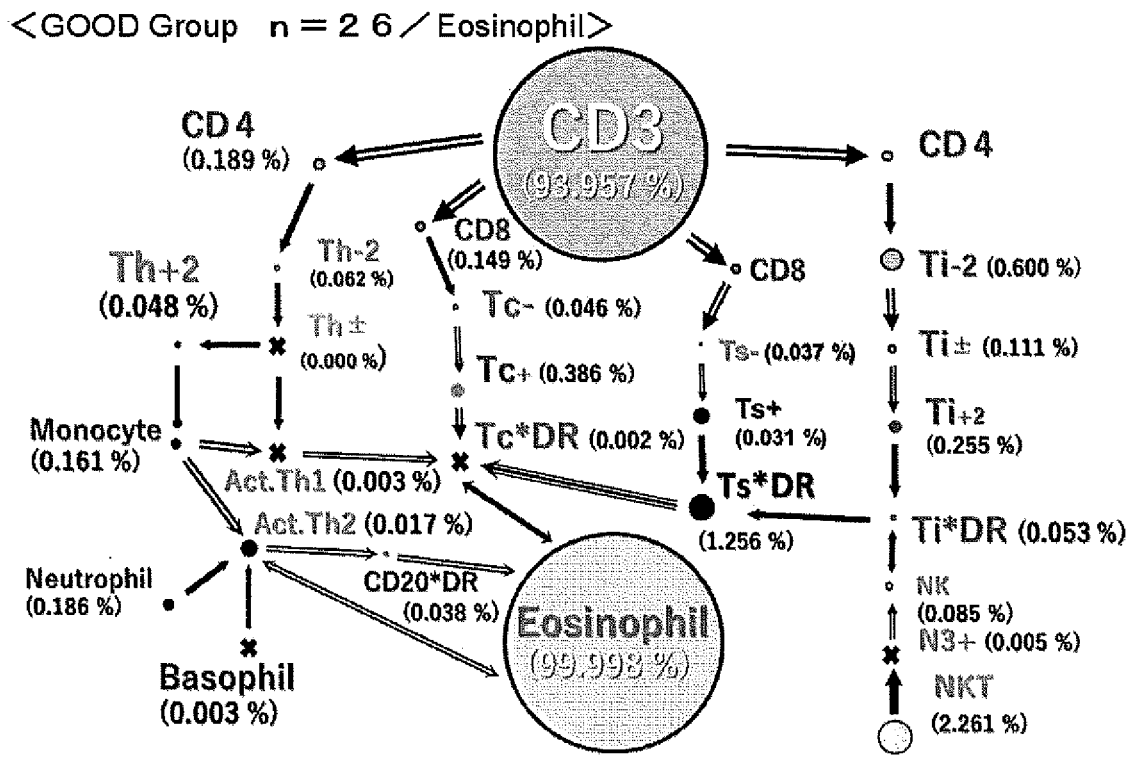
FIG. 13 represents an immunodynamics chart for eosinophil in GOOD group (n=26).

A multiple regression analysis was performed using eosinophil as objective variable, and CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil and neutrophil as explanatory variables. The standard partial regression coefficients of the immunocompetent cells obtained in this analysis were ranked in descending order according to their absolute values, and a multiple regression analysis using eosinophil as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 13.

Although TARM has been established, Tc*DR is in a negative relationship to eosinophil and the pathway has been disrupted.

However, BARM has been established, and furthermore, in Monocyte->Act.Th2->CD20*DR->Basophil<=>Act.Th2 pathway, the loop circuit from Act.Th2 to Act.Th2 has been established. Therefore, it should be noted that carrying out a therapy such as an immune checkpoint inhibitor such as nivolumab (Trade name: Opdivo®) from the first would induce immediate allergic symptoms, etc., and require emergency treatment such as adrenaline intramuscular injection.

GOOD Group; n=26/Neutrophil

For cell-count data of 26 cases out of 162 cases sorted in GOOD group, an analysis directed to neutrophil was performed.

Figure 14:
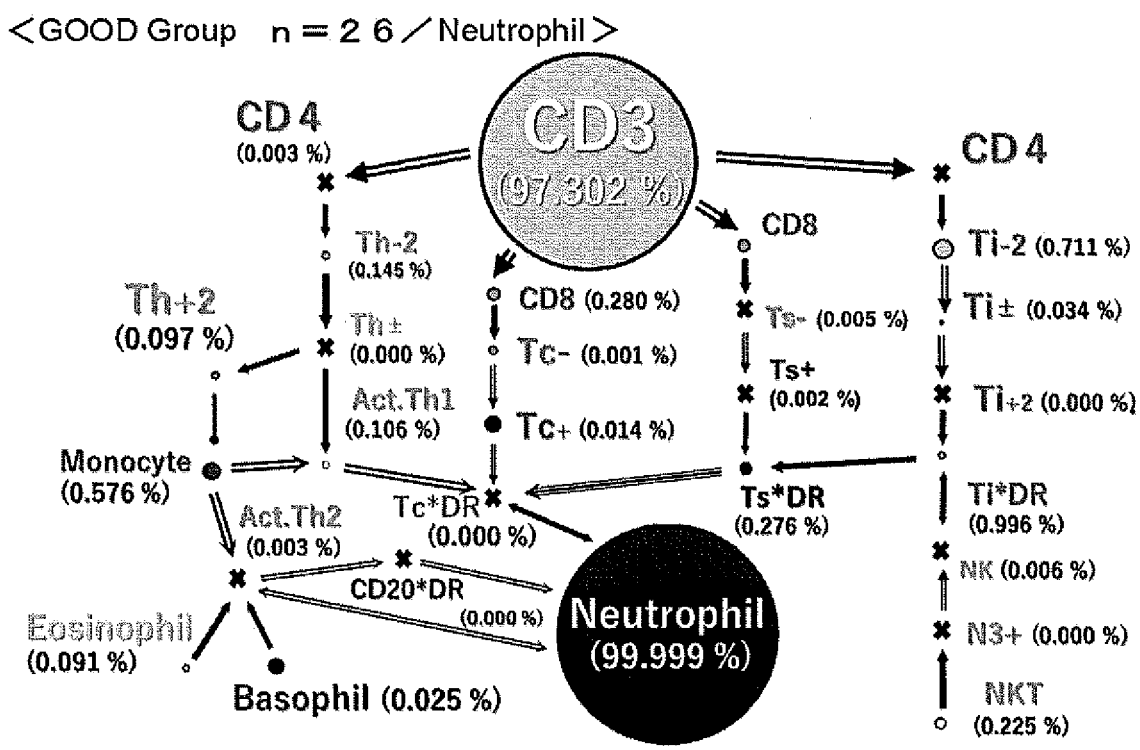
FIG. 14 represents an immunodynamics chart for neutrophil in GOOD group (n=26).

A multiple regression analysis was performed using neutrophil as objective variable, and CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil and eosinophil as explanatory variables. The standard partial regression coefficients of the immunocompetent cells obtained in this analysis were ranked in descending order according to their absolute values, and a multiple regression analysis using neutrophil as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 14.

Immunodynamics has been stagnated at CD3 almost completely. The influence degree of CD3 is 97.302%, and thus the influence degree for other pathway is less than 2.7%. T-cell immunity (anti-cancer immunity) cannot be expected. TARM has barely been maintained, though Tc*DR is 0.000% and has been completely obstructed. Moreover, Tc*DR is in negative relationship to neutrophil, and in this case, the anti-tumor effect by neutrophils such as with fractalkines can hardly be expected.

Furthermore, in a similar was as in FIGS. 12 and 13, in Monocyte->Act.Th2->CD20*DR->Neutrophil<=>Act.Th2 pathway, the loop circuit from Act.Th2 to Act.Th2 has been established. Therefore, a caution should be taken for inflammatory diseases.

MODERATE Group: n=45/NK Cell

Figure 15:
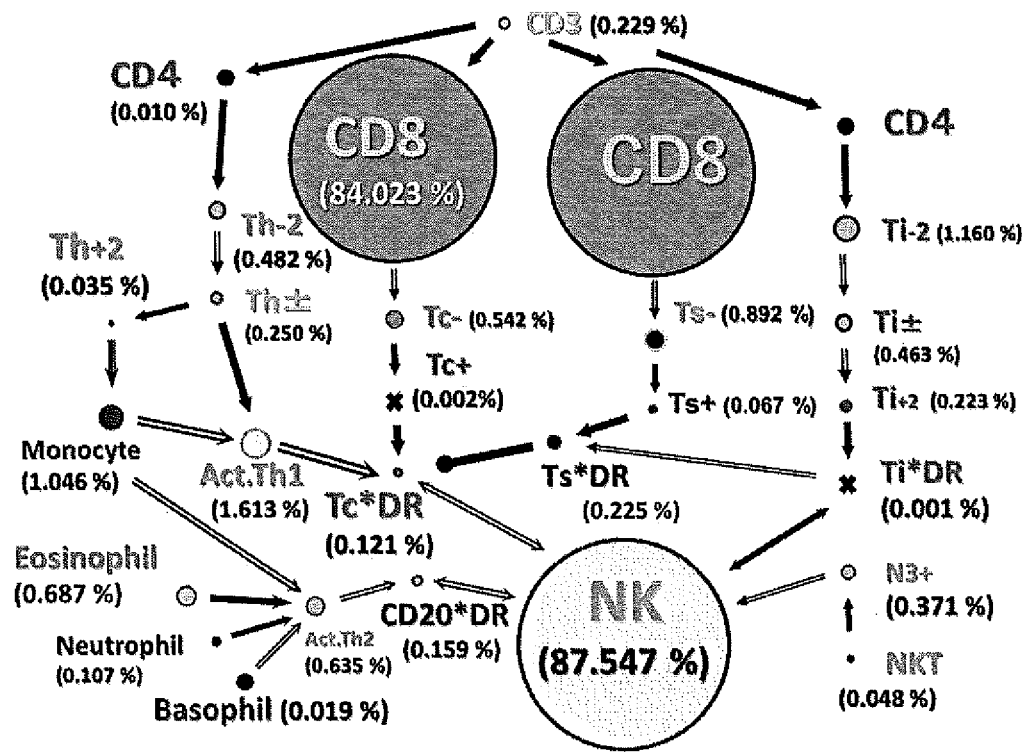
FIG. 15 represents an immunodynamics chart for NK cell in MODERATE group (n=45).

For cell-count data of 45 cases sorted in MODERATE group, an analysis directed to NK cell was performed in a similar way as in <GOOD/higher X-axis group/NK cell>. The influence degrees were calculated and an immunodynamics chart was generated. The generated immunodynamics chart is shown in FIG. 15.

Since there is stagnation at CD8, differentiating/multiplying/enhancing CD8->Tc-->Tc+->Tc*DR pathway by IL-2 administration, etc. will also actively enhances Monocyte->Act.Th1->Tc*DR <=>NK pathway, exerting an anti-cancer effect. ADCC activity can also be sufficiently expected, and in a case of such immunodynamics chart, an adoptive immunotherapy should be performed. If possible, continuous administration of IL-2 by subcutaneous injection or intravenous infusion for a few days after NK-cell autotransfusion will lead to an enhancement of the effect.

MODERATE Group; n=35/T-Cell Immunity

Figure 16:
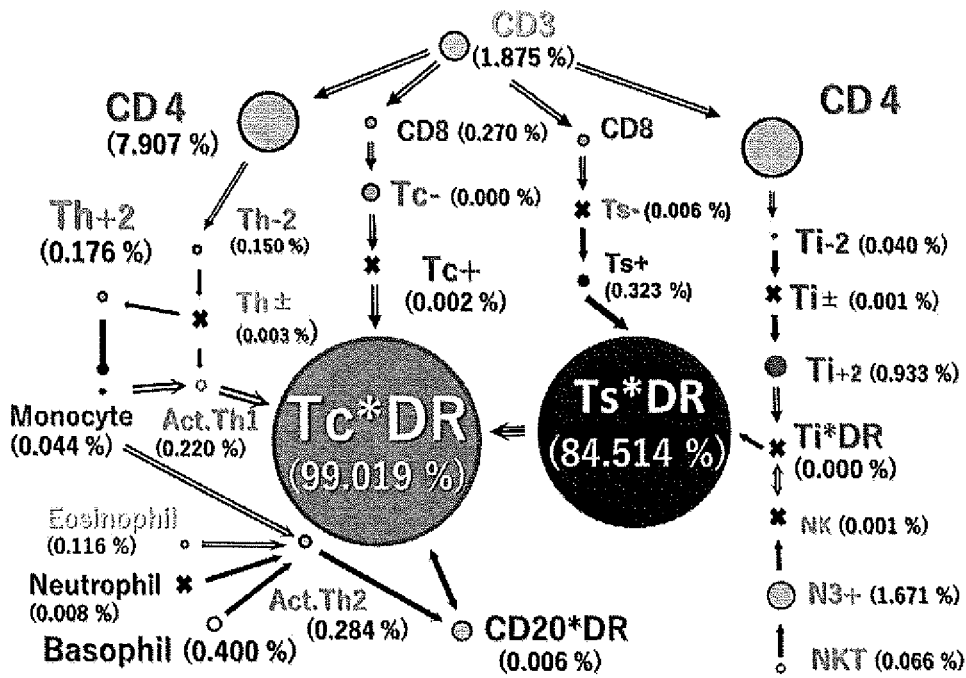
FIG. 16 represents an immunodynamics chart for T-cell immunity in MODERATE group (n=35).

For cell-count data of 35 cases out of 45 cases sorted in MODERATE group, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 16.

There is stagnation at Ts*DR, indicating considerable suppression by Ts*DR. Although T-cell immunity has been established, Ts*DR is considerably dominant and required to be controlled somehow. Therapies include a method of suppressing Ts*DR with monoclonal antibodies, NK-cell adoptive immunotherapy or NKT-cell adoptive immunotherapy may also be promising in some cases.

BAD Group; n=40/T-Cell Immunity

Figure 17:
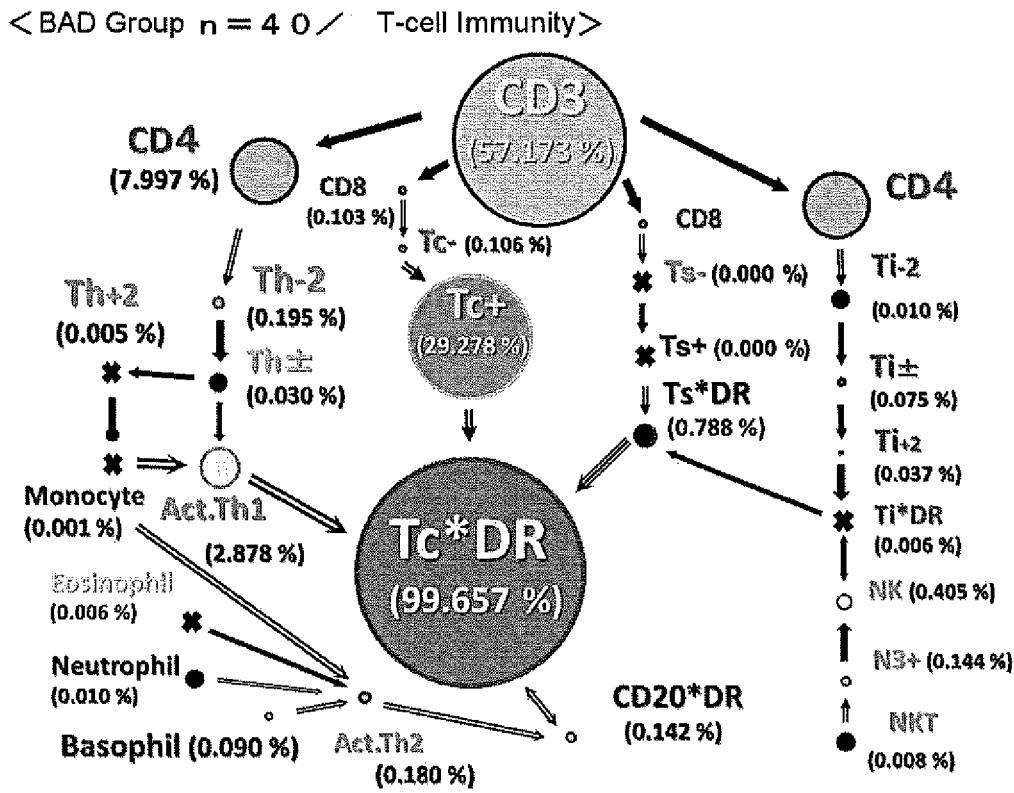
FIG. 17 represents an immunodynamics chart for T-cell immunity in BAD group (n=40).

For cell-count data of 40 cases out of 137 cases sorted in BAD group, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 17.

There is stagnation at CD3 and Tc+. Bringing this pathway to flow smoothly will induce anti-cancer (anti-tumor) immunity for a great deal, contributing to the reduction of cancer. To this end, allowing them to differentiate, proliferate, or be increased by IL-2 administration, etc. is considered to be effective. Furthermore, immune checkpoint inhibitors such as nivolumab (Trade name: Opdivo®) are considered to be effective.

Besides, since Monocyte->Act.Th2->CD20*DR<=>Tc*DR pathway has been established, ADCC activity may also be expected. Note that when using an immune checkpoint inhibitor, it is necessary to keep monitoring and observing the dynamics such that B-cell immunity will not become dominant.

BAD Group; n=26/Eosinophil

Figure 18:
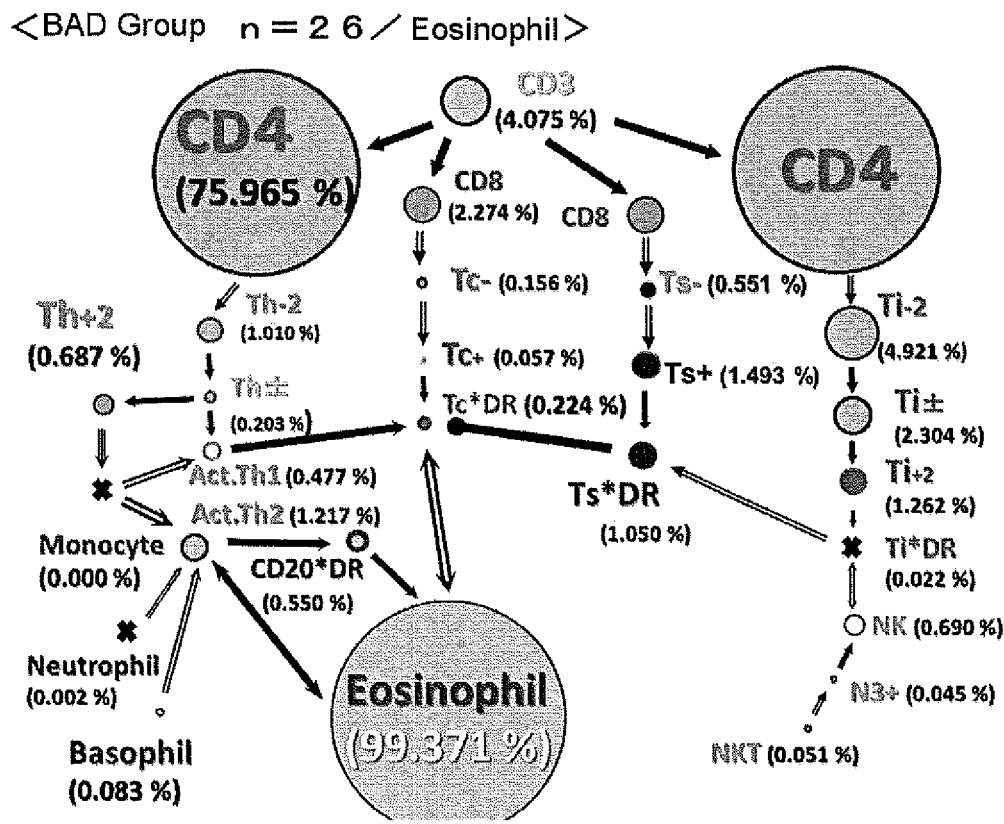
FIG. 18 represents an immunodynamics chart for eosinophil in BAD group (n=26).

For cell-count data of 26 cases out of 137 cases sorted in BAD group, an analysis directed to eosinophil was performed in a similar way as in <GOOD group; n=26/eosinophil>. The influence degrees were calculated and an immunodynamics chart was generated. The generated immunodynamics chart is shown in FIG. 18.

There is stagnation at CD4, and neither TARM nor BARM have been established. Moreover, no loop circuit from Act.Th2 to Act.Th2 has been established in Monocyte->Act.Th2->CD20*DR->Eosinophil<=>Act.Th2 pathway.

BAD Group; n=26/Basophil

Figure 19:
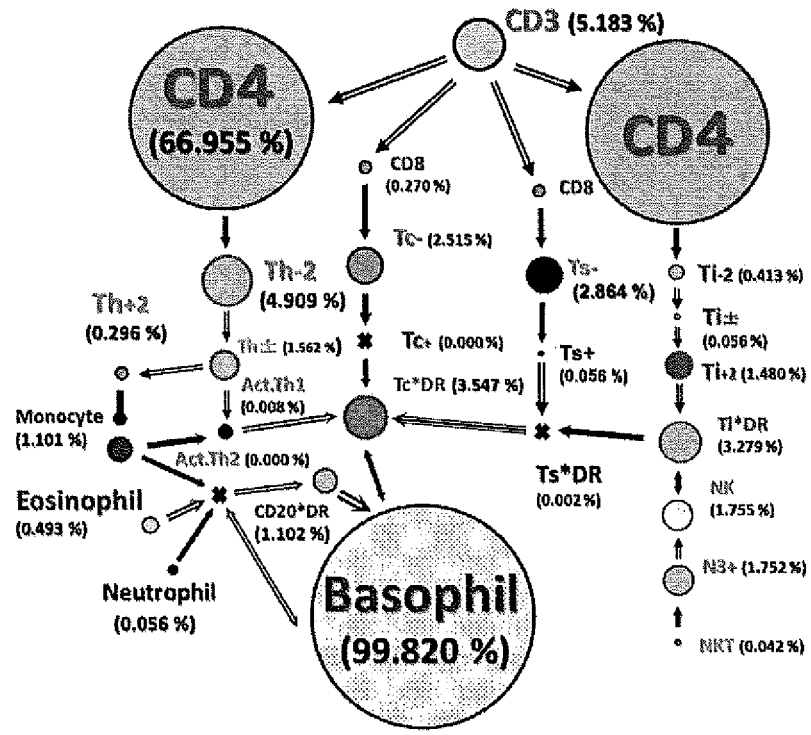
FIG. 19 represents an immunodynamics chart for basophil in BAD group (n=26).

For cell-count data of 26 cases out of 137 cases sorted in BAD group, an analysis directed to basophil was performed in a similar way as in <GOOD group; n=26/basophil>. The influence degrees were calculated and an immunodynamics chart was generated. The generated immunodynamics chart is shown in FIG. 19.

There is stagnation at CD4, and neither TARM nor BARM have been established. Moreover, since a loop circuit from Act.Th2 to Act.Th2 has been established in Monocyte->Act.Th2->CD20*DR->Basophil<=>Act.Th2 pathway, a care has to be taken in carrying out immunotherapy.

BAD Group; n=26/Neutrophil

Figure 20:
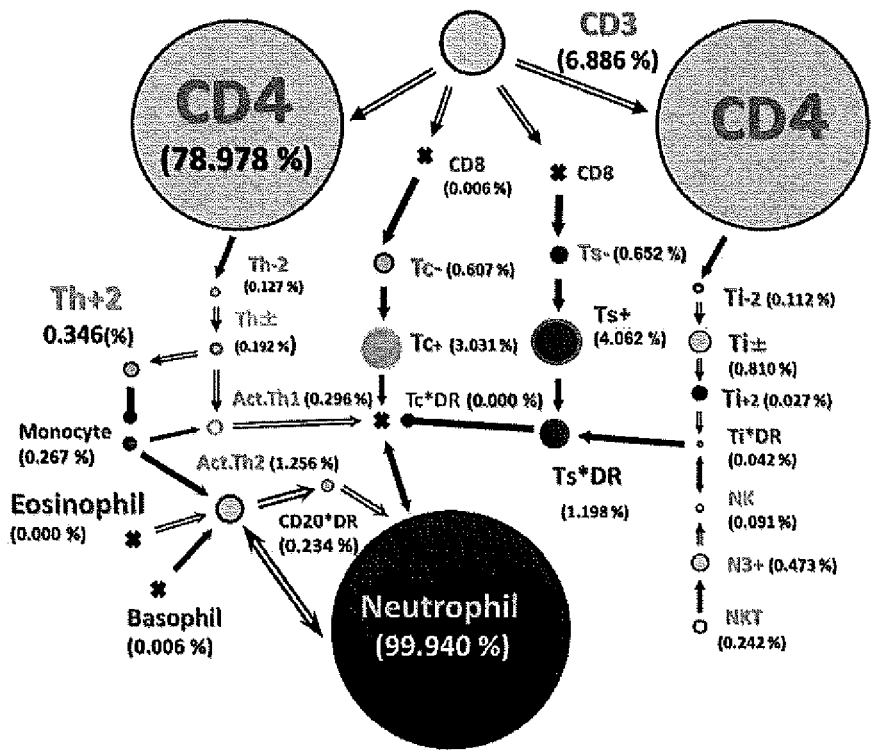
FIG. 20 represents an immunodynamics chart for neutrophil in BAD group (n=26).

For cell-count data of 26 cases out of 137 cases sorted in BAD group, an analysis directed to neutrophil was performed in a similar way as in <GOOD group; n=26/neutrophil>. The influence degrees were calculated and an immunodynamics chart was generated. The generated immunodynamics chart is shown in FIG. 20.

There is stagnation at CD4, and neither TARM nor BARM have been established. Moreover, since a loop circuit from Act.Th2 to Act.Th2 has been established in Monocyte->Act.Th2->CD20*DR->Neutrophil<=>Act.Th2 pathway, a care has to be taken in carrying out immunotherapy.

BAD Group; n=26/B-Cell Immunity

Figure 21:
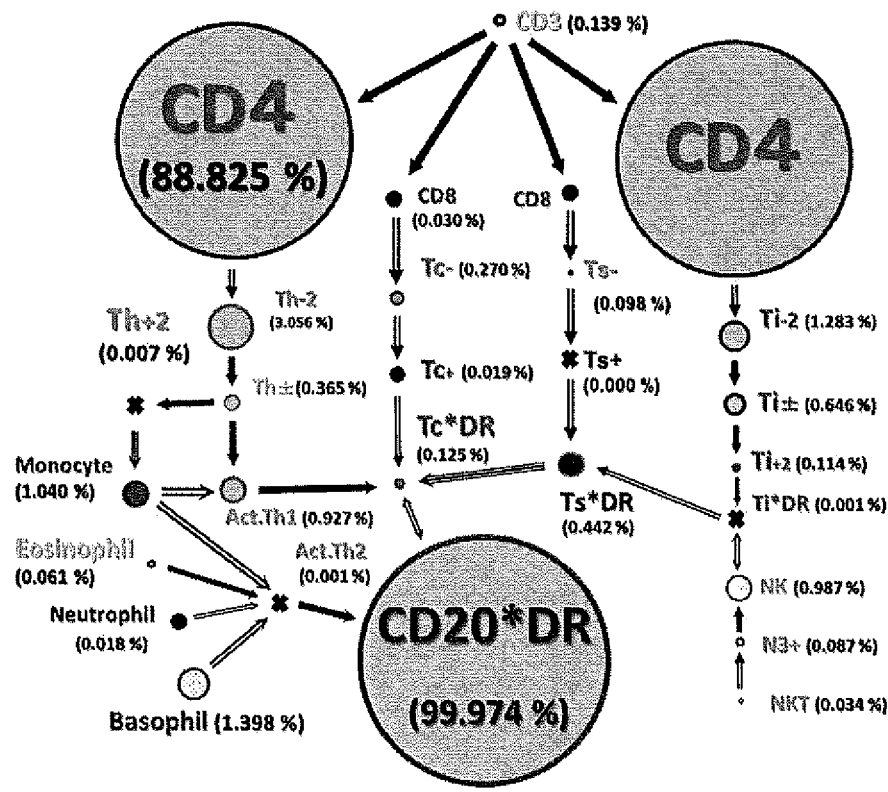
FIG. 21 represents an immunodynamics chart for B-cell immunity in BAD group (n=26).

For cell-count data of 26 cases out of 137 cases sorted in BAD group, an analysis directed to B-cell immunity was performed in a similar way as in <GOOD group; n=26/B-cell immunity>. The influence degrees were calculated and an immunodynamics chart was generated. The generated immunodynamics chart is shown in FIG. 21.

There is stagnation at CD4, and neither TARM nor BARM have been established.

BAD Group; n=26/NKT Cell

For cell-count data of 26 cases out of 137 cases sorted in BAD group, an analysis directed to NKT cell was performed.

Figure 22:
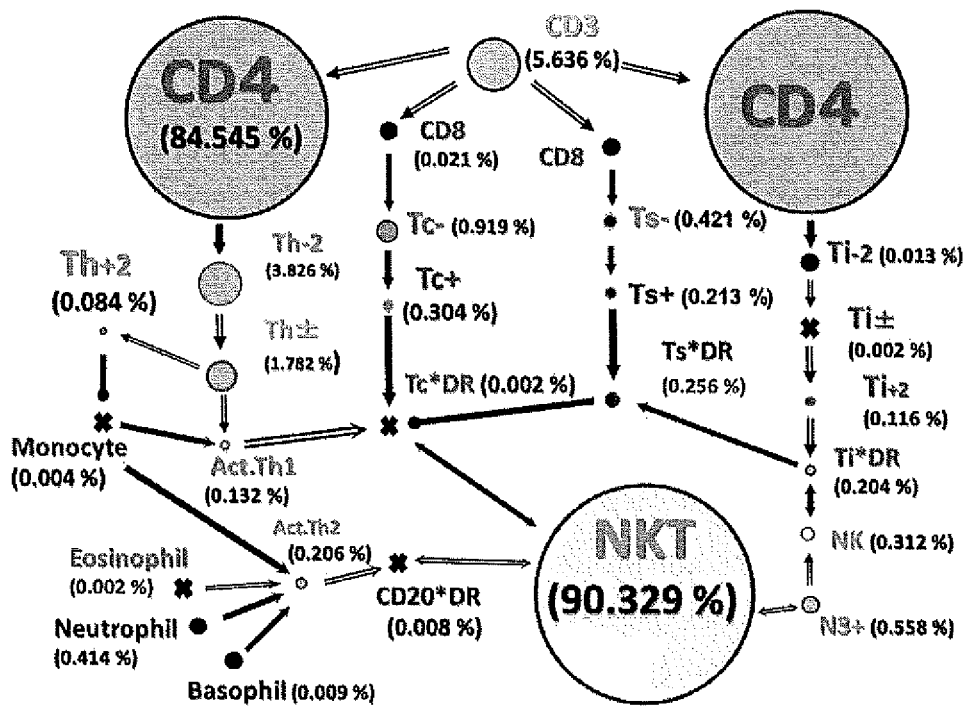
FIG. 22 represents an immunodynamics chart for NKT cell in BAD group (n=26).

A multiple regression analysis was performed using NKT cell as objective variable, and CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts– lymphocyte, Ts+ lymphocyte, NK cell, N3+ cell, monocyte, basophil, eosinophil and neutrophil as explanatory variables. The standard partial regression coefficients of the immunocompetent cells obtained in this analysis were ranked in descending order according to their absolute values, a multiple regression analysis using NKT cell as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 22.

There is stagnation and disruption at CD4. Therapies require differentiation, proliferation or enhancement of CD4 system by IL-2 administration, etc. Then, therapies should be reconsidered according to the changes in immunodynamics.

BAD Group; n=26/NK Cell

Figure 23:
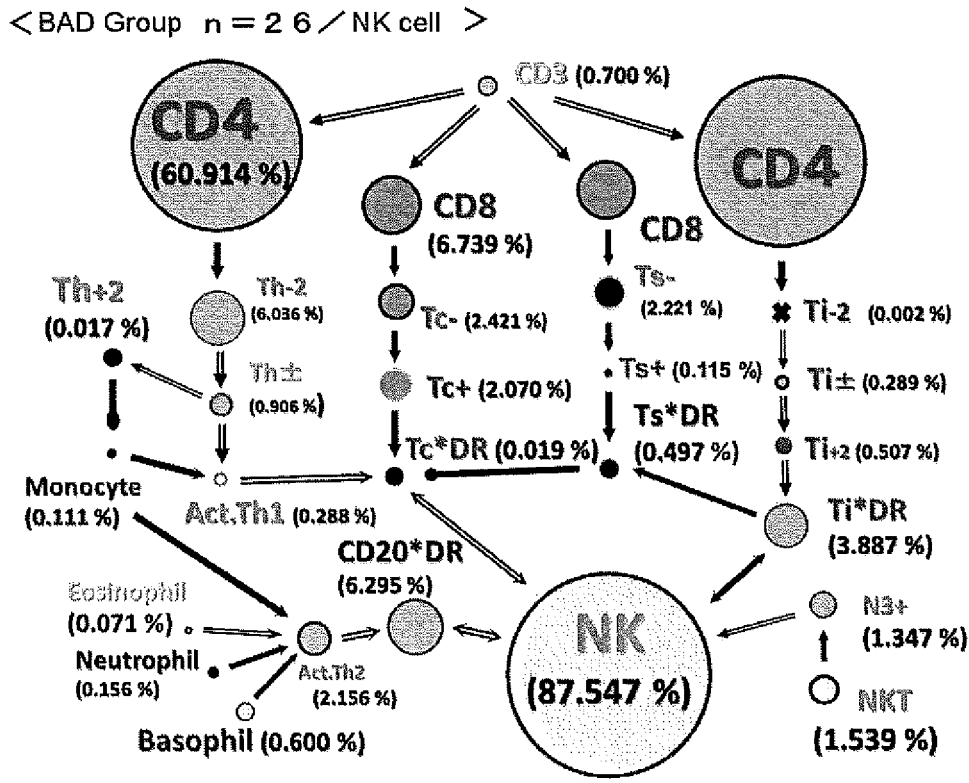
FIG. 23 represents an immunodynamics chart for NK cell in BAD group (n=26).

For cell-count data of 26 cases out of 137 cases sorted in BAD group, an analysis directed to NK-cell immunity was performed in a similar way as in <GOOD/higher X-axis group; n=54/NK cell>. The influence degrees were calculated and an immunodynamics chart was generated. The generated immunodynamics chart is shown in FIG. 23.

Neither TARM nor BARM have been established. There is stagnation and disruption at CD4, which should be dissolved by IL-2 administration, etc. Although there is a possibility that TARM and BARM will be recovered by NK-cell adoptive immunotherapy, this is not an appropriate therapy in the light of the immunodynamics chart.

BAD Group; n=26/T-Cell Immunity

Figure 24:
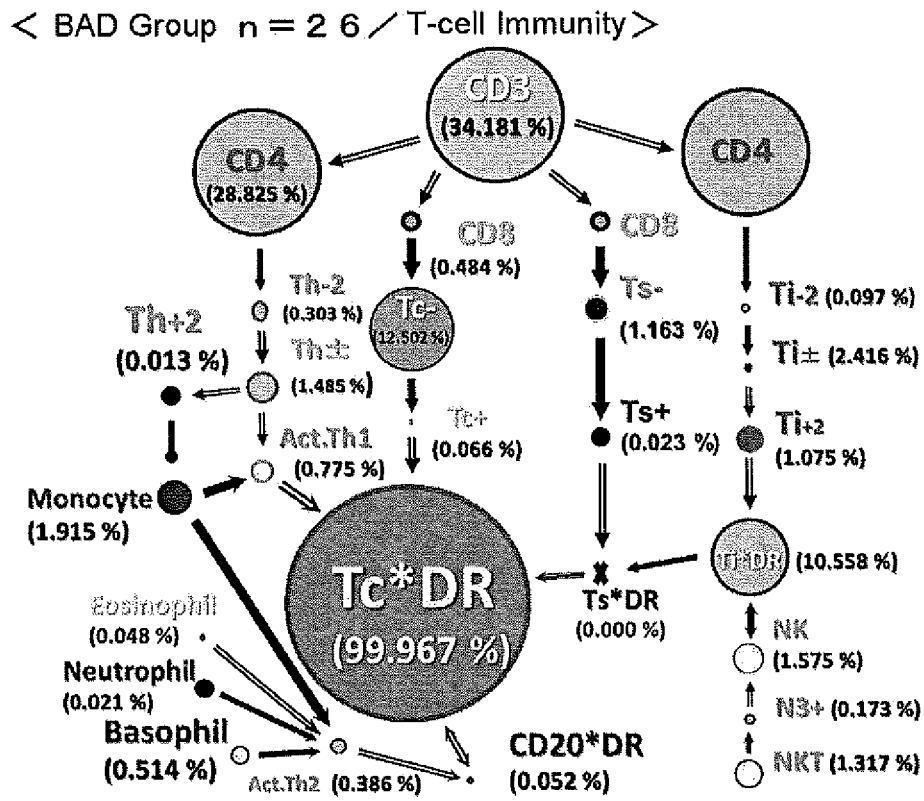
FIG. 24 represents an immunodynamics chart for T-cell immunity in BAD group (n=26).

For cell-count data of 26 cases out of 137 cases sorted in BAD group, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 24.

Neither TARM nor BARM have been established. Since there are stagnations at CD4 and CD3, it is at first necessary to activate the pathways by IL-2 administration, etc. to recover these stopped pathways. Then, therapies should be reconsidered according to the changes in immunodynamics.

BAD/Higher X-Axis Group; n=46/T-Cell Immunity

Figure 25:
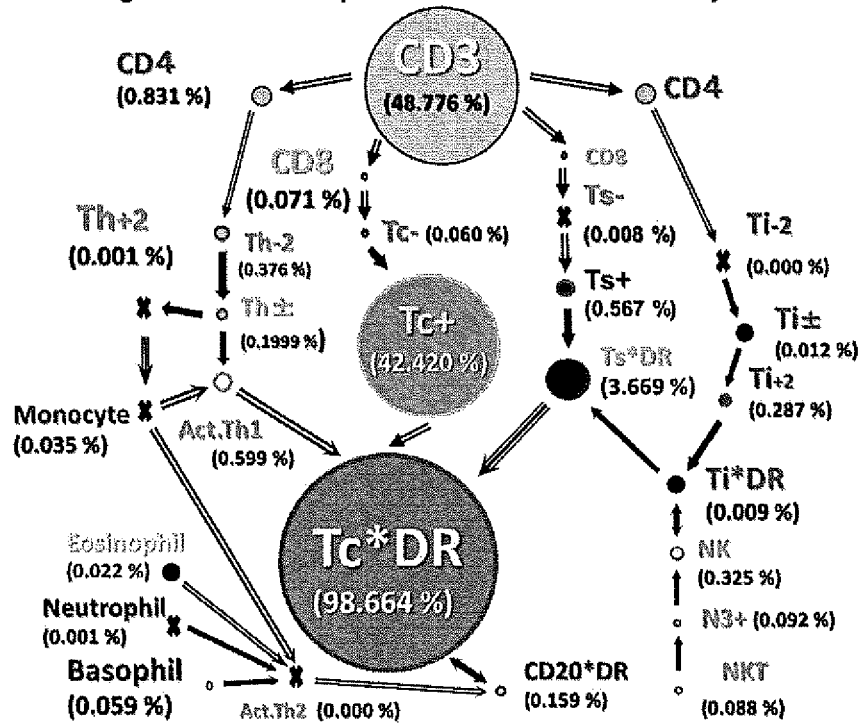
FIG. 25 represents an immunodynamics chart for T-cell immunity in BAD/higher X-axis group (n=46).

One hundred thirty-seven cases that have been sorted into BAD group are divided into three groups based on X-axis value, and for the cell-count data of 46 cases with high X-axis values, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 25.

Both TARM and BARM have been established. However, since CD3->CD8->Tc-->Tc+ pathway has been stagnated and stopped, the stagnation at CD3 and Tc+ should be improved by IL-2 administration, etc. in order for the pathway to smoothly go around. A therapy by administering an immune checkpoint inhibitor can also be expected to be effective. There is no need to be concerned about any autoimmune disease-like side effect since Act.Th1 is dominant (Act.Th1 (0.599%)>Act.Th2 (0.000%)). Note that although BARM has been established, CD20*DR is in negative relationship to Tc*DR and therefore ADCC activity may not be expected.

BAD/Middle X-Axis Group; n=46/NKT Cell

Figure 26:
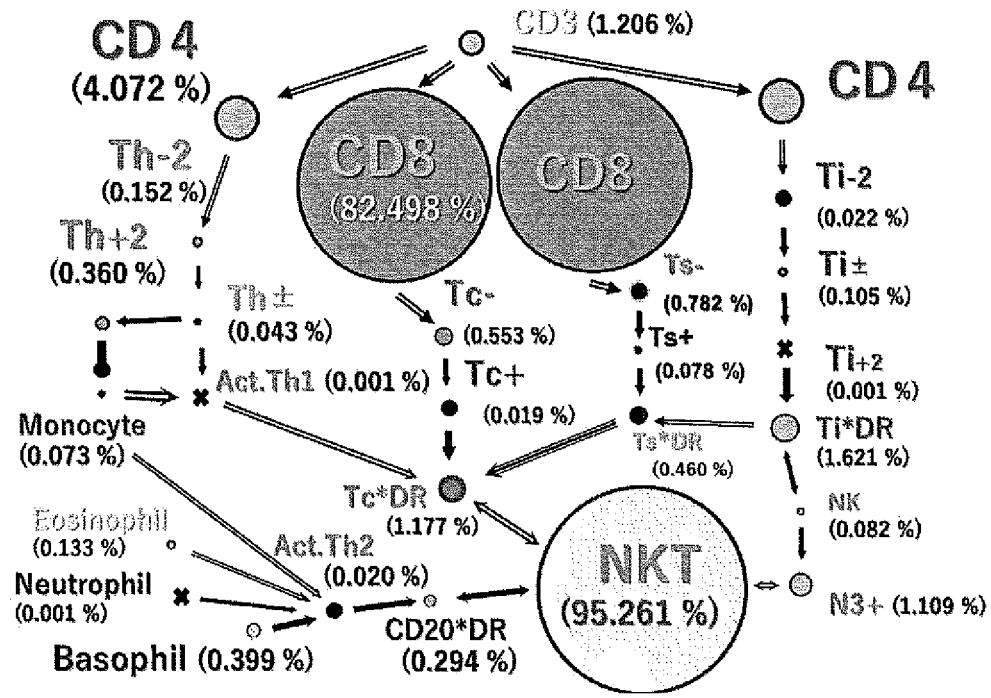
FIG. 26 represents an immunodynamics chart for NKT cell in BAD/middle X-axis group (n=46).

One hundred and thirty-seven cases that have been sorted into BAD group are divided into three groups based on X-axis value, and for the cell-count data of 46 cases with middle X-axis values, an analysis directed to NKT cell was performed in a similar way as in <BAD group: n=26/NKT cell>. The influence degrees were calculated and an immunodynamics chart was generated. The generated immunodynamics chart is shown in FIG. 26.

Although TARM has been established, there is significant stagnation at CD8. First of all, this stagnation should be improved by IL-2 administration, etc. Tc*DR is in positive relationship to NKT and is maintained. Since BARM has not been established, no ADCC activity can be expected.

Moreover, although Act.Th2 is dominant (Act.Th1 (0.001%)<Act.Th2 (0.020%)), Act.Th2->CD20*DR->NKT pathway has been disrupted and thus there is no need to be concerned about an autoimmunity-like side effect. Still, a discreet administration is desired when carrying out immunotherapy using an immune checkpoint inhibitor, etc. Monitoring by an immunodynamics chart monitor will be necessary.

BAD/Middle X-Axis Group; n=26/T-Cell Immunity

Figure 27:
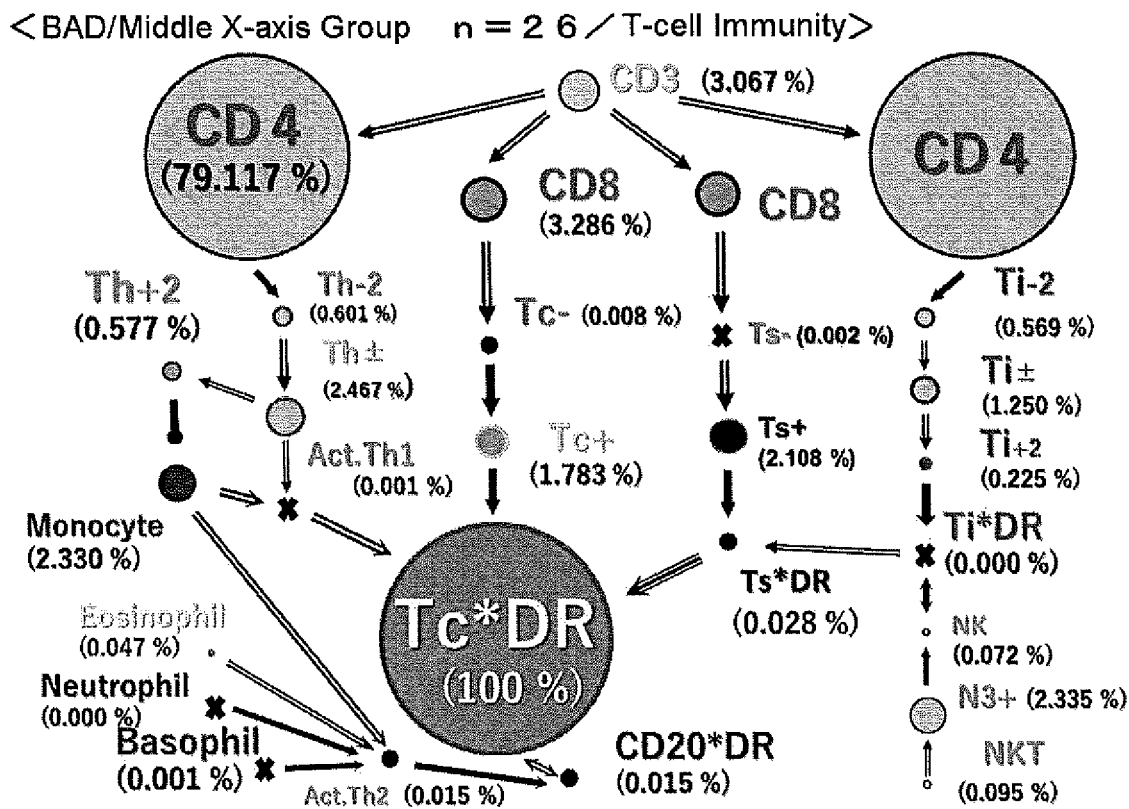
FIG. 27 represents an immunodynamics chart for T-cell immunity in BAD/middle X-axis group (n=26).

Among 137 cases that have been sorted into BAD group, for 26 cases of cell-count data with middle X-axis values, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 27.

TARM has barely been established, but there is significant stagnation at CD4. It is presumed that by relieving this stagnation by IL-2 administration, etc., the helper system will differentiate, proliferate or be enhanced, and the immunity will smoothly be turn around.

Moreover, although Act.Th2 is dominant (Act.Th1 (0.001%)<Act.Th2 (0.015%)), Act.Th2->CD20*DR pathway has been disrupted and thus there is no need to be concerned about an autoimmunity-like side effect. However, in order to carry out immunotherapy with discreetness, monitoring by an immunodynamics chart monitor will be necessary.

BAD/Lower X-Axis Group; n=45/B-Cell Immunity

Figure 28:
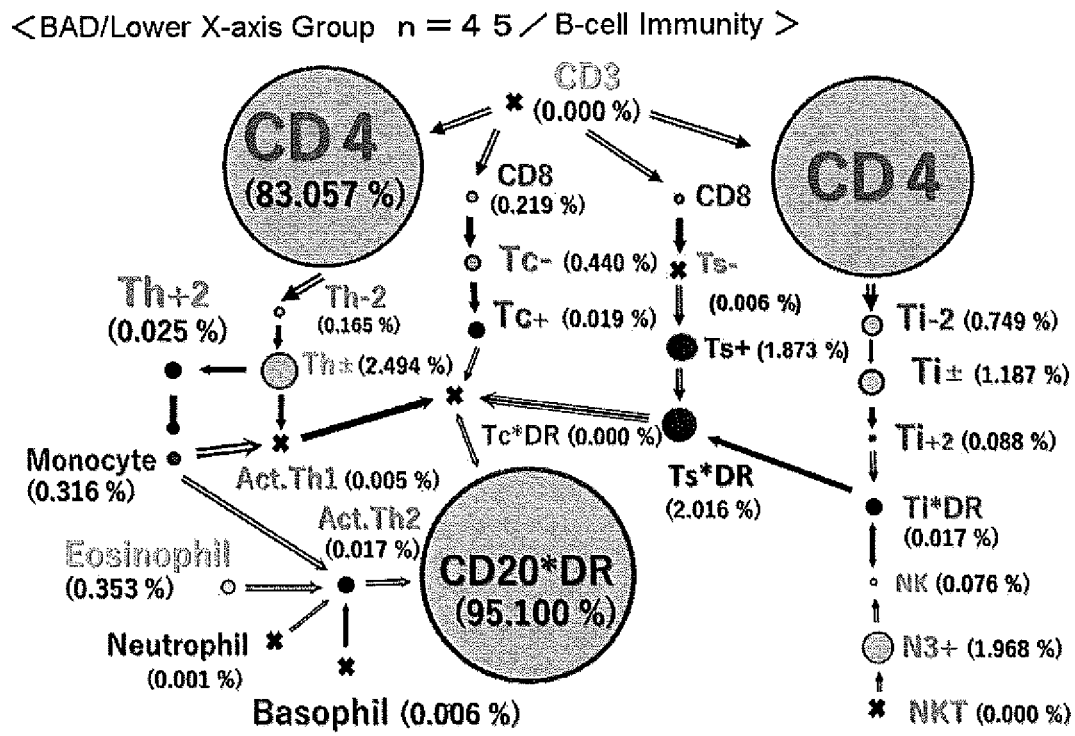
FIG. 28 represents an immunodynamics chart for B-cell immunity in BAD/lower X-axis group (n=45).

One hundred and thirty-seven cases that have been sorted into BAD group are divided into three groups based on X-axis value, and for the cell-count data of 45 cases with low the X-axis values, an analysis directed to B-cell immunity was performed in a similar way as in <GOOD group; n=26/B-cell immunity>. The influence degrees were calculated and an immunodynamics chart was generated. The generated immunodynamics chart is shown in FIG. 28.

BARM has been established, whereas TARM has not. Moreover, there is significant stagnation at CD4 and the pathway has been disrupted against Act.Th1 (0.005%). It is presumed that promoting of differentiation and proliferation by IL-2 administration, etc. will increase the influence degree of Act.Th1, which brings TARM to be established.

Because Th2 is dominant (Act.Th1 (0.005%)<Act.Th2 (0.017%)), it is necessary to be careful when using an immune checkpoint inhibitor.

BAD/Lower X-Axis Group; n=45/T-Cell Immunity

Figure 29:
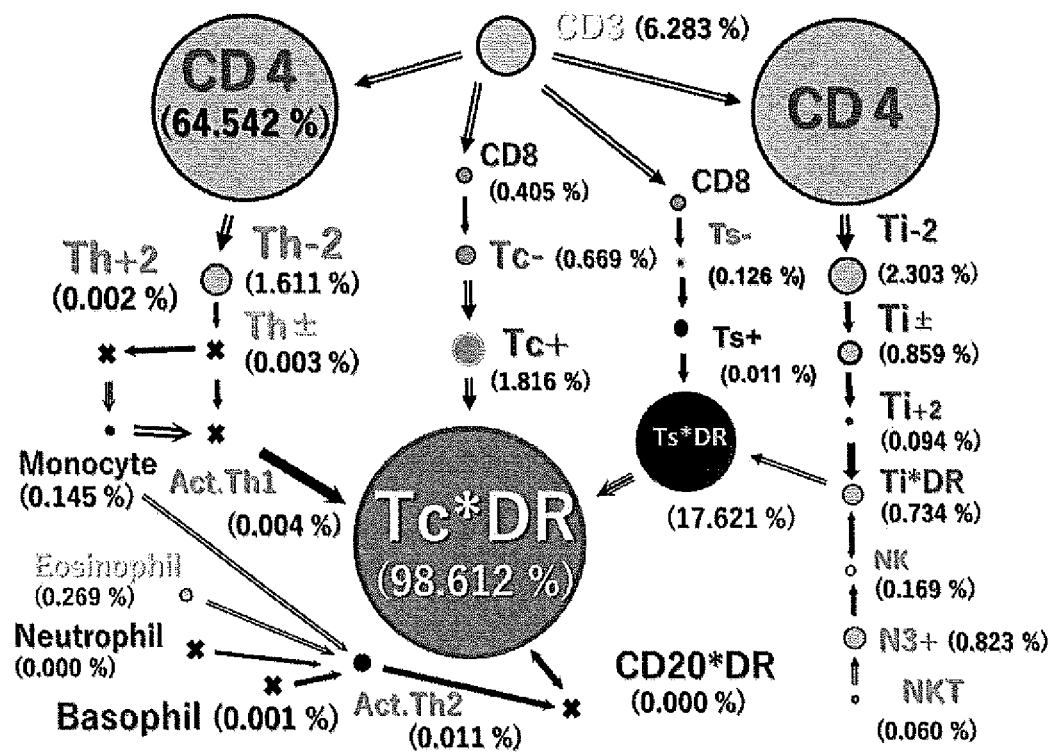
FIG. 29 represents an immunodynamics chart for T-cell immunity in BAD/lower X-axis group (n=45).

One hundred and thirty-seven cases that have been sorted into BAD group are divided into three groups based on X-axis value, and for the cell-count data of 45 cases with low X-axis values, an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 29.

Neither TARM nor BARM have been established. Moreover, there is significant stagnation at CD04. It is essential to dissolve this stagnation by IL-2 administration, etc. to promote differentiation and proliferation of helper T cells. Since Ts*DR is at a considerably high level (17.621%), immunotherapy for suppressing it is also promising.

BAD/Middle Y-Axis Group; n=46/T-Cell Immunity

Figure 30:
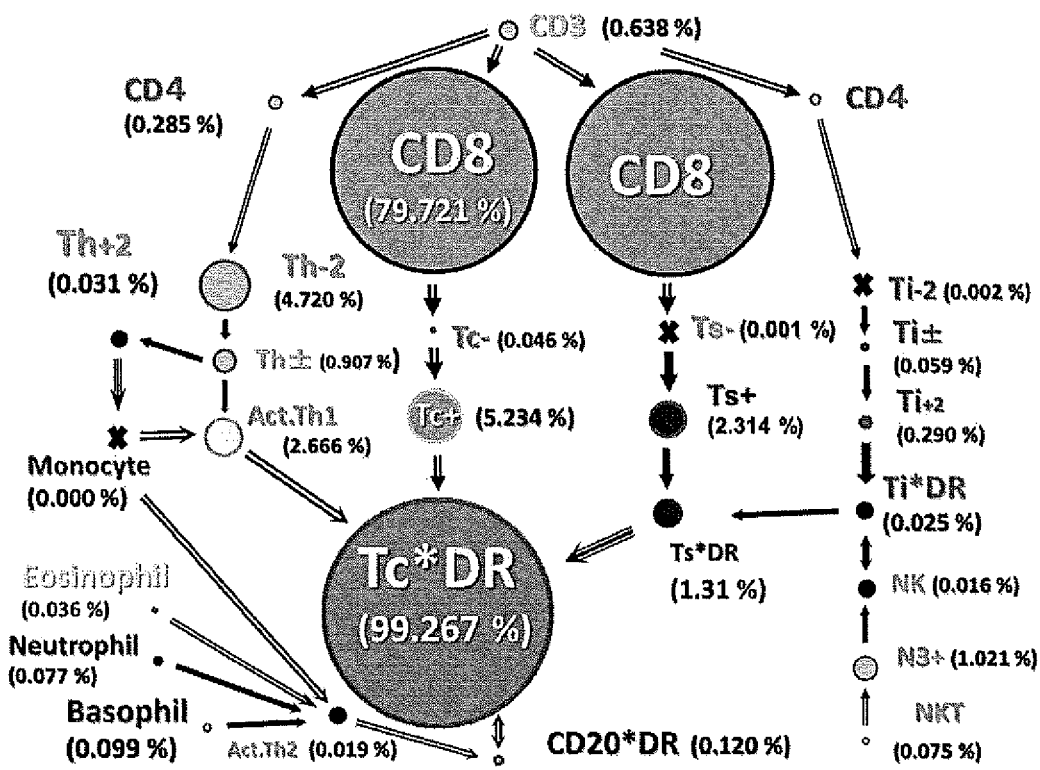
FIG. 30 represents an immunodynamics chart for T-cell immunity in BAD/middle Y-axis group (n=46).

One hundred and thirty-seven cases that have been sorted into BAD group were divided into three groups based on Y-axis value, and for the cell-count data of 46 cases with middle Y-axis value , an analysis directed toward T-cell immunity was performed in a similar way as in <GOOD/lower X-axis group; n=54/T-cell immunity>. The influence degrees were calculated and an immunodynamics chart was generated. The generated immunodynamics chart is shown in FIG. 30.

Both TARM and BARM have been established. However, there is significant stagnation at CD8, it is essential to promote differentiation and proliferation by IL-2 administration, etc. Regardless of the stagnation at CD8, the pathway to Tc*DR has not been disrupted and is still open, and therefore it is considered that the use of an immune checkpoint inhibitor from the beginning will be considerably effective. Moreover, since Act.Th1 is dominant (Act.Th1 (2.666%)>Act.Th2 (0.019%)), there would be no concern about an autoimmune disease-like side effect.

BAD/Middle Y-Axis Group; n=46/NKT Cell

Figure 31:
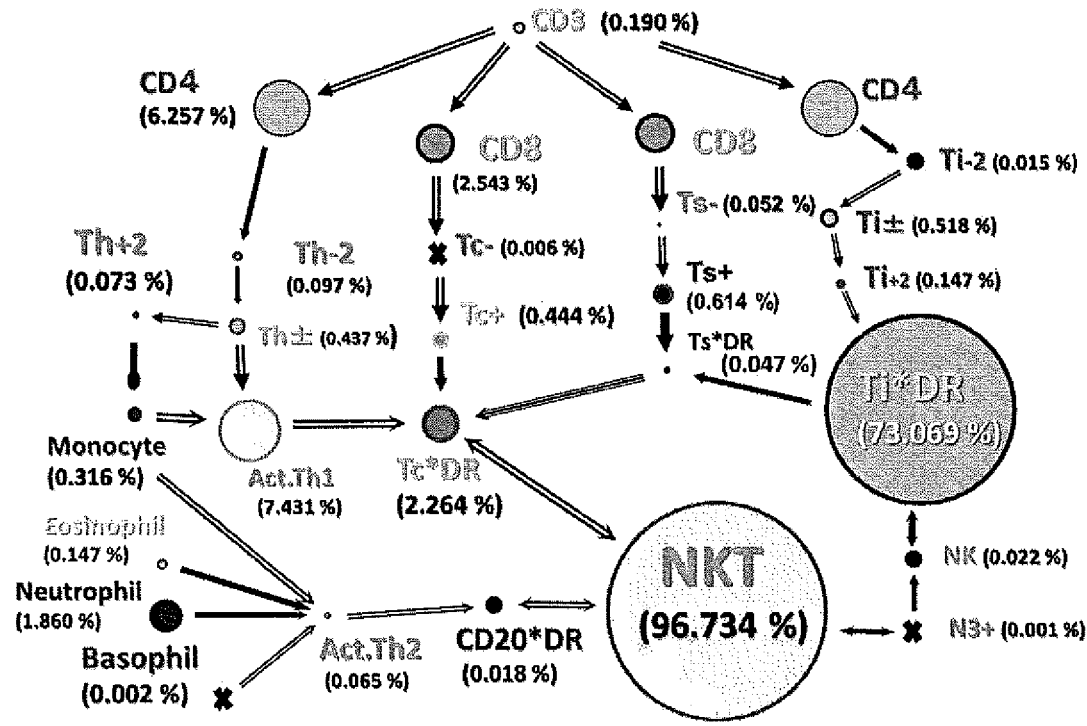
FIG. 31 represents an immunodynamics chart for NKT cell in BAD/middle Y-axis group (n=46).

One hundred and thirty-seven cases that have been sorted into BAD group were divided into three groups based on Y-axis value, and for the cell-count data of 46 cases with middle Y-axis value, an analysis directed to NKT cell was performed in a similar way as in <BAD group; n=26/NKT cell>. The influence degrees were calculated and an immunodynamics chart was generated. The generated immunodynamics chart is shown in FIG. 31.

Both TARM and BARM have been established, and NKT activity and ADCC activity have also been established. However, since there is stagnation and disruption at Ti*DR, immunity will be more effective by any therapy for dissolving the stagnation of Ti*DR and promoting differentiation and proliferation of helper lymphocytes. It is also possible that Ti*DR will be suppressed by NK-cell adoptive immunotherapy.

This is suitable for an application of an immune checkpoint inhibitor or NKT-cell adoptive immunotherapy. Since Th1 is dominant (Act.Th1 (7.431%)>Act.Th2 (0.065%)), there is presumably no concern about side effects.

BAD/Higher Y-Axis Group; n=45/B-Cell Immunity

Figure 32:
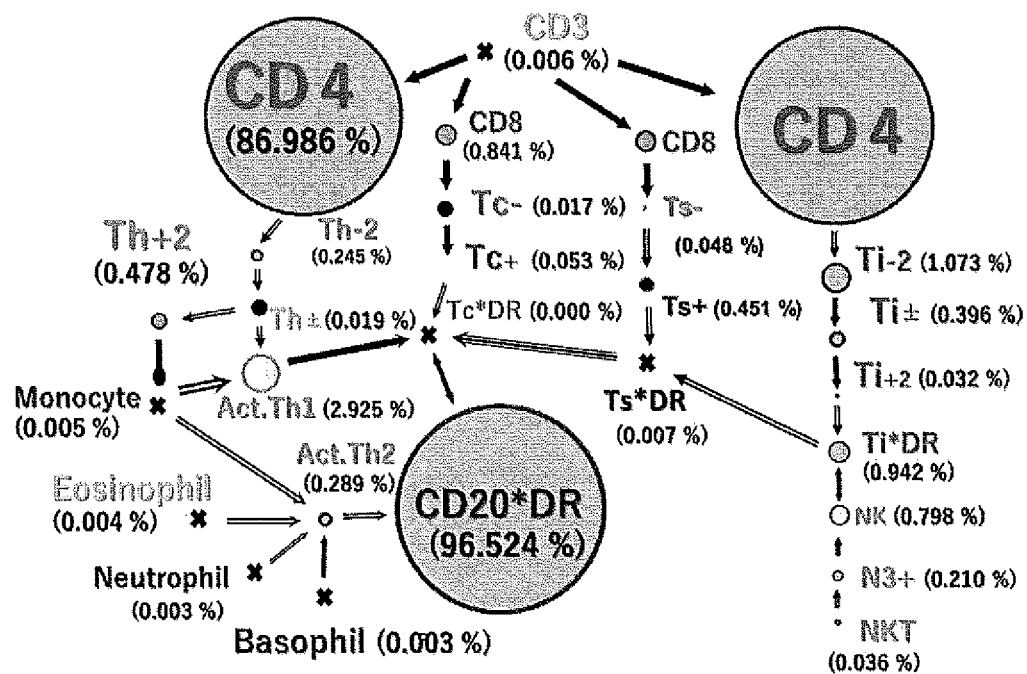
FIG. 32 represents an immunodynamics chart for B-cell immunity in BAD/higher Y-axis group (n=45).

One hundred and thirty-seven cases that have been sorted into BAD group were divided into three groups based on Y-axis value, the cell-count data of 45 cases with high Y-axis values, an analysis directed to B-cell immunity was performed in a similar way as in <GOOD group; n=26/B-cell immunity>. The influence degrees were calculated and an immunodynamics chart was generated. The generated immunodynamics chart is shown in FIG. 32.

There is significant stagnation at CD4. BARM has been established, whereas TARM has not. Because BARM has been established, it is necessary to be careful about a side effect which may be caused by using an immune checkpoint inhibitor.

BAD/Lower Y-Axis Group; n=45/B-Cell Immunity

Figure 33:
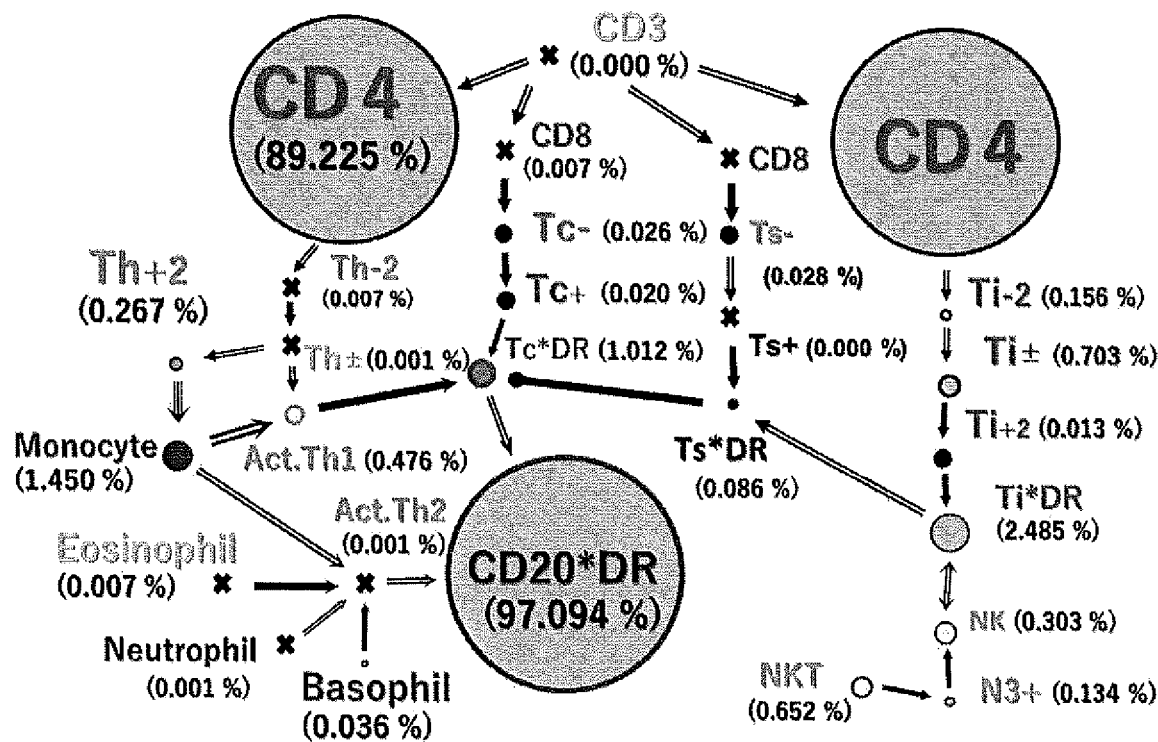
FIG. 33 represents an immunodynamics chart for B-cell immunity in BAD/lower Y-axis group (n=45).

One hundred and thirty-seven cases that have been sorted into BAD group were divided into three groups based on Y-axis value, and for the cell-count data of 45 cases with low Y-axis values, an analysis directed to B-cell immunity was performed in a similar way as in <GOOD group; n=26/B-cell immunity>. The influence degrees were calculated and an immunodynamics chart was generated. The generated immunodynamics chart is shown in FIG. 33.

There is significant stagnation at CD4. BARM has been established, whereas TARM has not. ADCC (Monocyte->Act.Th2->CD20*DR<=>Tc*DR) has also been established. Dissolving of this stagnation at CD4 and activating of ADCC will turn the anti-cancer (anti-tumor) immunity effective. Since Th1 is dominant (Act.Th1 (0.476%)>Act.Th2 (0.001%)), there is presumably no concern about side effects by immune checkpoint inhibitor.

n=29/T-Cell Immunity

Figure 34:
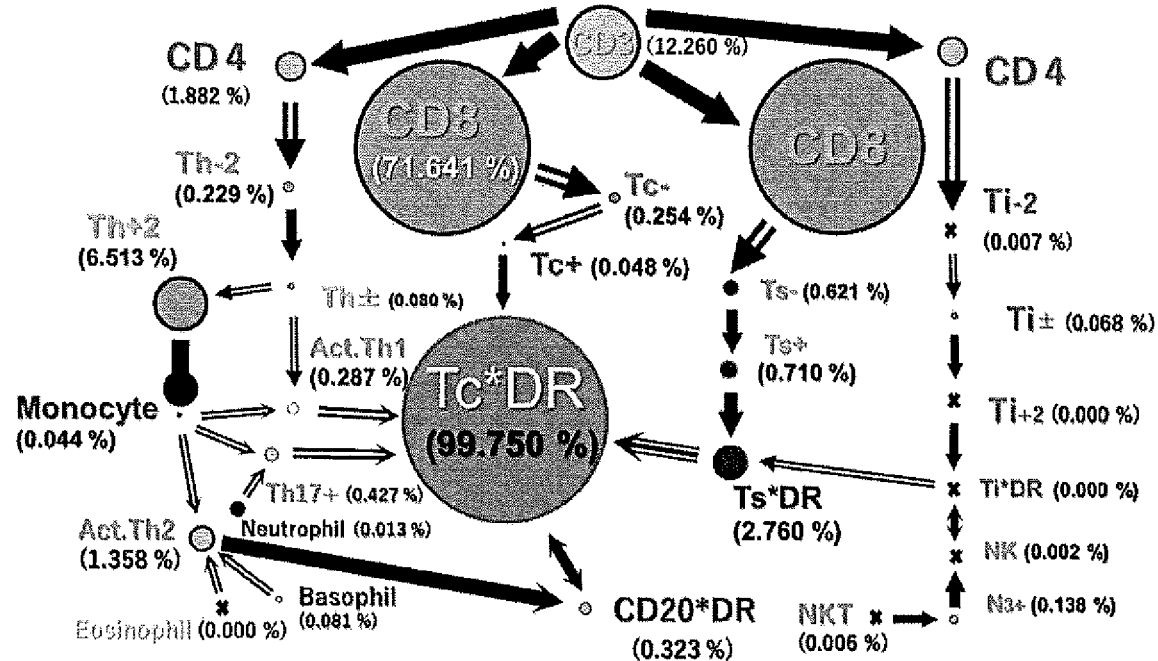
FIG. 34 represents an immunodynamics chart for T-cell immunity (n=29).

A multiple regression analysis was performed for the cell-count data of 29 cases, using Tc*DR lymphocyte as objective variable, and Th17+lymphocyte, CD3-positive lymphocyte, CD4-positive lymphocyte, CD8-positive lymphocyte, CD20*DR lymphocyte, Th± lymphocyte, Th–2 lymphocyte, Th+2 lymphocyte, Act.Th1 lymphocyte, Act.Th2 lymphocyte, Ti*DR lymphocyte, Ti± lymphocyte, Ti–2 lymphocyte, Ti+2 lymphocyte, Tc– lymphocyte, Tc+ lymphocyte, Ts*DR lymphocyte, Ts– lymphocyte, Ts+lymphocyte, NK cell, NKT cell, N3+ cell, monocyte, basophil, eosinophil and neutrophil as explanatory variables. The standard partial regression coefficients of the immunocompetent cells obtained in this analysis were ranked in descending order according to their absolute values, a multiple regression analysis using Tc*DR lymphocyte as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 34.

TARM has been established, whereas BARM has not. There is significant stagnation at CD8, and in order to further activate the pathway from CD3 to Tc*DR and make this pathway open without any stagnation, therapy such as administering a cytokine such as IL-2 can be considered. After observing any changes in immunodynamics by this therapy, mainly changes in the degree of activation of T-cell immunity, the next therapeutic means shall be considered.

Moreover, in the immunodynamics chart, Monocyte->Th17+->Tc*DR pathway has been established, which is weak but still contributing to anti-cancer (anti-tumor) immunity. Note that the influence degree of neutrophil is as low as 0.013% and it may have a low influence. Here, if interleukin-17A/F (1L-17A/F), etc. is produced by being stimulated by various treatment such as fractalkines (either administered or produced in the body), and a pathway of:

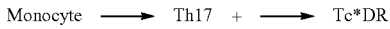

Neutrophil is further activated, an enhanced differentiation, activation or proliferation towards Tc*DR, i.e., an enhancement of anti-cancer (anti-tumor) effect can be expected.

Besides, in the context of anti-cancer (anti-tumor) immunity, it is necessary that T-cell immunity has been established, though B-cell immunity is better if not established. This is because it may cause an allergic or autoimmunity-like side effect. Note that this shall not apply where antibody dependent cellular cytotoxicity (ADCC) is to be expected.

n=27/B-Cell Immunity

Figure 35:
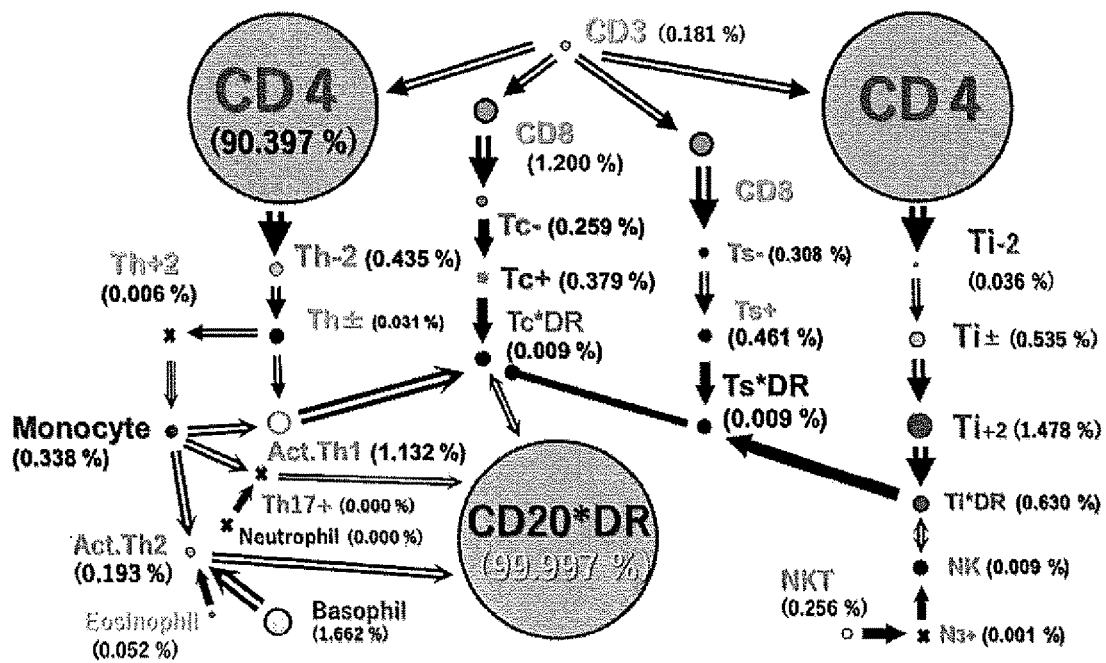
FIG. 35 represents an immunodynamics chart for B-cell immunity (n=27).

A multiple regression analysis was performed for the cell-count data of 27 cases using CD20*DR lymphocyte as objective variable, and Th17+ lymphocyte, CD3-positive lymphocyte, CD4-positive lymphocyte, CD8-positive lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil, eosinophil and neutrophil as explanatory variables. The standard partial regression coefficients of the immunocompetent cells obtained in this analysis were ranked in descending order according to their absolute values, a multiple regression analysis using CD20*DR lymphocyte as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 35.

There is stagnation of differentiation and proliferation at CD4. Although the pathways of helper T cells are open, they are hindered and tapering off. TARM has barely been established.

In order to improve this to be further effective, it is necessary to either activate T-cellular antigen recognition mechanism by interferon α, dendritic cell vaccine therapy, or fungal supplements for enhancing Tc*DR, or to carry out immunotherapy for activating and enhancing CD3->CD8->Tc-->Tc+->Tc*DR pathway by 1L-2 or immune checkpoint inhibitors, etc.

Since BARM pathway has been established, there is concern for development of an allergic or autoimmunity-like side effect. However, T-cell immunity is dominant (Act.Th1 (1.132%)>Act.Th2 (0.193%)), the possibility of developing a side effect is presumably low. Nevertheless, because the dominance may be altered to Act.Th1<Act.Th2 by some treatment, treatment should be carried out under strict observation while generating and monitoring immunodynamics charts as appropriate.

In addition, although Monocyte->Th17+->CD20*DR pathway has also been established, Th17+ lymphocyte is 0.000% and extremely low, and is in a negative relationship with Th17+, the possibility of developing an allergic or autoimmunity-like side effect is low, with very little concern for such side effects. However, depending on the treatment, Neutrophil->Th17+->CD20*DR pathway may be activated and the side effects such as fever or allergic skin disorders may be developed. Therefore, a similar strict observation is essential.

Furthermore, since basophil is at relatively high level as 1.662%, which may cause an unexpected immediate allergic response. Therefore, immunotherapy should be carried out with discretion under a sufficient observation. If the influence degree of basophil towards Act.Th2 is further increased by a treatment, the treatment must be stopped.

n=27/NKT Cells

Figure 36:
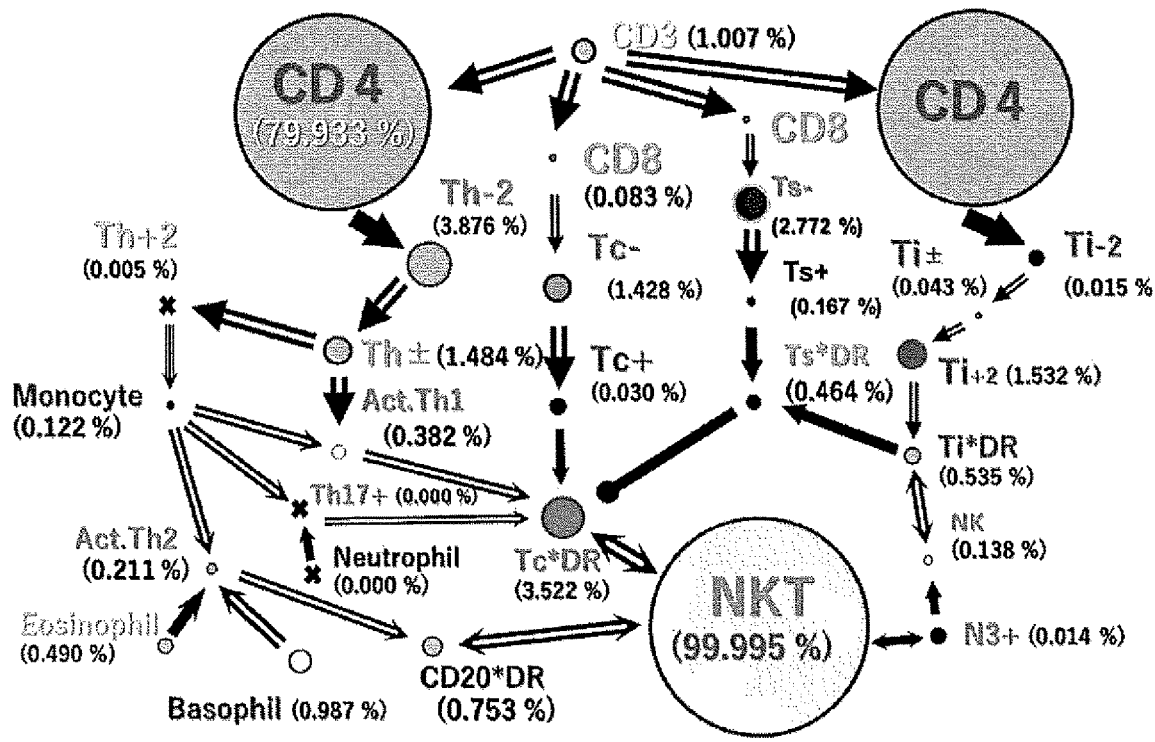
FIG. 36 represents an immunodynamics chart for NKT cells(n=27).

A multiple regression analysis was performed for the cell-count data of 27 cases using NKT cell as objective variable, and Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, N3+ cell, monocyte, basophil, eosinophil and neutrophil as explanatory variables. The standard partial regression coefficients of the immunocompetent cells obtained in this analysis were ranked in descending order according to their absolute values, a multiple regression analysis using NKT cell as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 36.

There is stagnation of differentiation and proliferation at CD4-positive lymphocyte, though TARM has been established.

In order to bring Tc*DR to differentiate, be activated or proliferate to enhance anti-tumor immunity, it is necessary to enhance the pathway towards Tc*DR by, e.g., administering α-galactosylceramide (α-GalCer) or NKT cell-activating adoptive immunotherapy.

The influence degree of each immunocompetent cell in Monocyte->Th17+->Tc*DR pathway is extremely low, and the influence degree of neutrophil is also 0.000% and a negative factor, and it is therefore not an enhancing factor. Here, if IL-17 NF, etc. is produced by stimulation by various treatment such as fractalkines (either administered or produced in the body) and a pathway of Neutrophil->Th17+->Tc*DR pathway is established, the differentiation, activation and proliferation towards Tc*DR will be enhanced, and an anti-tumor effect can be expected.

The influence degree of basophil is slightly high as 0.987%, and there is a concern about development of immediate allergy which needs to be noted. If the influence degree of basophil is increased by a treatment, it is necessary to consider stopping or discontinuing the treatment.

n=28/NK Cell

Figure 37:
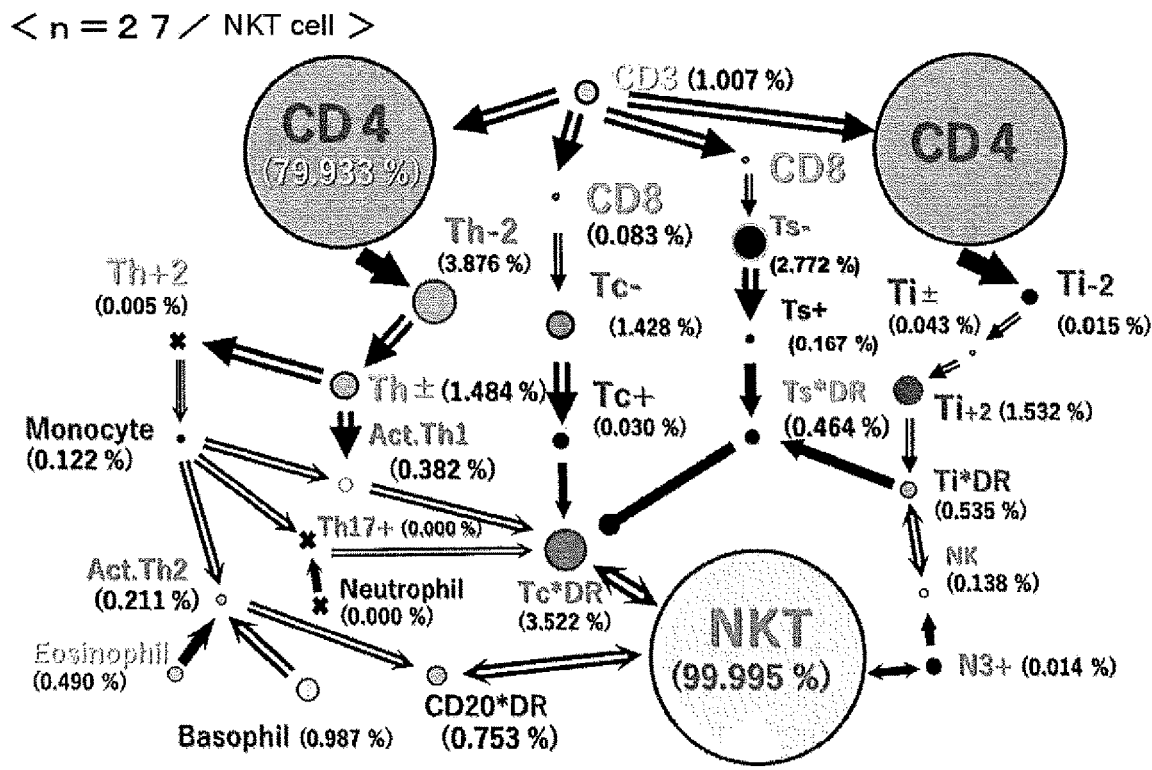
FIG. 37 represents an immunodynamics chart for NK cell (n=28).

A multiple regression analysis was performed for the cell-count data of 28 cases using NK cell as objective variable, and Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NKT cell, N3+ cell, monocyte, basophil, eosinophil and neutrophil as explanatory variables. The standard partial regression coefficients of the immunocompetent cells obtained in this analysis were ranked in descending order according to their absolute values, a multiple regression analysis using NK cell as objective variable was repeatedly performed in similar way as in GOOD/lower X-axis group/T-cell immunity, and the influence degrees were calculated for all immunocompetent cells and an immunodynamics chart was generated. The generated immunodynamics chart is shown in FIG. 37.

There is stagnation of differentiation and proliferation at CD4-positive lymphocyte. The influence degree of Tc*DR is extremely low at 0.003%, and no anti-cancer (anti-tumor) immunity can be expected. Although TARM has weakly been established, Tc*DR lymphocyte is in negative relationship to NK and so-called NK cell activity (Monocyte->Act.Th1->Tc*DR<=>NK) has not been established. B-cellular antigen recognition mechanism (Monocyte->Act.Th2->CD20*DR<=>NK) has been disrupted between Act.Th2 and CD20*DR, and CD20*DR is also in negative relationship to NK, antibody dependent cellular cytotoxicity (ADCC: Monocyte->Act.Th2->CD20*DR <=>NK) has not be established.

In order to activate and enhance anti-cancer (anti-tumor) immunity, it is necessary to recover these stopped/disrupted pathways by, e.g., 1L-2 administration or activated NK-cell adoptive immunotherapy. Here, it is important to confirm the increase in Tc*DR influence degree derived from the treatment by generating and monitoring immunodynamics chart.

With respect to the influence degrees of Act.Th1 and Act.Th2, Act.Th2 is dominant (Act.Th1 (0.121%)<Act.Th2 (2.142%)), and thus it is important to take strict care not to facilitate B-cell antigen-producing immunity and thereby cause an onset of an allergic or autoimmunity-like disease. To this end, it becomes essential to monitor immunodynamics.

Besides, the pathway:

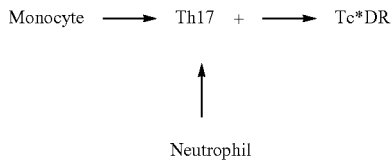

has weakly been established, a care needs to be taken for development of psoriasiform dermatitis and other skin allergy-like diseases.

In various immunotherapies, in particular, a single or combined therapy with an immune checkpoint inhibitor, a care should be taken when eosinophil, basophil, etc. are in positive relationship to NK and the influence degree is increased. In particular, when basophil is in positive relationship and the influence degree is increased, a special care is required because there is a concern for development of immediate allergic reaction.

n=28/Basophil2

A multiple regression analysis was performed for the cell-count data of 28 cases using basophil as objective variable, and Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, eosinophil and neutrophil as explanatory variables. The standard partial regression coefficients of the immunocompetent cells obtained in this analysis were ranked in descending order according to their absolute values, a multiple regression analysis using basophil as objective variable was repeatedly performed in a similar way as in <GOOD group; n=26/basophil>, and the influence degrees were calculated for all immunocompetent cells and an immunodynamics chart was generated. The generated immunodynamics chart is shown in FIG. 38.

As mentioned with respect to FIG. 12, in an immunodynamics chart directed to basophil, when Th1-immunity (Monocyte->Act.Th1->Tc*DR<=>Basophil) or Th2-immunity (Monocyte->Act.Th2->CD20*DR<=>Basophil) is established, it is a severe case with immediate allergic reaction that would be an indication of an adrenaline intramuscular injection. A immunodynamics chart directed to basophil is an essential immunodynamics chart, because any severe allergic side effect can be predicted by generating it.

Figure 38:
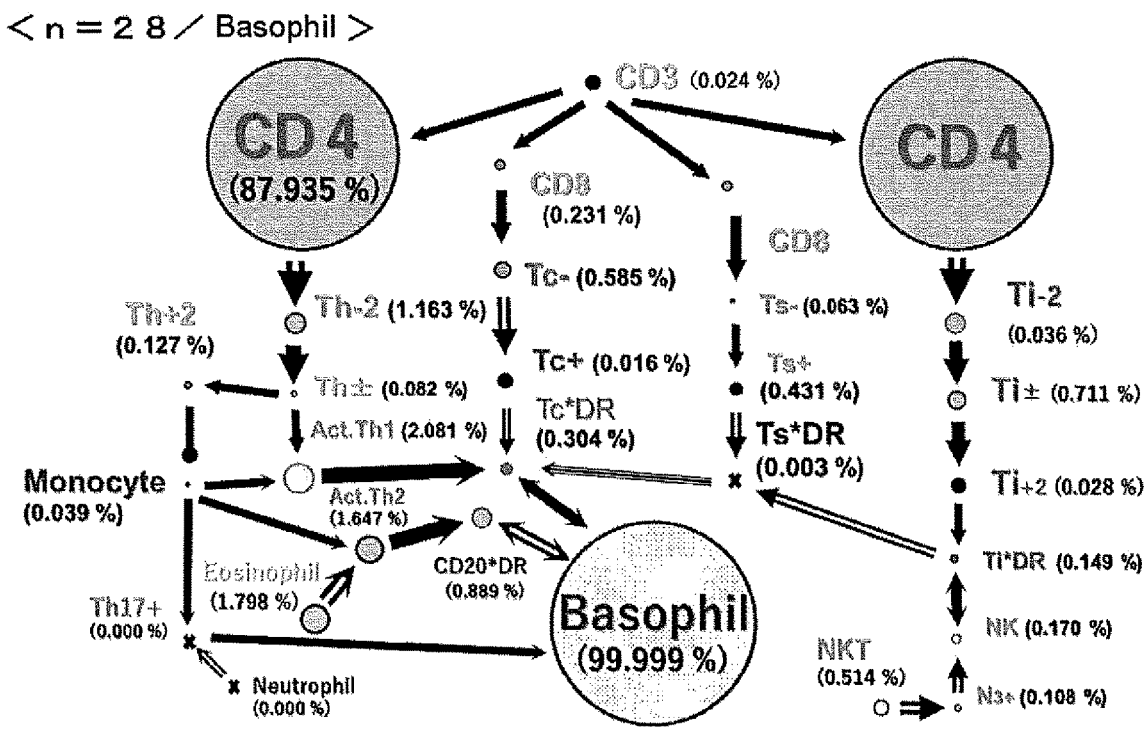
FIG. 38 represents an immunodynamics chart for basophil (n=28).

In FIG. 38, Th1-immunity (Monocyte->Act.Th1->Tc*DR<=>Basophil), Th2-immunity (Monocyte->Act.Th2->CD20*DR<=>Basophil), and Monocyte->17+->Basophil pathway are disrupted, and thus there would be very little risk of an allergic reaction being developed.

n=27/Eosinophil

Figure 39:
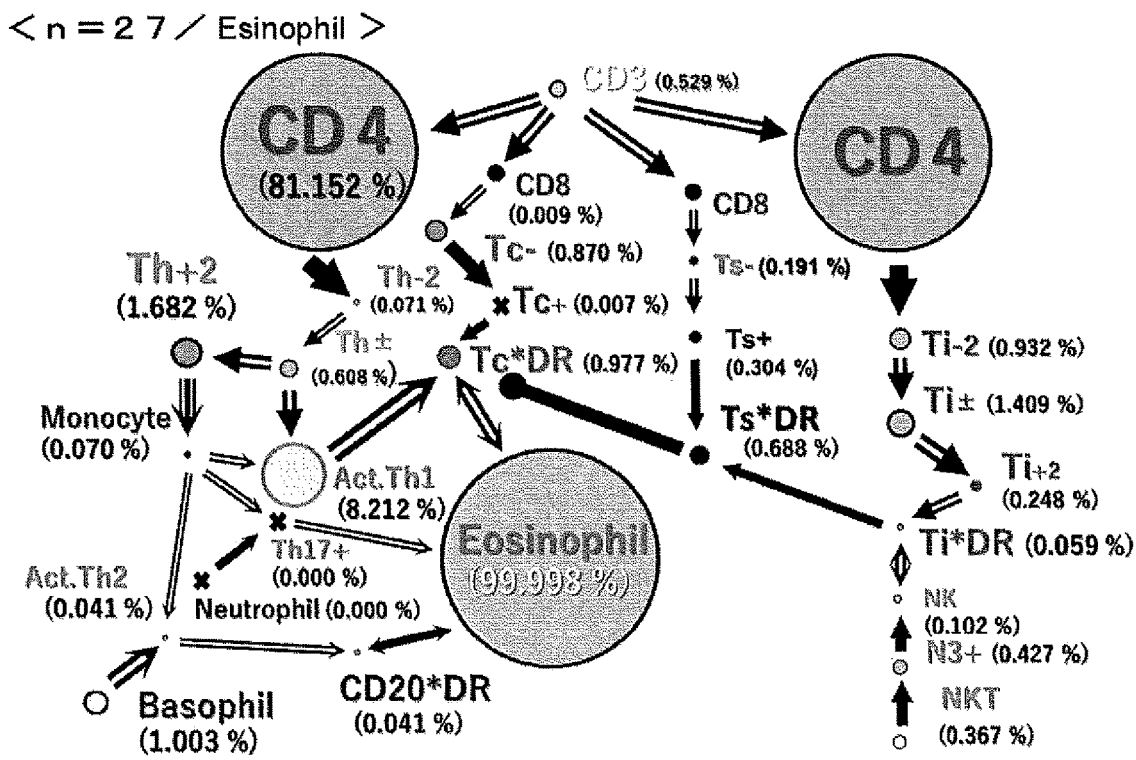
FIG. 39 represents an immunodynamics chart for eosinophil(n=27).

A multiple regression analysis was performed for the cell-count data of 27 cases using eosinophil as objective variable, and Th17+lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil and neutrophil as explanatory variables. The standard partial regression coefficients of the immunocompetent cells obtained in this analysis were ranked in descending order according to their absolute values, a multiple regression analysis using eosinophil as objective variable was repeatedly performed in a similar way as in <GOOD group; n=26/eosinophil>, and the influence degrees were calculated for all immunocompetent cells and an immunodynamics chart was generated. The generated immunodynamics chart is shown in FIG. 39.

There is stagnation of differentiation and proliferation at CD4. Specific immunity that consists of Th1-antigen recognition mechanism (Monocyte->Act.Th1->Tc*DR) to induce activated cytotoxic T cell (Tc*DR) has been established. Moreover, the influence degrees of Act.Th1 and Act.Th2 are Act.Th1 (8.212%)>Act.Th2 (0.041%), and T-cell immunity is dominant over B-cell immunity.

Activated regulatory T cell (Th+2), which is involved in immune suppression, is at relatively high level as 1.682%, which suppresses monocyte to an extremely low level. When the use of Tc*DR-inducing immunity is considered, it is also considered to use Th+2-suppressing agent such as ipilimumab (Trade name: Yervoy®) while taking sufficient care about following points:

The pathway in which Th17+ is involved (Monocyte->Th17+->Eosinophil) has also been established, though the influence degree of Th17+ is 0.000%, and Th17+ is in negative relationship to Neutrophil. Thus, Th17+ is poorly involved.

It needs to be noted here that the influence degree of basophil is relatively high as 1.003%. It needs to be noted that, because Monocyte->Act.Th2->CD20*DR pathway is open, treatment might bring CD20*DR into positive relationship to eosinophil, which will increase the risk for the onset of severe allergy.

n=27/Neutrophil

Figure 40:
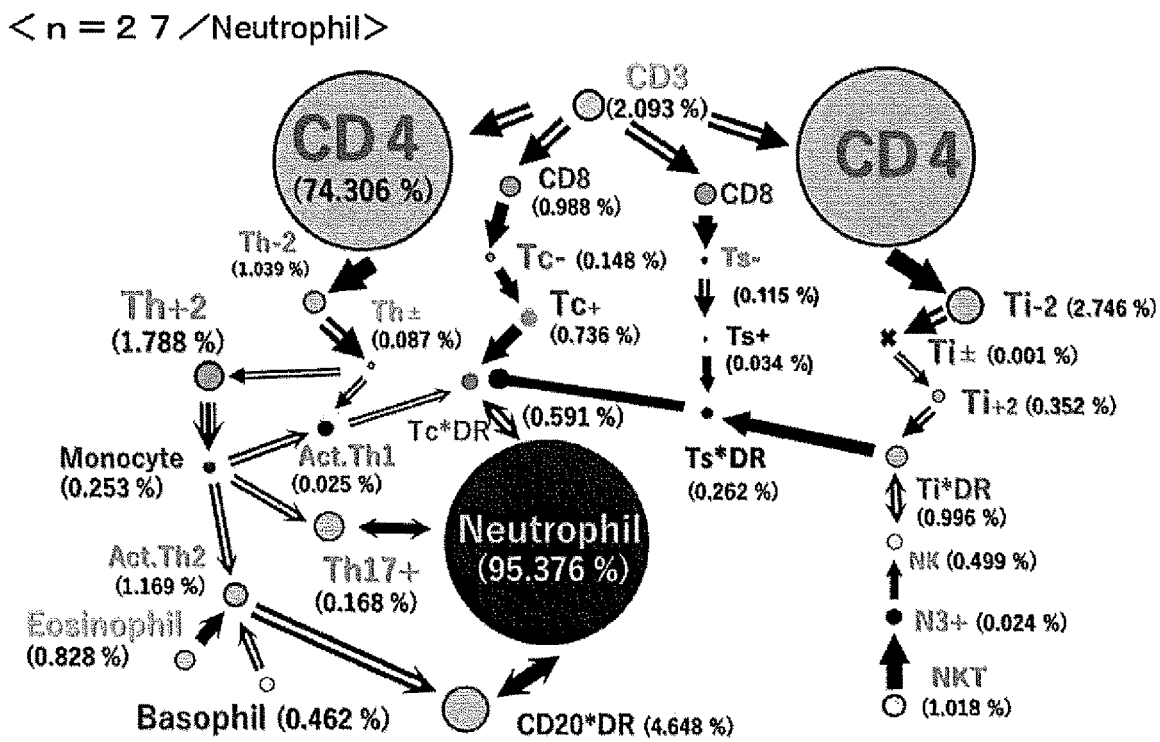
FIG. 40 represents an immunodynamics chart for neutrophil(n=27).

A multiple regression analysis was performed the cell-count data of 27 cases using neutrophil as objective variable Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc− lymphocyte, Tc+ lymphocyte, Tc*DR lymphocyte, Ts*DR lymphocyte, Ts− lymphocyte, Ts+ lymphocyte, NK cell, NKT cell, N3+ cell, monocyte, basophil and eosinophil as explanatory variables. The standard partial regression coefficients of the immunocompetent cells obtained in this analysis were ranked in descending order according to their absolute values, a multiple regression analysis using neutrophil as objective variable was repeatedly performed in a similar way as in <GOOD group; n=26/neutrophil>, and the influence degrees were calculated for all immunocompetent cells and an immunodynamics chart was generated. The generated immunodynamics chart is shown in FIG. 40.

There is stagnation of differentiation and proliferation at CD4. Anti-cancer (anti-tumor) immunity (Monocyte->Act.Th1->Tc*DR<=>Neutrophil) has weakly been established. In this immunodynamics chart, the influence degree of Th+2 as high as 1.788% is noticeable. In order to activate this pathway, not only a vaccine therapy, but also Th+2-surressing therapy may be effective.

B-cell immunity (Monocyte->Act.Th2->CD20*DR), which is a Th2-system, is open, and CD20*DR is so far in negative relationship to neutrophil, and thus there seems no issue of side effect. However, if it turns to positive relationship due to a treatment, serious side effects (e.g., inflammatory autoimmune diseases) may be developed. Therefore, monitoring by an immunodynamics chart is essential. In pathways in which Th17+ is involved, Th17+ is in negative relationship to neutrophil, and thus there seems no concern about an inflammatory autoimmune dermatitis, etc. being developed.

Example 5

Providing Subjects with Immunodynamics-Related Information (1)

Certain cell-count of each of multiple types of immunocompetent cells in blood collected from a subject was assigned into the discriminant function obtained in Example 2, the given discriminant score belonged to GOOD/middle X-axis group. Therefore, as the immunodynamics-related information for the subject about for T-cell immunity, the immunodynamics chart described in FIG. 7 is presented.

With reference to FIG. 7, it can be found that although both TARM and BARM have been established, differentiation and proliferation are stagnated at CD8, and the pathway from CD8 to Tc*DR has been disrupted. Treatments for this subject may include activation/enhancement of CD3->CD8->Tc-->Tc+->Tc*DR pathway by IL-2 administration, etc. Moreover, because the monocyte/macrophage system is at an extremely low level, this also needs to be activated. Th+2 is at a low level and thus does not need to be suppressed. Ts*DR is at a high level, and, if no improvement is achieved by the aforementioned treatment, Ts*DR-suppressing therapy with an antibody medicine can be considered.

Example 6

Providing Subjects with Immunodynamics-Related Information (2)

Certain cell-count of each of multiple types of immunocompetent cells in blood collected from the subject was assigned into the discriminant function obtained in Example 2, the given discriminant score belonged to <GOOD/higher X-axis group; n=54 > which is expressed as an immunodynamics chart in FIG. 8. Moreover, the average number of NK cells per 1 μL blood of GOOD/higher X-axis group was 135.2 (cells/μL).

Therefore, the NK activity index and NK-cell ADCC activity index of the subject was calculated as follows:

NK activity index

=1.257 (monocyte influence degree (%))×0.032 (Act.Th1 influence degree (%))×0.172 (Tc*DR influence degree (%)) ÷87.547 (the sum of influence degree (%))×135.2 (the average number of NK cells per 1 μL blood of the data cluster)=0.0107

NK-cell ADCC activity index

=1.257 (monocyte influence degree (%))×0.019 (Act.Th2 influence degree (%))×0.068 (CD20*DR influence degree (%))÷87.547 (the sum of influence degrees (%))×135.2 (the average number of NK cells per 1 μL blood of the data cluster)=0.0025

Example 7

Providing Subjects with Immunodynamics-Related Information (3)

Figure 41:
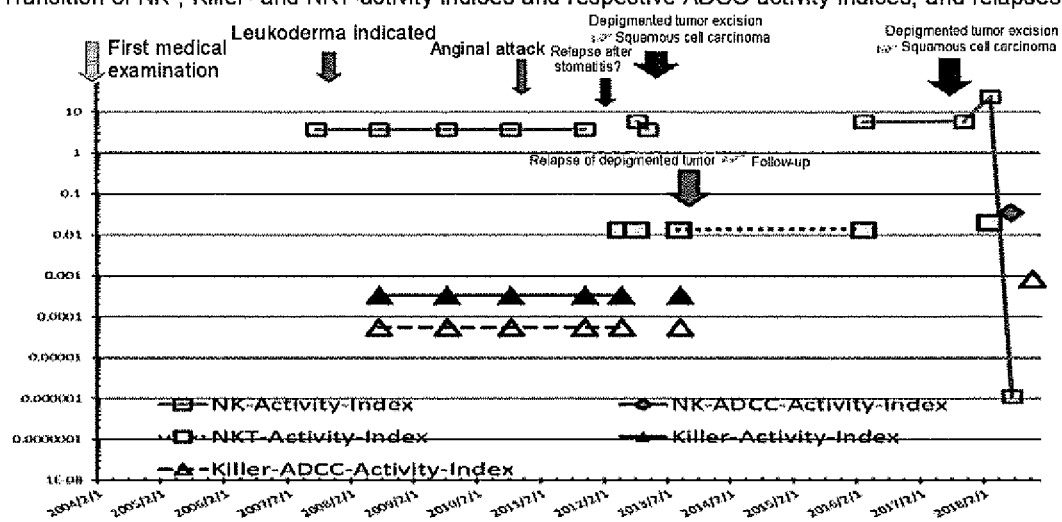
FIG. 41 represents transition of different indices in subjects with lingual cancer.

In a subject suffering from lingual cancer (male, born in 1947), the NK activity index, NK ADCC-activity index, NKT activity index, ADCC activity index of NKT (NKT-ADCC-Activity Index), killer T-cell activity index (Killer Activity Index), and killer T-cell ADCC activity index (Killer-ADCC-Activity Index) were observed over time. The results are shown in FIG. 41.

In the beginning of May, 1997, the subject received preoperational radiotherapy with irradiation of 30 Gy, then experienced a radical operation of the cancer in the left radix linguae by incision of mandible in midline. After that, the cancer relapsed repeatedly in oral mucosal epithelium every three years, approximately. The inventor has been his attending physician since 2004, started inspection and observation over time. Immunity examination also stated in the middle of July, 2007.

As therapy, the subject was received an instruction to take supplements and Chinese herbal medicines that was said to increase immunocompetence. In the beginning of October, 2007, a few white spots (major axis; 1-2 mm) was pointed out, and follow-up was required. In the middle of September, 2010, the subject had chest pain during night which persists to the next morning. Late in September, the subject consulted to a general hospital, and admitted thereto for close examination. The subject was diagnosed with angina with coronary vasospasm, and treatment started. A strict instruction was given for antianginal agents and nutritional therapy, lipid restriction, in particular. The instruction for prohibiting alcohol was not strictly followed, and intemperance lasted.

The subject caught a cold in April, 2012, made it worse and suffered from bad canker sores for one month. In the immunological examination in the beginning of May, 2015, NK activity index (NK-Activity-Index) was absent and a relapse was suspected. In the immunological examinations in beginning of August, and in beginning of October, same year, NK activity index had been recovered, but killer T-cell activity index (Killer-Activity-Index) and killer T-cell ADCC activity index were absent in both two examinations. NKT activity index (NKT-Activity-Index) was also absent in the beginning of October. Clinically, several locations containing small cauliflower-shaped tumor masses that were more evident than white spot were observed. Since their number and size were increased, the subject consulted again to the hospital where he had the radical operation of cancer in the beginning of November, 2012, and the relapse was confirmed. Although an ablative surgery was given late in November, same year, there are too many small tumor masses to ablate all, leaving some unablated. It is considered that cooperation of killer activity and NK activity had suppressed recurrence to this point.

In the beginning of April, 2013, NK-cell activity index, etc. was still absent after the operation, though both NKT-cell activity index and killer activity index had recovered. Fortunately, NKT activity index, killer T-cell activity index, and killer T-cell ADCC activity index had been established, and a follow-up examination was an acceptable treatment in immunological viewpoint, too.

In the examination in the middle of March, 2016, NK-cell activity index had recovered, but killer T-cell activity index was still absent, while NKT-cell activity index had been maintained. In the end of September, 2017, the subject received the third operation. Fortunately, there was no metastasis, with only local recurrence of squamous cell carcinoma. In two post-operational examinations, NK-cell activity index had been maintained former value, but killer T-cell activity index was still absent, and in the examination in the beginning of March, 2018, NKT-cell activity index had recovered. Most recent examination in the middle of July, 2018, although NK-cell activity index was at a low value, a desired NK cell ADCC activity index had been recovered.

It is considered that, if the subject strictly follows diet cure and avoids intemperance in future and thereby keep NK-cell activity index and NK-cell ADCC activity index or induce both killer T-cell activity and killer T-cell ADCC activity, it would be possible to prevent recurrence or metastasis. If immunological condition goes bad in future, immunocytic therapy should be considered, although it is an expensive therapy. In the examination in the beginning of November, 2018, only killer T-cell activity had been induced, which is undependable. The follow-up examination in the general hospital was once a month at first, but it is now once in two months, and it is concerned that any recurrence or metastasis might be overlooked. Besides, this subject also suffers from severe pollinosis, and should be recommended to take medicines for pollinosis during severe pollinotic seasons. Anyway, immunological transition should be followed by future care and examinations.

In the first place, in anti-tumor immunity, it is ideal to be able to induce a high level of killer T-cell activity index, which is the leading role in adoptive immunity. Moreover, when immunity by NK cell is the main constituent, induction of NK cell ADCC activity is important in anti-tumor immunity. In this subject, even though immunity by NK cell is the main constituent, NK cell ADCC activity index was absent, and furthermore, killer T-cell activity index, killer T-cell ADCC activity index and NKT-cell activity index were at low levels. In future, it is planned to monitor care such that both killer T-cell activity index and killer T-cell ADCC activity index would appear.

Example 8

Providing Subjects with Immunodynamics-Related Information (4)

Figure 42:
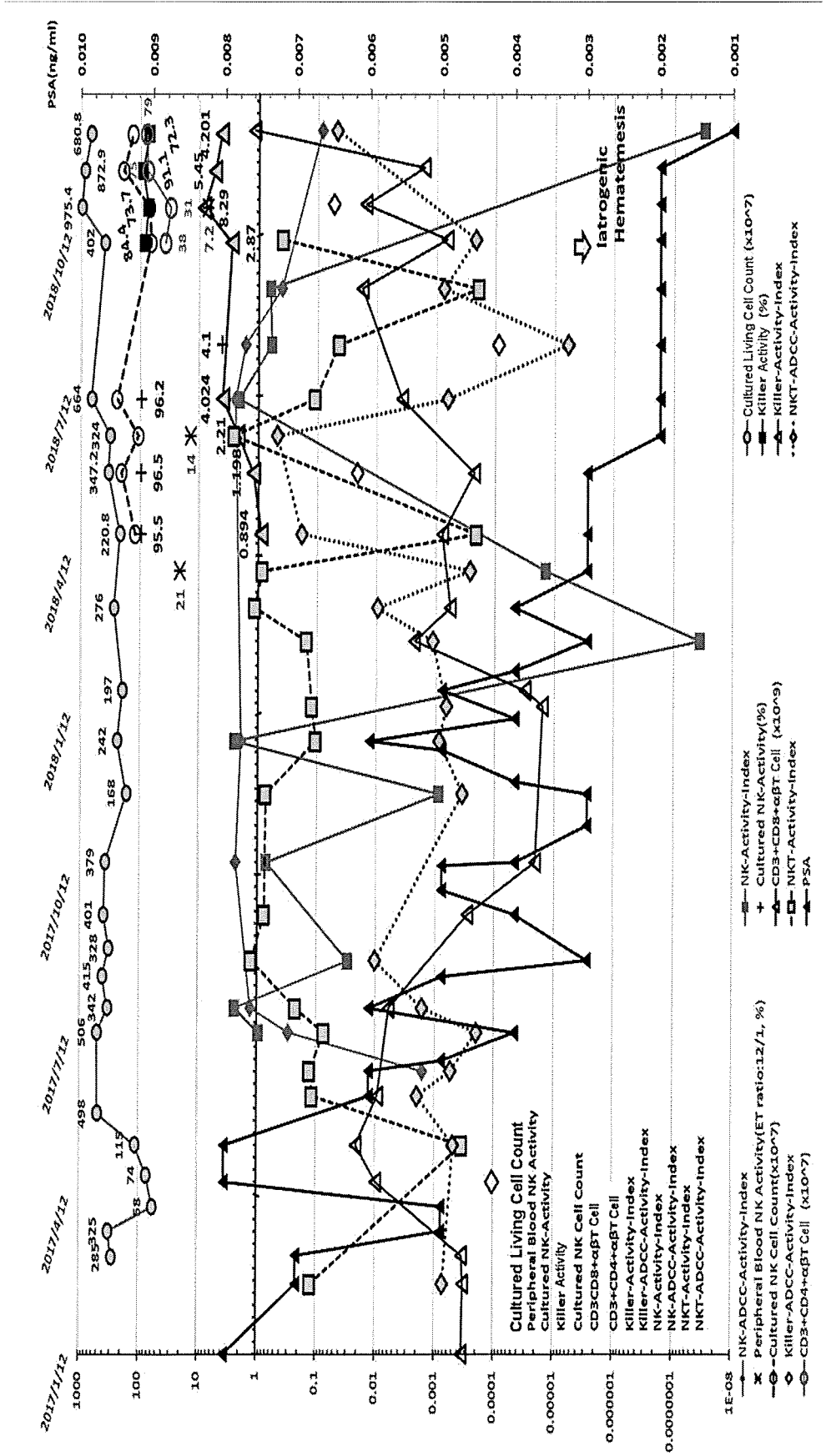
FIG. 42 represents transition of different indices in subjects with prostate cancer. Cultured Living Cell Count indicates the number of lymphocytes that were collected from 40 ml of venous blood drawn from the subject, cultured, and still viable on the day of administering blood transfusion. Peripheral Blood NK Activity is the activity of NK cells collected from peripheral blood of the subject, measured by flow-cytometry using calcein-AM fluorescent staining dye (effector-target ratio; 12:1). Cultured NK Activity (the activity of cultured NK cells) is the activity of NK cells collected from 40 ml of venous blood drawn from the subject and cultured, measured by flow-cytometry using calcein-AM fluorescent staining dye (effector-target ratio; 12:1). Killer Activity is the activity of killer T-cells collected from 40 ml of venous blood drawn from the subject and cultured, measured by flow-cytometry using calcein-AM fluorescent staining dye (effector target ratio; 12:1). Cultured NK Cell Count (the number of cultured NK cells) indicates the number of NK cells that were collected from 40 ml of venous blood drawn from the subject and cultured. Cell counts are given in a unit of $*10^7$ cells. CD3+CD8-αβ-T cell indicates the number of CD3+CD8+αβ-T cells that were collected from 40 ml of venous blood drawn from the subject and cultured. This is a cell fraction which contains killer T-cells and given in a unit of $*10^9$ cells. CD3+CD4+αβ-T cell indicates the number of CD3+CD4+αβ-T cells that were collected from 40 ml of venous blood drawn from the subject and cultured. This is a cell fraction which contains helper T-cells and given in a unit of $*10^7$ cells.
Figure 43:
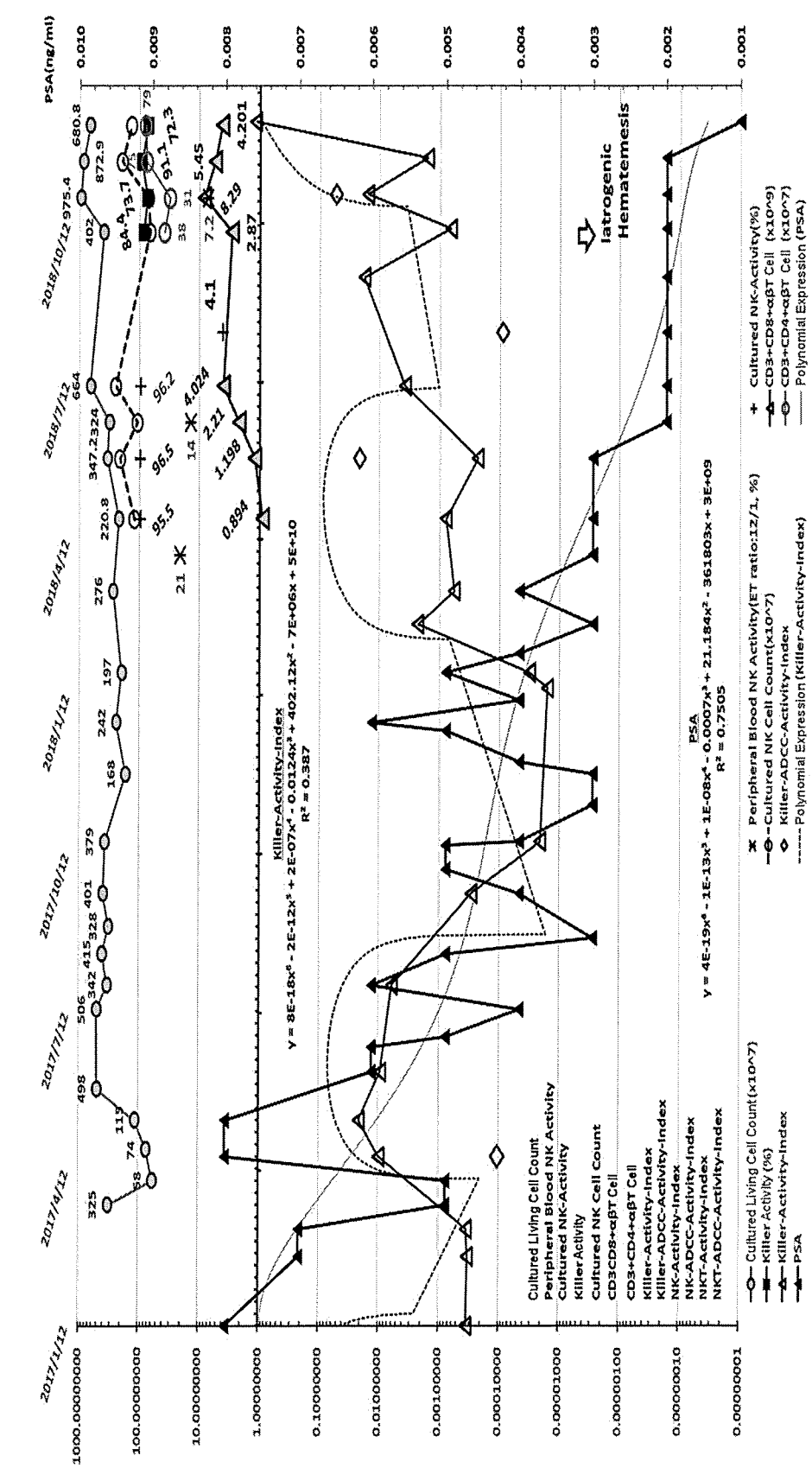
FIG. 43 represents transition of killer T-cell activity index and killer T-cell ADCC activity index in a subject with prostate cancer.
Figure 44:
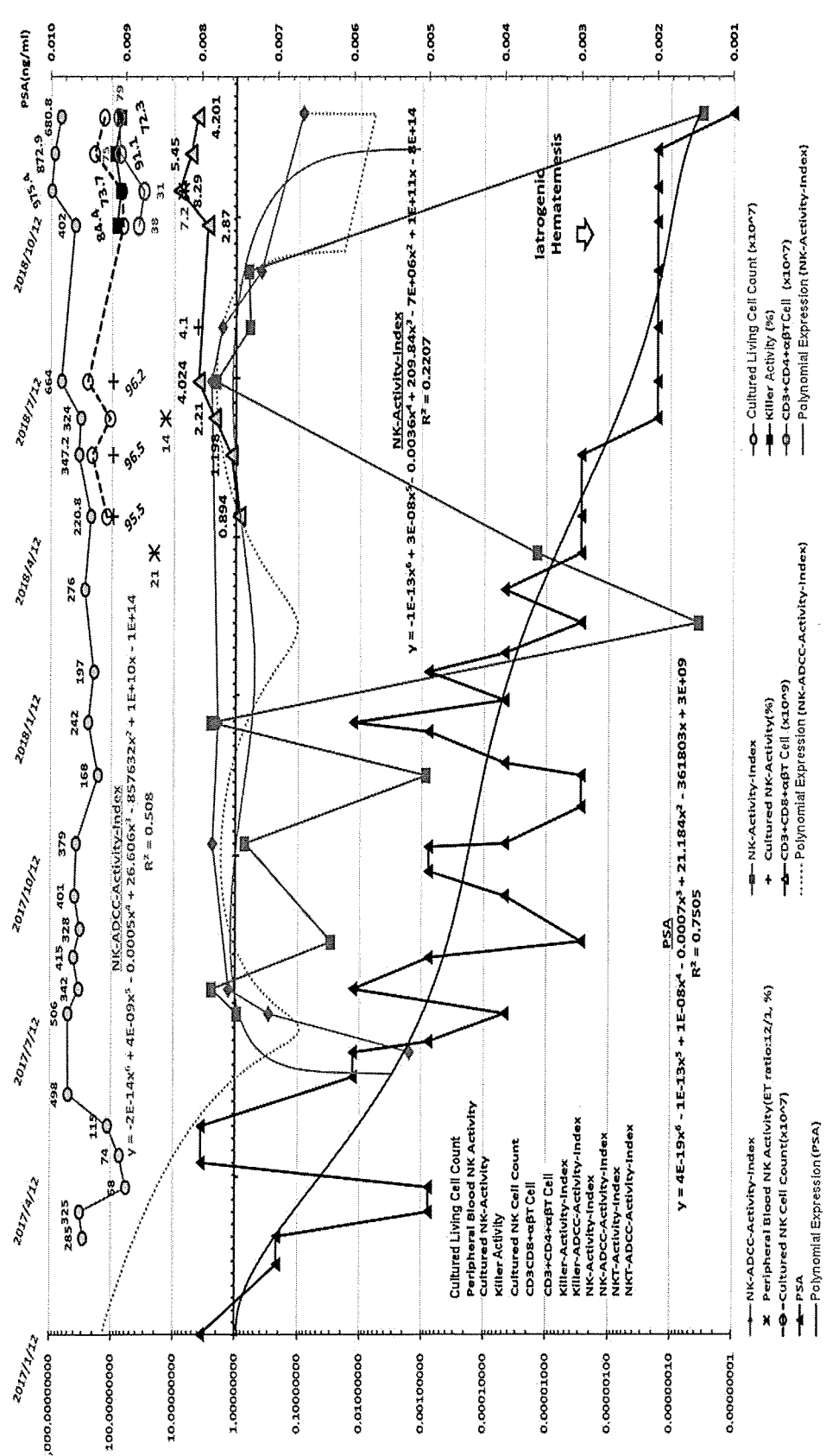
FIG. 44 represents transition of NK-cell activity index and NK-cell ADCC activity index in a subject with prostate cancer.
Figure 45:
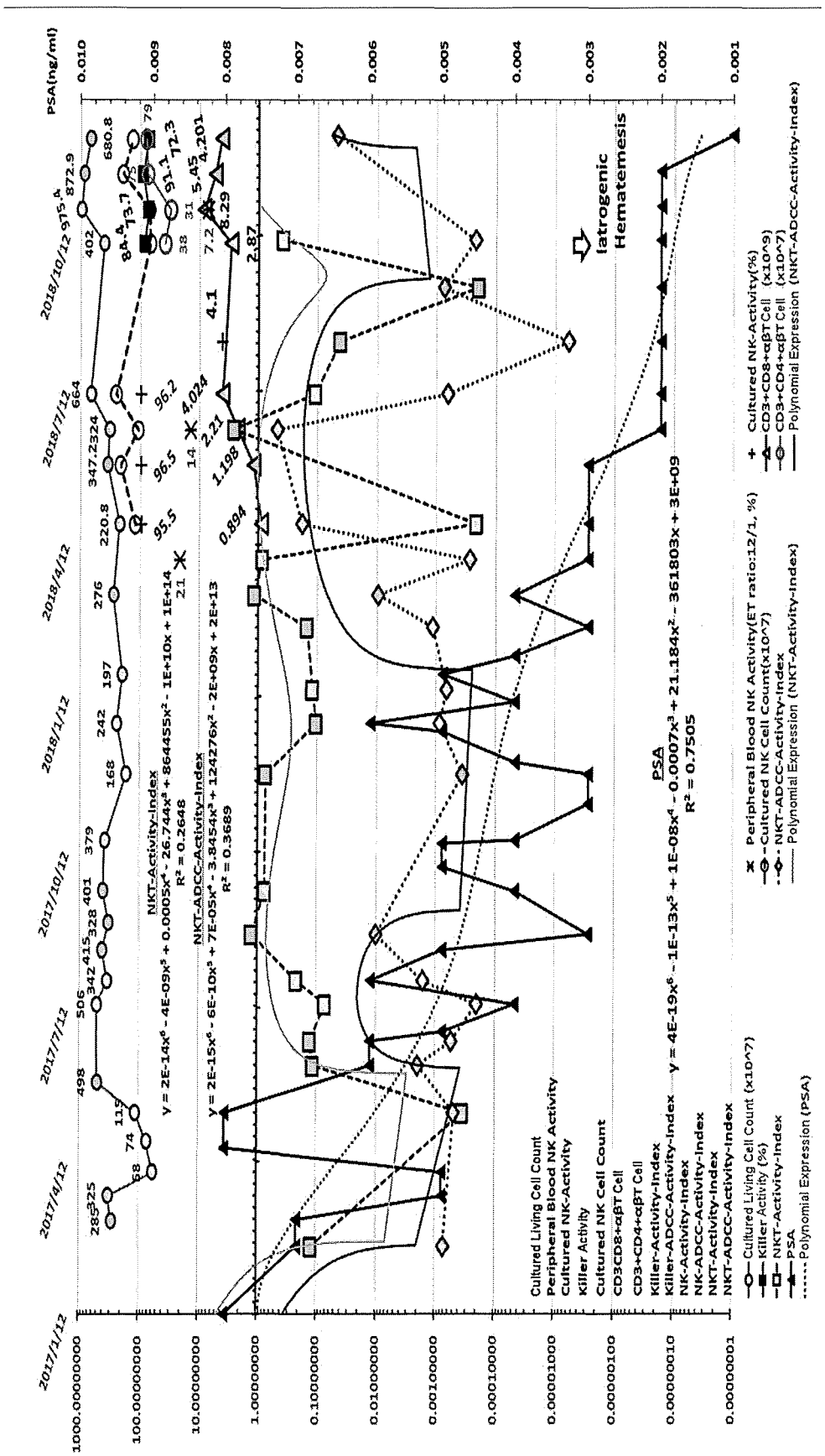
FIG. 45 represents transition of NKT-cell activity index and NKT-cell ADCC activity index in a subject with prostate cancer.

In a subject suffering from prostate cancer (male, born in 1940), PSA value, NK activity index, NKADCC-activity index, NKT activity index, ADCC activity index of NKT (NKT-ADCC-Activity Index), killer T-cell activity index (Killer Activity Index), and killer T-cell ADCC activity index (Killer-ADCC-Activity Index) were observed over time. The results are shown in FIG. 42-44. FIG. 42 shows transition of all indices, FIG. 43 shows transition of killer T-cell activity index and killer T-cell ADCC index in this subject, FIG. 44 shows transition of NK-cell activity index and NK-cell ADCC index in this subject, and Fig, 45 shows transition of NKT-cell activity index and NKT-cell ADCC index in this subject.

The subject received a prostatectomy in 2002 as radical cure for prostate cancer. He has been receiving follow-up examination because PSA value had been elevated from December, 2003 to January, 2004. Here, PSA (prostate-specific antigen) has been used as a prostate cancer marker, and it is considered that PSA value is elevated by 2.2 ng/ml for 1 gram of cancer (Lerner SE, Seay TM, Blute ML, Bergstralh EJ, Barrett D, Zincke H: Prostate specific antigen detected prostate cancer (clinical stage T1c): an interim analysis. J Urol 155:821-826, 1996), and the ultrasensitive measurement limit of PSA value is 0.001 ng/ml. The subject has past history of hypertension and hypothyroidism, and has been taking Amlodin, Tanatril, and Thyradin S. Hormonal therapy with dihydrotestosterone (DHT) inhibitor started in 2009.

The inventor has been the attending physician since January, 2010. Immunotherapy has been considered since February, 2010, but has not been introduced, because the subject is categorized into GOOD group in the immunological examination in February 9, same year and seem to be in immunologically good condition regardless of an rising tendency of PSA value. The subject fell into BAD group in the immunological examination in May 11, same year, and instructed to receive vaccine therapy. It became clear after two years that the subject fell into BAD group during the season of Japanese cedar pollinosis. After this, treatment for pollinosis has been given in combination. Furthermore, the subject was instructed to strictly follow diet cure.

On May 22, 2012, the immunological condition went extremely worse and was categorized into BAD group. This is considered to be because of pollinosis. After that, the subject was instructed to take medicine for perennial allergy throughout a year. Basically, Allegra (fexofenadine) was taken. In the immunological examination on December 4, same year, the immunological condition transferred from GOOD to BAD group, indicating exacerbation of immunological condition. Therefore, the subject was instructed to avoid overeating and strictly keep abstinence.

Hormone therapy, Casodex therapy started on December 18, 2014. From July 1, 2016, in addition to Allegra, Claritin started to be administered in combination. By these treatments, it was expected that the eosinophil count in peripheral blood can be suppressed under $100/mm^3$. After that, the eosinophil count in peripheral blood started to decrease.

Immunity was kept in GOOD group to February, 2017, but fell in MODERATE group in the examination in March, same year. Therefore, vaccine therapy was terminated and changed to NK-cell adoptive immunotherapy from April. Although vaccine maintenance therapy has been carried out once a month, no effect was observed as vaccine. Although folk medicines, Chinese herbal medicines, etc. were used in combination, no obvious effect was observed.

The subject changed clinic in April, 2018, but continued NK-cell therapy. By NK-cell therapy, PSA value decreased to 0.002, which is closed to measurement limit, i.e., 0.001. However, although the activity of NK cells was 96.2% (effector target ratio; 12:1) and the cultured NK-cell count (hereinafter, "cultured" means the lymphocytes collected from 40 μL of peripheral blood of the subject and cultured) was 2.49 billion and the cultured CD8+αβ-T cell count was 4.024 billion on July 10, 2018, NK cell activity extremely decreased to 4.1% (effector target ratio; 12:1) on Aug. 10, 2018. Moreover, an increase of αβ-T cells was confirmed by a simple test. Therefore, NK-cell therapy was replaced with αβ-T cell therapy from Aug. 10, 2018. Moreover, the subject changed clinic.

Illustration of Course and Transition of Each Activity Index of Killer-T Cell, NK Cell and NKT Cell For anti-tumor immunity, maintaining high levels of the indices is essential. Particularly, induction of both killer T-cell activity and killer antibody-dependent cellular cytotoxicity at high level is essential. This is also evident from the relationship with PSA value.

The cultured living cell count was extremely low on Apr. 6, 2017, April 24, same year, and May 11, same year for unknown reason. It is presumably because of systemic physical deconditioning of the subject.

Appearance of all six indices on the day of immunological examination is the condition for inducing a potent anti-tumor immunity, However, barely three indices hardly appeared. For indices other than killer T-cell ADCC activity index, connecting lines were drawn where the index was absent. In the case of killer T-cell ADCC activity index, it appeared only four times and no connecting line was drawn. In cases where the index was absent, it is presumed to decrease to $10^{-9}$-$10^{10}$ level. Dendritic cell vaccine therapy had been performed until February, 2017, but PSA value had never been under 0.008 ng/ml. It was therefore switched to NK-cell therapy, which was carried out once a month from March 9. It was then changed to αβ-T cell therapy from Aug. 9, 2018, and PSA value further decreased, Besides, Iatrogenic Hematemesis on Oct. 6, 2018 indicates an incidence of major bleeding (approximately 600 ml) and emergency operation after drinking small amount of alcohol on the day of gastric mucosal biopsy. Although the killer activity had successfully increased until this and further improvement had been expected, immunity dropped at once after this day. It is considered to be because of this incidence. The result of biopsy was not a cancer.

Transition of Killer T-Cell Activity Index and Killer T-cell ADCC Index

Killer T-cell activity index (Killer Cell Activity Index: Killer-AI) is in inverse correlation with PSA value, and thus when killer T-cell activity index is high, PSA value is low, while killer T-cell activity index is low or is not induced, PSA value is high.

On Apr. 20, 2017, killer T-cell activity index (Killer-Activity-Index) was 0.00978821, and killer T-cell antibody-dependent cellular cytotoxicity index (Killer-ADCC-Activity-Index) was 0.000104608. Both indices appeared together only on May 29, 2018. PSA value was further decreased presumably due to the appearance of both indices.

The treatment was changed to αβ-T cell adoptive immunotherapy from Aug. 10, 2018, in expectation of further enhancement and induction of killer activity.

In order to measure influences and effects by the cellular therapy, an examination was performed for subsets of peripheral blood lymphocytes.

On Apr. 3, 2018, the activity of the peripheral blood NK cells (uncultured) was 21%. On April 24, same year, the cultured living cell count was 2.210 billion, and the activity of cultured NK cells was 95.5%, the cultured NK-cell count was 1.210 billion, the CD3+CD8+αβ-T cell count was 0.890 billion.

On May 29, same year, the cultured living cell count was 3.470 billion, the activity of cultured NK cells was 96.5%, cultured NK-cell count was 2.110 billion, and the CD3+CD8+αβ cell count was 1.2 billion.

On June 19, same year, the cultured living cell count was 3.240 billion, the activity of peripheral blood NK cells (uncultured) was 14%, the activity of cultured NK cells was not measured, cultured NK-cell count was 1.07 billion, and the CD3+CD8+αβ cell count was 2.210 billion.

On July 10, same year, the cultured living cell count was 6.640 billion, the activity of cultured NK cells was 97.4%, cultured NK-cell count was 2.490 billion, and the CD3+CD8+αβ cell count was 4.020 billion.

On August 10, same year, the activity of cultured NK cells was extremely decreased to 4.1%. This was the reason for determining that it was the time to change to aαβ-T cell therapy.

In the examination on October 7, same year, the cultured living cell count was 4.020 billion, the activity of cultured killer T-cells was 84.4%, the cultured NK-cell count was 0.670 billion, the CD3+CD8+αβ cell count was 2.870 billion, and the CD3+CD4+αβ-T cell count was 0.380 billion.

On October 27, same year, the cultured living cell count was 9.750 billion, the activity of cultured killer T-cells was 73.7%, the cultured NK-cell count was 0.670 billion, the activity of peripheral blood NK cells (uncultured) was extremely decreased to 72%, the CD3+CD8+αβ cell count was 8.290 billion, and the CD3+CD4+αβ-T cell count was 0.310 billion.

On November 17, same year, the cultured living cell count was 8.730 billion, the activity of cultured killer T-cells was 91.1%, the cultured NK-cell count was 1.960 billion, the CD3+CD8+αβ-T cell count was 5.450 billion, and the CD3+CD4+αβ-T cell count was 0.750 billion.

On December 8, same year, the cultured living cell count was 6.810 billion, the activity of cultured killer T-cells was 72.3%, the cultured NK-cell count was 1.360 billion, the CD3+CD8+αβ-T cell count was 4.2 billion, and the CD3+CD4+αβ-T cell count was 0.790 billion. Note that the listing of indices is omitted.

Transition of NK-Cell Activity Index and NK-Cell ADCC Index

The treatment was changed to NK-cell therapy from Mar. 9, 2017. NK-cell activity index (NK-Activity-Index) and NK-cell ADCC activity index (NK-ADCC-Activity-Index) did not appear before NK-cell therapy, but the treatment induced their appearance.

Approximately five month later, on July 28, same year, NK-cell activity index was as high as 2.397, and indicated 2.463 which was the highest value on Dec. 27, 2017. In a similar way as in killer T-cell activity index, when NK-cell activity index was high, PSA value decreased, indicating that they are in inverse correlation. NKT-cell ADCC activity index decreased, in particular, from Aug. 10, 2018, and aforementioned killer T-cell ADCC activity index appeared on May 29, 2018, but has been disappeared since then. Therefore, αβ-T cell adoptive immunotherapy was considered to be appropriate, and the treatment was changed from NK-cell therapy to αβ-T cell adoptive immunotherapy. It is natural that NK-cell activity index and NK-cell ADCC activity index last appeared on Sep. 11, 2018 and disappeared until December 10, presumably due to the change in cell therapy.

Transition of NKT-Cell Activity Index and NKT-Cell ADCC Index

NKT-cell activity index (NKT-Activity-Index) is in inverse correlation with PSA value in a similar way as the NK-cell activity index and the killer T-cell activity index.

On Jun. 19, 2018, NKT-cell activity index and NKT-cell ADCC activity index (NKT-ADCC-Activity-Index) were both induced at the highest level. It is considered that PSA value was further decreased because of this. However, it last appeared in the beginning of October, 2018 and has not appeared thereafter.

From Aug. 10, 2018, the treatment was changed to αβ-T cell adoptive immunotherapy in expectation of induction of the appearance of killer T-cell activity index. In the analysis of peripheral blood lymphocyte subset on Dec. 10, 2018, a desired high level of Killer-Activity-Index could be induced. Although NKT activity could not be induced, the appearance of NKT-ADCC-Activity-Index could be induced. It is considered that due to the appearance of these indices the desired PSA value <0.001 could be achieved in 1 year and 10 months.

Prediction of Tumor Mass Destruction

By using each of the activity indices, the degree of tumor mass that can be destroyed by an immunocytic therapy can be predicted.

Usually, it is said that 1 gram of tumor mass contains $10^9$ cancer cells. In prostate cancer, it is said that 1 gram of tumor mass exist if there is an increase in PSA value by 2.2 ng/ml.

Accordingly, based on the killer T-cell activity index,
weight of tumor mass to be decreased (g)
=the number of cultured killer T-cells (cells)÷12×the activity of cultured killer T-cells (effector target ratio; 12:1)× killer T-cell activity index÷$10^9$ (cells)/1 (g);
wherein killer T-cell activity is introduced in decimal percentage, but not in integer percentage.

Moreover, based on the killer T-cell ADCC activity index,
weight of tumor mass to be decreased (g)
=the number of cultured killer T-cells (cells)÷12×the activity of cultured killer T-cells (effector target ratio; 12:1)× killer T-cell ADCC activity index=$10^9$ (cells)/1 (g);
wherein killer T-cell activity is introduced in decimal percentage, but not in integer percentage.

In Oct. 29, 2018, the number of cultured killer T-cells (CD3+CD8+αβ-T cell) was 8.29×$10^9$, the activity of cultured killer T-cells (effector target ratio; 12;1) was 73.7%, the killer T-cell activity index was 0.015619, and the killer T-cell ADCC activity index was 0.053472.

By assigning into the above formula,
based on the killer T-cell activity index, weight of tumor mass to be decreased is:

$$8.29 \times 10^9 \text{ (cells)} \div 12 \times 0.737 \times 0.015619 \div 10^9 \text{ (cells)}/1 (g) \approx 0.00795 \ (g)$$

and the weight of tumor mass to be decreased can be predicted to be 0.00795 g.

This can be converted into PSA value:

$$0.00795 \times 2.2 \approx 0.0175 \text{ (ng/ml)}$$

indicating that the PSA value is predicted to decrease by 0.0175 ng/ml at a time.

Moreover, based on the killer T-cell ADCC activity index, weight of tumor mass to be decreased was:

$$8.29 \times 10^9 \text{ (cells)} \div 12 \times 0.737 \times 0.053472 \div 10^9 \text{ (cells)}/1 (g) \approx 0.02722 \ (g)$$

and this was converted into the PSA value:

$$0.02722 \times 2.2 = 0.059895 \ (ng/ml).$$

When both of these are added, it means that 0.03517 g of tumor mass will be destroyed. 0.077395 ng/ml of decrease in PSA value is predicted.

On Dec. 10, 2018, Killer-Activity-Index was 1.168043, and no Killer-ADCC-Activity-Index appearance was induced or evoked.

(8.29×$10^9$ (cells)÷12×0.723×1.168043÷$10^9$ (cells)/1 (g)=0.58341 (g) of destruction and reduction were predicted.

When this is converted into PSA value, a reduction of 0.58341×2.2=1.28350 (ng/ml) is predicted. A strong activity was induced and evoked as predicted, and PSA value could be decreased, as desired, to below 0.001 ng/ml which is an ultrasensitive measurement limit.

Similarly, by performing a similar calculation for NK cell, the weight of tumor mass that was destroyed by NK-cell therapy can be predicted.

Based on the NK-cell activity index,
weight of tumor mass to be decreased (g)
=the number of cultured NK cells (cells)÷12×the activity of cultured NK cells (effector target ratio; 12:1)×NK-cell activity index+$10^9$ (cells)/1 (g);
wherein the activity of NK cells is introduced in decimal percentage, but not in integer percentage.

Moreover, based on the NK-cell ADCC activity index,
weight of tumor mass to be decreased (g)
=the number of cultured NK cells (cells)÷12×the activity of cultured NK cells (effector target ratio; 12:1)×NK-cell ADCC activity index=$10^9$ (cells)/1 (g); wherein the activity of NK cells is introduced in decimal percentage, but not in integer percentage.

On Jul. 10, 2018, the number of cultured NK cells was 2.49×$10^9$, the activity of cultured NK cells (effector target ratio; 12:1) was 96.2%, NK-cell activity index was 2.102970, and NK-cell ADCC activity index was 2.484033.

By assigning into the above formula,
the NK-cell activity index was predicted to reduce weight of tumor mass by:

$$2.49 \times 10^9 \text{ (cells)} \div 12 \times 0.962 \times 2.102970 \div 10^9 \text{ (cells)}/1(g) \approx 0.41978 \text{ (}g\text{), and}$$

the NK-cell ADCC activity index was predicted to reduce weight of tumor mass by:

$$2.49 \times 10^9 \text{ (cells)} \div 12 \times 0.962 \times 2.484033 \div 10^9 \text{ (cells)}/1 (g) \approx 0.495850 \text{ (}g\text{),}$$

and in total, it was predicted to reduce weight of tumor mass by 0.91563 g. Thus, it was presumed that NK-cell therapy was sufficiently effective, although the PSA value was still 0.002 ng/ml. Thereafter, the PSA value remained to be 0.002 and was not reduced, and in addition to it, NK activity and NK-cell count were reduced. Therefore, no effect seems to be expected by NK-cell therapy and the treatment was changed to $\alpha\beta$-T cell therapy.

Similarly, by performing a similar calculation for NKT-cell, the weight of tumor mass that was destroyed by NKT-cell therapy can be predicted.

Based on the NKT-cell activity index,
weight of tumor mass to be decreased (g) can be calculated by:
=the number of cultured NKT cells (cells)÷12×the activity of cultured NKT-cells (effector target ratio; 12:1)×NKT-cell activity index÷$10^9$ (cells)/1 (g); wherein NKT-cell activity is introduced in decimal percentage, but not in integer percentage.

Moreover, based on the NKT-cell ADCC activity index,
weight of tumor mass to be decreased (g) can be calculated by:
=the number of cultured NKT cells (cells)÷12××the activity of cultured NKT-cells (effector target ratio; 12:1)×NKT-cell ADCC activity index÷$10^9$ (cells)/1 (g);
wherein NKT-cell activity is introduced in decimal percentage, but not in integer percentage.

In data of Oct. 9, 2018, the NKT-cell activity index was 0.23397 and the NKT-cell ADCC activity index was 0.000219. NKT cells were cultured separately; although the activity was not measured, it can be predicted that:
assuming the number of cultured NKT cells to be $Z \times 10^9$, and the activity of cultured killer T-cells (effector target ratio; 12:1) to be Znkt;
for the NKT-cell activity index:

$$Z \times 10^9 \text{ (cells)} \div 12 \times Znkt \times 0.23397 \div 10^9 \text{ (cells)}/1 (g) = 0.019498 \times Z \times Znkt \text{ (}g\text{)}$$

of tumor mass can be destroyed. When this is converted into PSA value, a reduction of $0.019498 \times Z \times Znkt \times 2.2 \approx 0.0429 \times Z \times Znkt$ (ng/ml) is predicted.

For NKT-cell ADCC activity index, it can be predicted that:

$$Z \times 10^9 \text{ (cells)} \div 12 \times Znkt \times 0.000219 \div 10^9 \text{ (cells)}/1 (g) = 0.00001825 \times Z \times Znkt \text{ (}g\text{)}$$

of tumor mass can be destroyed. When this is converted into PSA value, a reduction of $0.00001825 \times 2.2 \times Z \times Znkt$ (ng/ml) is predicted. As a result, the sum of these, i.e., $0.019516 \times Z \times Znkt$ (g) will be destroyed.

In the analysis of peripheral blood lymphocyte on Dec. 10, 2018, no appearance of NKT activity index was induced, though the NKT-ADCC-Activity-index was 0.0475174, which was higher as compared to that on October 9, same year.

It is considered that the tumor mass destruction calculated by the indices continues during the period before the administration of next therapy (2-3 weeks). Therefore, the weight of tumor mass which would be destroyed will be the product of the number of grams predicted to be destroyed as mentioned above being multiplied by the number of days (i.e., 14-21). Considering in this way, an effective immunotherapy should be carried out appropriately and precisely such that each index will be increased. An inappropriate immunotherapy might cause an exacerbation, and it is important and essential to keep monitoring immunodynamics. Although the examination takes costs, it should be done if necessary, regardless of the costs.

Besides, the volume of tumor mass that would be destroyed can be presumed if data can be obtained for the respective activity of each lymphocyte in peripheral blood, without culturing each lymphocyte. Moreover, the volume of tumor mass of the subject's cancer that would be destroyed can be presumed by using cancer cells of the subject him/herself for the activity evaluation, not K562 cells which are usually used for activity evaluation.

From the equation: the body weight×(1/13)×each peripheral blood cell count (killer $\alpha\beta$-T, NK or NKT) (/mm$^3$), the total number of effector cells (unit: $10^9$ cells) is obtained. The percentage of the activity of each effector cell can be examined, and the weight of tumor mass which would be destroyed can be predicted using indices obtained from an analysis of the chart of lymphocyte subset immunodynamics and calculating as mentioned above.

Example 9

Generating Improved Discriminant Function

Figure 46:
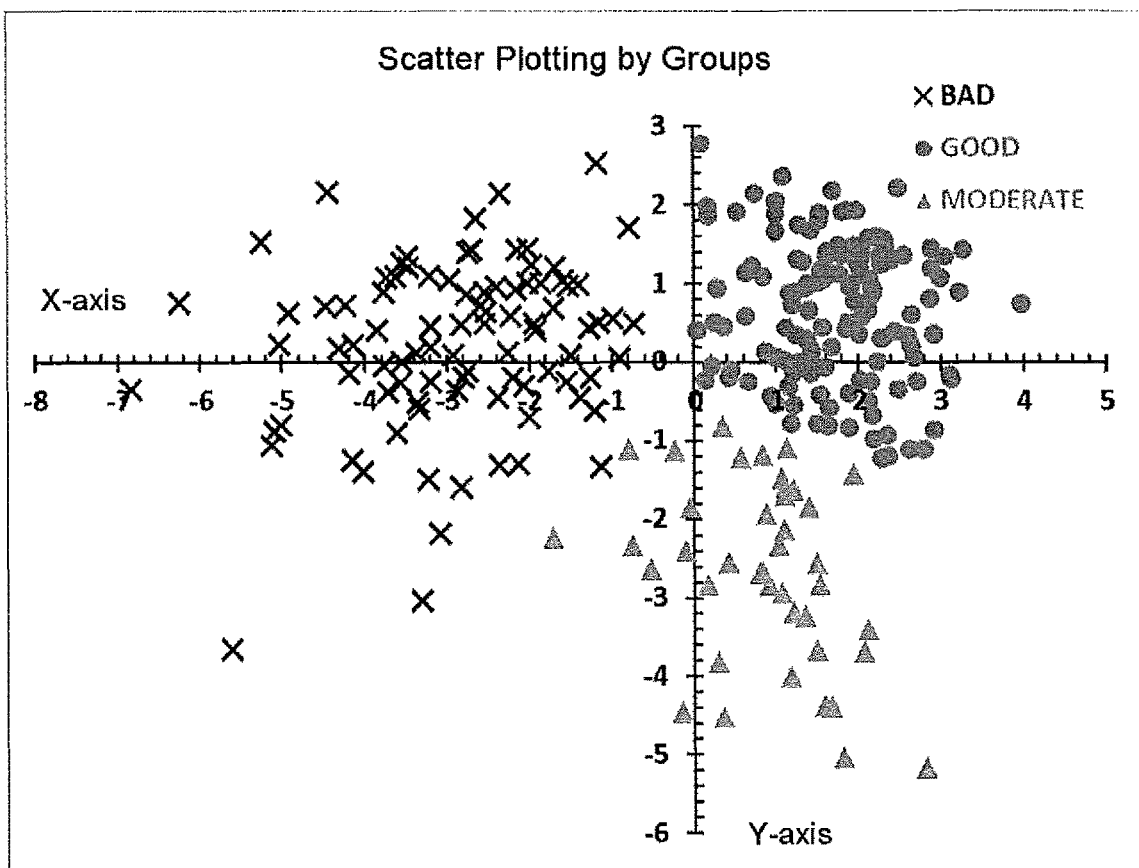
FIG. 46 represents a scatter plot of discriminant scores of 267 cases obtained by a discriminant function generated by targeting the 267 cases.

The subjects were 344 cases that were sorted into GOOD group, MODERATE group in Example 3. A discriminant analysis was performed using 3 groups of GOOD, MODERATE and BAD groups as objective variables and 26 types of immunocompetent cells: CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil as explanatory variables to give a discriminant function. Cases which could not be sorted well in scatter plotting of discriminant scores were excluded, and the discriminant analysis was performed repeatedly. As a result, a discriminant function with 100% discrimination accuracy rate among 267 cases. A scatter plot of discriminant scores in which the first discriminant function values is on X-axis and the second discriminant function values is on Y-axis is shown in FIG. 46. The discriminant score obtained by assigning the cell-count of each of immunocompetent cells of subjects into this discriminant function can be used as an indicator to divide the subjects into multiple groups.

As above, the present invention comprises methods of predicting prognosis of a subject from the cell-counts of multiple types of immunocompetent cells. For instance, for data cluster containing the values of levels of cancerous markers such as prostate-specific antigen (PSA) of individuals and data of the cell-count of each of multiple types of immunocompetent cells in blood collected from the individuals in a number that allows for the discriminant analysis, a multiple regression analysis is performed using PSA value as objective variable and the multiple types of immunocompetent cells are set as explanatory variables, subtracting the expected value from the observed value to give a residual value, and the individuals can be sorted into any number of groups in such a way that the smaller the residual value is, the better the expected prognosis would be. By performing a discriminant analysis using said groups as objective variables and the multiple types of immunocompetent cells are set as explanatory variables, a discriminant function can be obtained. By assigning the cell-count of the multiple types of immunocompetent cells of a subject into the discriminant function and calculating a discriminant score, the group to which the subject belongs can be determined and the prognosis can be predicted. Moreover, by obtaining immunodynamics-related information in each of the sorted groups, immunodynamics-related information of the subject is obtained, and therapy or prophylaxis according to the immunodynamics of the subject can be determined with that information.

The invention claimed is:

1. A method for treating or preventing a disease and/or symptom of a subject based upon supplied immunodynamics-related information, said method comprising:
  (a) supplying immunodynamics-related information to a computer by:
    (i) determining cell-count of each of multiple types of immunocompetent cells in blood collected from a subject;
    (ii) calculating via the computer a discriminant score by assigning the determined cell-count of each of multiple types of immunocompetent cells in blood collected from the subject into a discriminant function;
    (iii) determining a group into which the subject is to be sorted by the calculated discriminant score;
    (iv) displaying on the computer immunodynamics-related information of the determined group,
   wherein;
    the discriminant function is obtained by performing a discriminant analysis on the computer for a data cluster containing data of the condition of an individual and the cell-count of each of multiple types of immunocompetent cells in blood collected from the individual in a number that allows for the discriminant analysis, wherein the condition of the individual is set an objective variable and the multiple types of immunocompetent cells are set as explanatory variables; and
    the group into which the subject is to be sorted is one of the multiple groups that are divided from the data cluster used for obtaining the discriminant function using discriminant scores as indicator; and
  (b) selecting and administering a therapy or prophylaxis for a disease and/or symptom of the subject based upon the displayed immunodynamics-related information of the determined group for the subject, wherein the immunodynamics-related information is obtained by:
    (v) performing a multiple regression analysis via the computer for data of the cell-counts of n types of immunocompetent cells that constitute one group, wherein one type of immunocompetent cell among the n types of immunocompetent cells is set as an objective variable and n-1 types of immunocompetent cells excluding the one type of immunocompetent cell that is set as the objective variable are set as explanatory variables, and wherein n is an integer of 4 or more;
    (vi) ranking the n-1 types of immunocompetent cells in descending order according to the magnitude of the absolute value of the standard partial regression coefficient obtained from the multiple regression analysis;
    (vii) performing a regression analysis via the computer in which the one type of immunocompetent cell that is the objective variable in (v) above is set as an objective variable and the immunocompetent cell that is ranked as the first place in (vi) above is set as explanatory variable, calculating the contribution ratio $\alpha_1$ which is considered as the influence degree of the first-place ranked immunocompetent cell $\beta_1$; and
    (viii) performing a multiple regression analysis via the computer in which the one type of immunocompetent cell that is the objective variable in (vi) above is set as an objective variable and m types of immunocompetent cells from the first to the m-th place ranked in (vii) above are set as explanatory variables, calculating the contribution ratio $\alpha_m$, and calculating the influence degree $\beta_m$ of the immunocompetent cell ranked as m-th place by the following formula:

$$\beta_m = \alpha_m - \alpha_{m-1}$$

for each of the immunocompetent cells ranked from the second to the m-th place; wherein m is more than 3 and up to n-1.

2. The method according to claim 1, wherein the condition of an individual is selected from a group consisting of health, a disease, a disorder, a symptom or prognosis.

3. The method according to claim 1, wherein the immunocompetent cells are three or more selected from a group consisting of: Th17+ lymphocyte, CD3-positive lymphocyte, CD4-positive lymphocyte, CD8-positive lymphocyte, CD20*DR lymphocyte, Th± lymphocyte, Th−2 lymphocyte, Th+2 lymphocyte, Act.Th1 lymphocyte, Act.Th2 lymphocyte, Ti*DR lymphocyte, Ti± lymphocyte, Ti−2 lymphocyte, Ti+2 lymphocyte, Tc*DR lymphocyte, Tc− lymphocyte, Tc+ lymphocyte, Ts*DR lymphocyte, Ts− lymphocyte, Ts+ lymphocyte, NK cell, NKT cell, N3+ cell, monocyte, basophil, eosinophil and neutrophil.

4. The method according to claim 3, wherein the immunocompetent cells comprise Th17+ lymphocyte.

5. The method according to claim 1, wherein the one type of immunocompetent cell that is set as the objective variable in step (vi) is selected from a group consisting of: Tc*DR lymphocyte, CD20*DR lymphocyte, NK cell, NKT cell, basophil, eosinophil and neutrophil.

6. The method according to claim 1 wherein the influence degree evaluated is NK-cell activity by the following formula:

NK-cell activity index

={[monocyte influence degree (%) calculated using NK cell as an objective variable]×[Act.Th1 lymphocyte influence degree (%) calculated using NK cell as an objective variable]×[Tc*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 µL blood of the data cluster);

provided that, in multiple regression analysis in which NK cell is set as the objective variable, the standard partial regression coefficients of monocyte, Act.Th1 lymphocyte and Tc*DR lymphocyte are all positive.

7. The method according to claim 1 wherein the influence degree evaluated is NK-cell ADCC (antibody-dependent cellular cytotoxicity) activity by the following formula:

NK-cell ADCC activity index

={[monocyte influence degree (%) calculated using NK cell as an objective variable]×[Act.Th2 lymphocyte influence degree (%) calculated using NK cell as an objective variable]×[CD20*DR lymphocyte influence degree (%) calculated using NK cell as an objective variable]÷[the sum of the respective influence degrees (%) of all immunocompetent cells in which the influence degrees are calculated using NK cell as an objective variable]}×(the average number of NK cells per 1 µL blood of the data cluster);

provided that, in multiple regression analysis in which NK cell is set as the objective variable, the standard partial regression coefficients of monocyte, Act.Th2 lymphocyte and CD20*DR lymphocyte are all positive.

8. The method according to claim 1 wherein the influence degree evaluated is NKT-cell activity by the following formula:

NKT-cell activity index

={[monocyte influence degree (%) calculated using NKT cell as the objective variable]×[Act.Th1 lymphocyte influence degree (%) calculated using NKT cell as the objective variable]×[Tc*DR lymphocyte influence degree (%) calculated using NKT cell as the objective variable]÷[the sum of the respective influence degrees (%) of all immunocompetent cells in which the influence degrees are calculated using NKT cell as the objective variable]}×(the average number of NKT cells per 1 µL blood of the data cluster);

provided that, in multiple regression analysis in which NKT cell is set as the objective variable, the standard partial regression coefficients of monocyte, Act.Th1 lymphocyte and Tc*DR lymphocyte are all positive.

9. The method according to claim 1 wherein the influence degree evaluated is NKT-cell ADCC (antibody-dependent cellular cytotoxicity) activity by the following formula:

NKT-cell ADCC activity index

={[monocyte influence degree (%) calculated using NKT cell as the objective variable]×[Act.Th2 lymphocyte influence degree (%) calculated using NKT cell as the objective variable]×[CD20*DR lymphocyte influence degree (%) calculated using NKT cell as the objective variable]÷[the sum of the respective influence degrees (%) of all immunocompetent cells in which the influence degrees are calculated using NKT cell as an objective variable]}×(the average number of NKT cells per 1 µL blood of the data cluster);

provided that, in multiple regression analysis in which NKT cell is set as the objective variable, the standard partial regression coefficients of monocyte, Act.Th2 lymphocyte and CD20*DR lymphocyte are all positive.

10. The method according to claim 1 wherein the influence degree evaluated is killer T-cell activity by the following formula:

killer T-cell activity index

={[monocyte influence degree (%) calculated using Tc*DR lymphocyte as the objective variable]×[Act.Th1 lymphocyte influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 µL blood of data cluster);

provided that, in multiple regression analysis in which Tc*DR lymphocyte is set as the objective variable, the standard partial regression coefficients of monocyte and Act.Th1 lymphocyte are both positive.

11. The method according to claim 1 wherein the influence degree evaluated is killer T-cell ADCC (antibody-dependent cellular cytotoxicity) activity by the following formula:

killer T-cell ADCC activity index

={[monocyte influence degree (%) calculated using Tc*DR lymphocyte as the objective variable]×[Act.Th2 lymphocyte influence degree (%) calculated using Tc*DR lymphocyte as the objective variable]×[CD20*DR influence degree (%) calculated using Tc*DR lymphocyte as the objective variable]÷[the sum of the respective influence degrees (%) of all immunocompetent cells in which the influence degrees are calculated using Tc*DR lymphocyte as the objective variable]}×(the average number of Tc*DR lymphocytes per 1 µL blood of data cluster)

provided that, in multiple regression analysis in which Tc*DR lymphocyte is set as the objective variable, the standard partial regression coefficients of monocyte, Act.Th2 lymphocyte and CD20*DR lymphocyte are all positive.

12. The method of claim 1 wherein cell-count of each of multiple types of immunocompetent cells in blood collected from the subject is determined by double staining, triple staining or quadruple staining, each in combination with flow cytometry.

* * * * *